(12) United States Patent
Ng et al.

(10) Patent No.: US 7,204,989 B1
(45) Date of Patent: Apr. 17, 2007

(54) HEV ANTIGENIC PEPTIDE AND METHODS

(75) Inventors: Hon Mun Ng, Hong Kong (HK); Stanley Im, Hong Kong (HK); Jizhong Zhang, Hong Kong (HK)

(73) Assignee: Yang Sheng Tang Company Limited, Haikou (CN)

( * ) Notice: Subject to any disclaimer, the term of this patent is extended or adjusted under 35 U.S.C. 154(b) by 205 days.

(21) Appl. No.: 10/089,292

(22) PCT Filed: Sep. 28, 2000

(86) PCT No.: PCT/IB00/01393

§ 371 (c)(1),
(2), (4) Date: Aug. 28, 2002

(87) PCT Pub. No.: WO01/22916

PCT Pub. Date: Apr. 5, 2001

(30) Foreign Application Priority Data

Sep. 30, 1999 (CA) .................... 2283538

(51) Int. Cl.
*A61K 39/29* (2006.01)
*G01N 33/53* (2006.01)
*C12P 21/00* (2006.01)

(52) U.S. Cl. .................... 424/225.1; 435/7.1; 435/975; 424/93.1

(58) Field of Classification Search ................ 530/350, 530/388.2; 424/225.1, 189.1, 192.1, 130.1, 424/93.1, 93.2; 435/69.1
See application file for complete search history.

(56) References Cited

U.S. PATENT DOCUMENTS 5,686,239 A * 11/1997 Reyes et al. .................. 435/5
5,741,490 A * 4/1998 Reyes et al. .............. 424/189.1
6,514,690 B1 * 2/2003 Li et al. ........................ 435/5

OTHER PUBLICATIONS

Khudyakov et al. Virol. 1994, pp. 390-393.*
Catalog of amersham pharmacia biotech 1998, pp. 86.*

* cited by examiner

*Primary Examiner*—Bruce R. Campell
*Assistant Examiner*—Bao Qun Li
(74) *Attorney, Agent, or Firm*—Harness, Dickey & Pierce, P.L.C.

(57) ABSTRACT

A highly immunoreactive viral peptide, pE2, is disclosed which is derived from the carboxy-terminal end region of ORF2 region of the hepatitis E virus (HEV) genome. A unique feature of the novel pE2 peptide is that it possesses conformational antigenic determinants which are only exposed when monomers of the peptide associate with one another through non-covalent interactions to naturally form homodimers. The novel pE2 peptide is proven to be highly reactive with sera from patients having current or past infection with HEV which suggests that the homodimer may mimic certain structural features of the HEV capsid protein. Furthermore, the antigenic activity of the pE2 peptide is strictly conformational in nature and therefore, exhibits immunochemical reactivity only when the peptide exists in a dimeric form. Consequently, the antigenic activity is lost upon dissociation of the dimers, but the activity is restored when the monomers reassociate to form dimers. Moreover, diagnostic methods useful in detecting and diagnosing HEV infection, and the use of a vaccine composition effective in preventing hepatitis E virus infection in which the novel pE2 peptide is utilized are also disclosed.

15 Claims, 24 Drawing Sheets

```
                    v10        v          v          v          v
ORF2 5147 ATGCGCCCTCGGCCTATTTTGCTGTTGCTCCTCATGTTTCTGCCTATGCT v60        v          v          v          v
ORF2 5197 GCCCGCGCCACCGCCCGGTCAGCCGTCTGGCCGCCGTCGTGGGCGGCGCA v110       v          v          v          v
ORF2 5247 GCGGCGGTTCCGGCGGTGGTTTCTGGGGTGACCGGGTTGATTCTCAGCCC v160       v          v          v          v
ORF2 5297 TTCGCAATCCCCTATATTCATCCAACCAACCCCTTCGCCCCCGATGTCAC v210       v          v          v          v
ORF2 5347 CGCTGCGGCCGGGGCTGGACCTCGTGTTCGCCAACCCGCCCGACCACTCG v260       v          v          v          v
ORF2 5397 GCTCCGCTTGGCGTGACCAGGCCCAGCGCCCCGCCGTTGCCTCACGTCGT v310       v          v          v          v
ORF2 5447 AGACCTACCACAGCTGGGGCCGCGCCGCTAACCGCGGTCGCTCCGGCCCA v360       v          v          v          v
ORF2 5497 TGACACCCCGCCAGTGCCTGATGTTGACTCCCGCGGCGCCATCCTGCGCC v410       v          v          v          v
ORF2 5547 GGCAGTATAACCTATCAACATCTCCCCTTACTTCTTCCGTGGCCACCGGT v460       v          v          v          v
ORF2 5597 ACAAACTTGGTTCTATACGCCGCTCCTCTTAGCCCACTTCTACCCCTCCA v510       v          v          v          v
ORF2 5647 GGACGGCACCAATACTCATATAATGGCCACAGAAGCTTCTAATTATGCCC v560       v          v          v          v
ORF2 5697 AGTACCGGGTTGCTCGTGCCACAATTCGCTACCGCCCGCTGGTCCCCAAC v610       v          v          v          v
ORF2 5747 GCTGTTGGTGGCTACGCCATCTCCATCTCGTTCTGGCCACAGACCACCAC v660       v          v          v          v
ORF2 5797 CACCCCGACGTCCGTTGACATGAATTCAATAACCTCGACGGATGTTCGTA v710       v          v          v          v
ORF2 5847 TTTAGTCCAGCCCGGCATAGCCTCCGAGCTTGTTATCCCAAGTGAGCGC
```

Figure 2A

```
                v760      v         v         v         v
ORF2 5897 CTACACTACCGTAACCAAGGTTGGCGCTCTGTTGAGACCTCCGGGGTGGC v810      v         v         v         v
ORF2 5947 GGAGGAGGAGGCCACCTCTGGTCTTGTTATGCTCTGCATACATGGCTCAC v860      v         v         v         v
ORF2 5997 CTGTAAATTCTTATACTAATACACCTTATACCGGTGCCCTCGGGCTGTTG v910      v         v         v         v
ORF2 6047 GACTTTGCCCTCGAACTTGAGTTCCGCAACCTCACCCCCGGTAATACCAA v960      v         v         v         v
ORF2 6097 CACGCGGGTCTCCCGTTACTCCAGCACTGCCCGTCACCGCCTTCGTCGCG v1010     v         v         v         v
ORF2 6147 GTGCAGATGGGACTGCCGAGCTTACCACCACGGCTGCTACCCGCTTCATG v1060     v         v         v         v
ORF2 6197 AAGGACCTCTATTTTACTAGTACTAATGGTGTCGGTGAGATCGGCCGTGG v1110     v         v         v         v
ORF2 6247 GATAGCGCTTACCCTGTTTAACCTTGCTGACACCCTGCTTGGCGGTCTAC v1160     v         v         v         v
ORF2 6297 CGACAGAATTGATTTCGTCGGCTGGTGGCCAGCTGTTCTACTCTCGTCCC
                                       :::::::::::::::::::::
E2      1                              CAGCTGTTCTACTCTCGTCCC v1210     v         v         v         v
ORF2 6347 GTCGTCTCAGCCAATGGCGAGCCGACTGTTAAGCTTTATACATCTGTAGA
          ::::::::::::::::::::::::::::::::::::::::::::::::::
E2     22 GTCGTCTCAGCCAATGGCGAGCCGACTGTTAAGCTTTATACATCTGTAGA v1260     v         v         v         v
ORF2 6397 GAATGCTCAGCAGGATAAGGGTATTGCAATCCCGCATGACATCGACCTCG
          ::::::::::::::::::::::::::::::::::::::::::::::::::
E2     72 GAATGCTCAGCAGGATAAGGGTATTGCAATCCCGCATGACATCGACCTCG v1310     v         v         v         v
ORF2 6447 GGGAGTCTCGTGTAGTTATTCAGGATTATGACAACCAACATGAGCAGGAC
          ::::::::::::::::::::::::::::::::::::::::::::::::::
E2    122 GGGAGTCTCGTGTAGTTATTCAGGATTATGACAACCAACATGAGCAGGAC
```

Figure 2B

```
              v1360         v           v           v           v
ORF2  6497  CGACCGACACCTTCCCCAGCCCCATCGCGCCCTTTTTCTGTCCTCCGAGC
            ::::::::::::::::::::::::::::::::::::::::::::::::::
E2     172  CGACCGACACCTTCCCCAGCCCCATCGCGCCCTTTTTCTGTCCTCCGAGC v1410         v           v           v           v
ORF2  6547  TAATGATGTGCTTTGGCTTTCTCTCACCGCTGCCGAGTATGACCAGTCCA
            ::::::::::::::::::::::::::::::::::::::::::::::::::
E2     222  TAATGATGTGCTTTGGCTTTCTCTCACCGCTGCCGAGTATGACCAGTCCA v1460         v           v           v           v
ORF2  6597  CTTACGGCTCTTCGACCGGCCCAGTCTATGTCTCTGACTCTGTGACCTTG
            ::::::::::::::::::::::::::::::::::::::::::::::::::
E2     272  CTTACGGCTCTTCGACCGGCCCAGTCTATGTCTCTGACTCTGTGACCTTG v1510         v           v           v           v
ORF2  6647  GTTAATGTTGCGACCGGCGCGCAGGCCGTTGCCCGGTCACTCGACTGGAC
            ::::::::::::::::::::::::::::::::::::::::::::::::::
E2     322  GTTAATGTTGCGACCGGCGCGCAGGCCGTTGCCCGGTCACTCGACTGGAC v1560         v           v           v           v
ORF2  6697  CAAGGTCACACTTGATGGTCGCCCCCTTTCCACCATCCAGCAGTATTCAA
            ::::::::::::::::::::::::::::::::::::::::::::::::::
E2     372  CAAGGTCACACTTGATGGTCGCCCCCTTTCCACCATCCAGCAGTATTCAA v1610         v           v           v           v
ORF2  6747  AGACCTTCTTTGTCCTGCCGCTCCGCGGTAAGCTCTCCTTTTGGGAGGCA
            ::::::::::::::::::::::::::::::::::::::::::::::::::
E2     422  AGACCTTCTTTGTCCTGCCGCTCCGCGGTAAGCTCTCCTTTTGGGAGGCA v1660         v           v           v           v
ORF2  6797  GGTACTACTAAAGCCGGGTACCCTTATAATTATAACACCACTGCTAGTGA
            ::::::::::::::::::::::::::::::::::::::::::::::::::
E2     472  GGTACTACTAAAGCCGGGTACCCTTATAATTATAACACCACTGCTAGTGA v1710         v           v           v           v
ORF2  6847  CCAACTGCTCGTTGAGAATGCCGCTGGGCATCGGGTTGCTATTTCCACTT
            ::::::::::::::::::::::::::::::::::::::::::::::::::
E2     522  CCAACTGCTCGTTGAGAATGCCGCTGGGCATCGGGTTGCTATTTCCACTT v1760         v           v           v           v
ORF2  6897  ACACCACTAGCCTGGGTGCTGGTCCCGTCTCTATTTCCGCGGTTGCTGTT
            ::::::::::::::::::::::::::::::::::::::::::::::::::
E2     572  ACACCACTAGCCTGGGTGCTGGTCCCGTCTCTATTTCCGCGGTTGCTGTT
```

Figure 2C

```
             v1810        v            v            v            v
ORF2 6947 TTAGCCCCCCACTCCGCGCTAGCATTGCTTGAGGATACCATGGACTACCC
          ::::::::::  ::::::::: :::::::::::::::::::::::::::::::
E2    622 TTAGCCCCCC-CTCCGCGCTAGCATTGCTTGAGGATACCATGGACTACCC
                             Stop code v1860        v            v            v            v
ORF2 6997 TGCCCGCGCCCATACTTTCGATGACTTCTGCCCGGAGTGCCGCCCCCTTG
          :::::::::::::::::::::::::::::::::::::::::::::::::
E2    672 TGCCCGCGCCCATACTTTCGATGACTTCTGCCCGGAGTGCCGCCCCCTTG v1910        v            v            v            v
ORF2 7047 GCCTCCAGGGCTGTGCTTTTCAGTCTACTGTCGCTGAGCTTCAGCGCCTT
          :::::::::::::::::::::::::::::::::::::::::::::::::
E2    722 GCCTCCAGGGCTGTGCTTTTCAGTCTACTGTCGCTGAGCTTCAGCGCCTT
                                        End of ORF2
             v1960        v            v ↓          v            v
ORF2 7097 AAGATGAAGGTGGGTAAAACTCGGGAGTTATAGTTTATTTGCTTGTGCCC
          :::::::::::::::::::::::::::::::::::::::
E2    772 AAGATGAAGGTGGGTAAAACTCGGGAGTTATAGTTTATTT v2010        v            v            v            v
ORF2 7147CCCTTCTTTCTGTTGCTTATTTCTCTTTTCTGCGTTCCGCGCTCCCTGAAA

ORF2 7197 AAA
```

Figure 2D

```
              v10        v           v           v           v
ORF3  5106  ATGAATAACATGTCTTTTGCTGCGCCCATGGGTTCGCGACCATGCCCCT v60        v           v           v           v
ORF3  5156  CGGCCTATTTTGCTGTTGCTCCTCATGTTTCTGCCTATGCTGCCCGCGCC v110       v           v           v           v
ORF3  5206  ACCGCCCGGTCAGCCGTCTGGCCGCCGTCGTGGGCGGCGCAGCGGCGGTT v160       v           v           v           v
ORF3  5256  CCGGCGGTGGTTTCTGGGGTGACCGGGTTGATTCTCAGCCCTTCGCAATC v210       v           v           v           v
ORF3  5306  CCCTATATTCATCCAACCAACCCCTTCGCCCCCGATGTCACCGCTGCGGC v260       v           v           v           v
ORF3  5356  CGGGGCTGGACCTCGTGTTCGCCAACCCGCCCGACCACTCGGCTCCGCTT
            ::::::::::::::::::::::::::::::::::::::::::::
E3       1              GACCTCGTGTTCGCCAACCCGCCCGACCACTCGGCTCCGCTT v310       v           v           v           v
ORF3  5406  GGCGTGACCAGGCCCAGCGCCCCGCCGTTGCCTCACGTCGTAGACCTACC
            ::::::::::::::::::::::::::::::::::::::::::::::::::
E3      51  GGCGTGACCAGGCCCAGCGCCCCGCCGTTGCCTCACGTCGTAGACCTACC v360        v
ORF3  5456  ACAGCTGGGGCCGCGCCGCTAA
            ::::::::::::::::::::::
E3     101  ACAGCTGGGGCCGCGCCGCTAA
```

Figure 3

```
              v10         v          v          v          v
pE2   1  QLFYSRPVVSANGEPTVKLYTSVENAQQDKGIAIPHDIDLGESRVVIQDY v60         v          v          v          v
pE2  51  DNQHEQDRPTPSPAPSRPFSVLRANDVLWLSLTAAEYDQSTYGSSTGPVY v110        v          v          v          v
pE2 101  VSDSVTLVNVATGAQAVARSLDWTKVTLDGRPLSTIQQYSKTFFVLPLRG v160        v          v          v          v
pE2 151  KLSFWEAGTTKAGYPYNYNTTASDQLLVENAAGHRVAISTYTTSLGAGPV v210
pE2 201  SISAVAVLAPPPR
```

Figure 4

```
              v              v           v
pE3   1  DLVFANPPDHSAPLGVTRPSAPPLPHVVDLPQLGPRR.
```

Figure 5

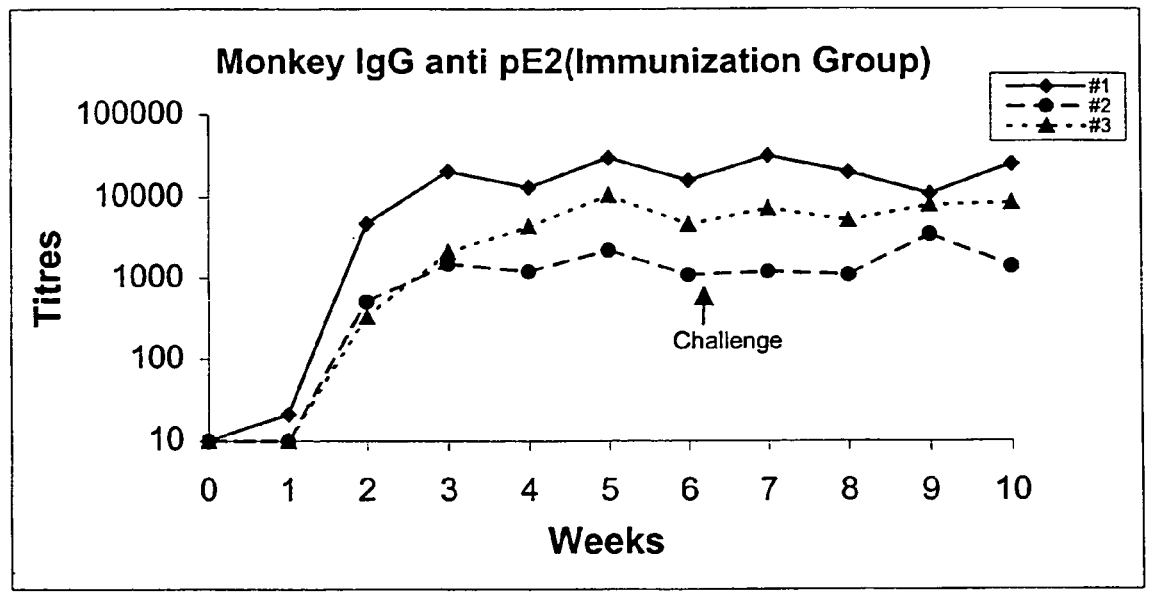
A
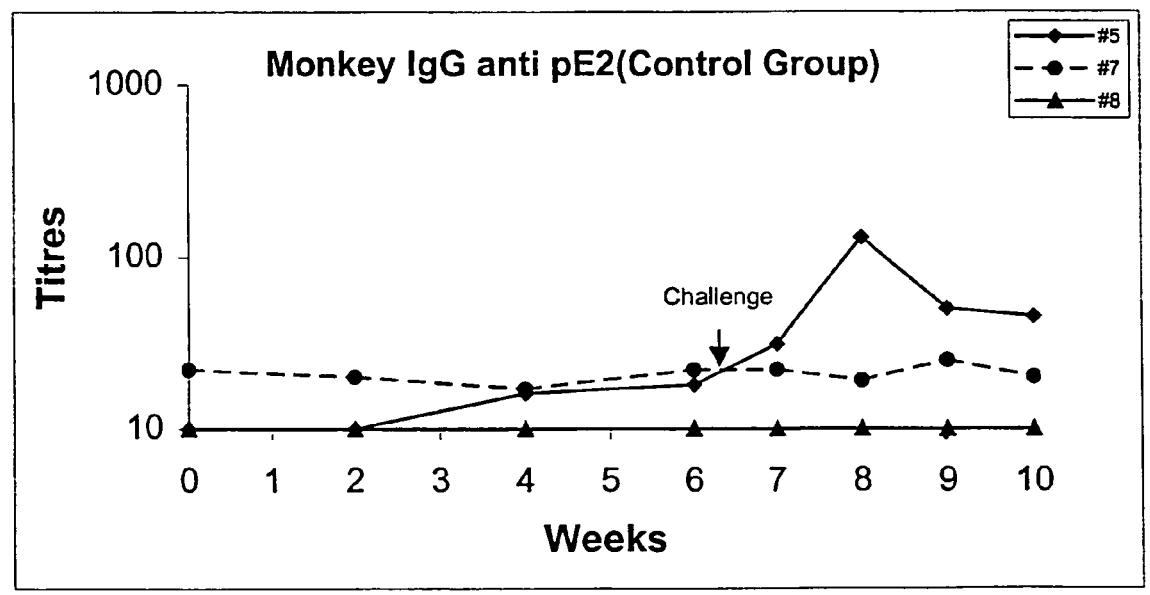
B
Figure 18

HEV ANTIGENIC PEPTIDE AND METHODS

FIELD OF THE INVENTION

The present invention relates to a highly immunoreactive viral peptide, pE2, cloned from the genome of a Chinese strain of hepatitis E virus (HEV) and its utilization in the development of reliable diagnostic methods for the detection and diagnosis of HEV, as well as its use in a vaccine composition for the prevention of HEV in humans.

BACKGROUND OF THE INVENTION

Hepatitis E virus (HEV) was first discovered in 1983 as a cause of enterically transmitted hepatitis (Balayan et al., 1983). The full length viral genome was first cloned and sequenced in 1991, and it was found to be a single-stranded positive sense unenveloped RNA (Tam et al., 1991). Although morphologically resembling members of the Caliciviridae (Bradley et al., 1988; Huang et al., 1992; Panda et al., 1989), it has a distinct genomic organization (Berke et al., 1997). Based on sequence analysis, the 7.2 kb viral genome is predicted to contain three open reading frames (ORF) (FIG. 1) (Tam et al., 1991; Aye et al., 1992; Aye et al., 1993; Huang et al., 1992; Reyes et al., 1993). Non-structural viral proteins are encoded as a polyprotein by ORF1 located at the 5' terminus of the viral genome. ORF2 is located at the 3' end of the genome and encodes a major structural protein. The 5' end of ORF3 has one base overlapping with the 3' end of ORF1 and the 3' end has 339 bases overlapping with the 5' end of ORF2. ORF3 is believed to code for another structural protein whose function is still unknown. Linear antigenic epitopes have been located in ORF2 and ORF3 by epitope mapping and study of recombinant peptides (Coursaget et al., 1993; Khudyakov et al., 1993; Khudyakov et al., 1994).

Recent studies have shown that truncated recombinant peptides derived from both the amino and carboxy-termini of the major HEV structural protein of the ORF2 region can self-assemble into virus-like particles (Li et al., 1997). Although smaller in size, these virus-like particles were morphologically and antigenically similar to the capsid protein of the infectious virus (Li et al., 1997; Xing et al., 1999). Based on these findings, it would appear that the assembly of the recombinant peptide into the virus-like particles may have similar requirements as the assembly of the full length HEV structural protein into the larger capsid of the infectious virus particles. Notably, these findings suggest that the ORF2 encoded structural protein alone may be sufficient to self-assemble into the virus capsid. Moreover, it would appear that the interactions involved in the formation of the capsid protein per se may occur within a domain of the full length ORF2 protein from amino acid residues 112 to 608 (Xing et al., 1999). With a high isoelectric point of 12.35, the 111 amino acid long sequence located at the amino terminal domain of the major structural protein is believed to be involved in packaging of the viral genome (Briton and Heinz, 1990), however this domain evidently does not directly participate in the assembly of the virus capsid per se. The carboxy-terminal domain of the major structural protein also does not directly participate in the assembly of the virus capsid, however Li et al. (1997) have shown that appropriate proteolytic cleavage of this domain was essential for the assembly of virus-like particles.

Hepatitis E principally occurs in developing countries in both epidemic and sporadic forms. Several large outbreaks of hepatitis E occurred in the 1950's to 1980's caused by sewage-polluted drinking water (Visvanathan, 1957; Wong et al., 1980; Myint et al., 1985; Belabbes et al., 1985; Hau et al., 1999). The infection is usually self-limiting, but there are reports of serious complications when infection occurs during pregnancy (Tsega et al., 1992; Dilawari et al., 1994; Hussaini et al., 1997). One important preventive strategy employed in the combat against viral infection is the monitoring and detection of HEV in environmental specimens to ensure public health safety and environmental protection. However, traditional methods presently utilized for collecting and concentrating virus particles have several well known disadvantages that limit the investigation and discovery of a potential source of HEV. Two of the most common methods presently utilized are adsorption and centrifugation.

In the adsorption method, viruses are first concentrated from a test sample by adsorption to microporous filters and then eluted with large volumes of eluent. However, this technique also effectively concentrates a variety of other solutes, such as humic acids and proteins, which may interfere with the detection of viruses. In particular, many naturally occurring inorganic and organic solutes inhibit the nucleic acid polymerases useful in the amplification of target genomes (e.g. reverse transcriptase and Taq polymerase) (Tsai et al., 1992; 1993). The likelihood of nucleases and proteases being present in the test sample may degrade virus genomes before they can be amplified and therefore, contribute to an ambiguous result. In addition, various proteins, carbohydrates, and other organic compounds may bind magnesium ions and nucleotides necessary for the proper function of nucleic acid polymerases, while other solutes may exhibit toxic effects that could ultimately damage these polymerases (Demeke and Adams, 1992; Imai et al., 1992; Kolk et al., 1992).

In the centrifugation method, the test sample is homogenized and then centrifuged repeatedly. During the process, polyethylene glycol (PEG) is added to the supernatant and then centrifuged again. The final pellet is resuspended in buffer, however the final concentrate still contains toxic substances which may interfere with subsequent stages of the diagnostic method such as cell culturing, reverse transcription and polymerase chain reaction (Beril et al., 1996). As a consequence, it is necessary that the concentrate derived from the test sample undergo detoxification by gel filtration on a sephadex column.

Another important strategy useful in the fight against viral infection is the utilization of a vaccine for immunization against HEV to ensure public health safety and protection. However, it has not hitherto been possible to develop a vaccine against HEV infection using live attenuated or killed viral particles because of the difficulty in propagating the virus in cultured cells. As an alternative solution, it has been shown that some recombinant HEV peptides, especially those derived from the structural genes of the viral genome, are more promising in providing protection against contracting HEV (Tsarev et al., 1994a; Tsarev et al., 1997). Advantages to using recombinant peptides in vaccine formulations, compared to attenuated viruses, are that peptides can be more efficiently produce and conveniently purified. Furthermore, there is no possibility that the resulting vaccine will contain any live intact virus particles, thereby avoiding a potential risk of infectivity.

In view of the above comments, there remains a need for a reliable method of determining and diagnosing HEV which will not only avoid the disadvantages previously described, but also provide a more sensitive analytical test for detecting HEV in biological and environmental specimens. According to the present invention, there is provided a diagnostic method employing a highly immunoreactive recombinant viral peptide, pE2, derived from the carboxy-terminal end region of ORF2 of the hepatitis E virus (HEV) genome, which is proven to be highly reactive with sera from patients having current or past infection with HEV. Moreover, the pE2 peptide is antigenically related to the hepatitis E virus since part of its amino acid sequence is highly conserved among other HEV isolates. As described and further demonstrated herein, the antigenic properties of the pE2 peptide makes it an excellent candidate as a vaccine for the immunization and prevention of HEV infection. Accordingly, diagnostic methods useful in detecting HEV infection and a vaccine composition effective in preventing hepatitis E virus infection in which the novel pE2 peptide is utilized are provided herein.

SUMMARY OF THE INVENTION

An object of the present invention is to provide a hepatitis E virus (HEV) peptide, pE2, which is highly immunoreactive with sera from individuals infected with the hepatitis E virus due to the presence of conformational antigenic determinants that are only exposed following dimerization of pE2 monomers to form homodimers.

Another object of the invention to provide an improved and more reliable diagnostic method for determining current and past infection of HEV through the detection of IgM and IgG antibodies in a clinical or biological test sample, which incorporates the pE2 dimer as an immunoreagent due to its high specificity and sensitivity of binding to HEV antibodies.

Still another object of the present invention is to provide an improved and more reliable diagnostic method for monitoring and detecting HEV in public health and environmental studies using antibodies specifically raised against the pE2 dimer that can effectively capture, isolate and concentrate HEV particles in a test sample, and which avoids disadvantages associated with the use of other conventional methods.

Yet another object of the invention is to provide a vaccine composition which comprises the pE2 dimer, and its use thereof, for the immunization and prevention of HEV infection.

As shown in Table 1, although the percentage of nucleotide sequence homology may vary from between 77% and 100% among different HEV isolates, these changes are generally conservative in nature, as signified by the high percentage of amino acid sequence homology. Conservation within the HEV genome as revealed among the different isolates of HEV implies that (1) the pE2 peptide may be an important functional domain of the structural protein of HEV, (2) diagnostic tests incorporating the pE2 peptide are likely to be advantageous in detecting different isolates of HEV, and (3) a vaccine prepared from the pE2 peptide is likely to afford protection against different HEV isolates.

TABLE 1

A Conserved Region of the HEV Major Structural Protein

| Strain | Region | Sequence Homology (%) | | Reference |
|---|---|---|---|---|
| | | Nucleotide | Amino Acid | |
| D11092 | China | 100 | 100 | Aye et al., 1992 |
| D10330 | China | 92.6 | 98.6 | Aye et al., 1993 |
| D25547 | China | 94.1 | 99.5 | Yin et al., 1994 |
| M73218 | Burma | 92.9 | 100 | Tam et al., 1991 |

TABLE 1-continued

A Conserved Region of the HEV Major Structural Protein

| Strain | Region | Sequence Homology (%) | | Reference |
|---|---|---|---|---|
| | | Nucleotide | Amino Acid | |
| M74506 | Mexican | 78.2 | 94.3 | Purdy et al., 1999 |
| M80581 | Pakistani | 98.3 | 100 | Tsarev et al., 1992 |
| M94177 | China | 98.6 | 99.5 | Bi et al., 1994 |
| X98292 | India | 89.7 | 99 | Donati et al., 1997 |
| M74506 | Mexican | 78.2 | 94.3 | Huang et al., 1992 |
| AF035437 | USA | 76.7 | 92.9 | Schlauder et al., 1998 |

According to the present invention there is provided a highly immunoreactive viral peptide, pE2, which is derived from the carboxyl terminal end region of ORF2 of the hepatitis E virus (HEV) genome and comprises an amino acid sequence identified as SEQ I.D. NO: 2. A special feature of the pE2 peptide is that it possesses conformational antigenic determinants which are only exposed as a result of non-covalent interactions between monomers of the peptide to naturally form homodimers. Moreover, the cloning and expression of the highly immunoreactive structural pE2 peptide, as well as its purification and characterization are described herein.

The HEV peptide, pE2, of the present invention is derived from the domain of the HEV major structural protein described previously, which directly participates in the assembly of the virus capsid. Translated from the carboxyl domain of the ORF2 nucleotide sequence, the pE2 peptide was originally predicted to be 267 amino acid residues in length corresponding to the carboxyl domain of the full length protein. Based on similar peptide mapping studies (Khudyakov et al., 1993; Khudyakov et al., 1994), it was also expected that the peptide would contain linear epitopes at both its amino and carboxy-termini. However, a frameshift mutation in the cloned sequence caused translation to terminate prematurely at a new termination codon located upstream from the original cDNA sequence giving rise instead to a smaller peptide of only 213 amino acid residues in length (FIG. 2).

Characterization of the pE2 peptide showed a truncation at its carboxy-terminus which has effectively removed the carboxyl domain that inhibits self-assembly of the virus-like particles. Consequently, the pE2 peptides interact with one another as monomers through dimerization, thereby naturally occurring as homodimers. Furthermore, the pE2 peptide is strongly recognized in its dimeric form by HEV reactive human sera which suggests that the homodimer may mimic certain structural features of the HEV capsid protein. Therefore, it is the conformational antigenic determinants brought about by the dimerization of the pE2 peptide which serves to distinguish it from other bacterially expressed HEV peptides reported by other investigators (Yarbough et al., 1991; Purdy et al., 1992; Li et al., 1994; Li et al., 1997). While the antigenic activity of previously reported HEV peptides has been attributed primarily to the presence of linear epitopes contained within their respective primary structures, the antigenic activity of the pE2 peptide of the present invention is largely related to the quarternary structure of the homodimers. Accordingly, the antigenic domain of the pE2 peptide is distinctly different from previously identified linear epitopes defined within the amino terminal domain of the ORF2 region because no other similar conformational antigenic determinants has been previously described or predicted by peptide mapping.

As demonstrated and described herein, two different types of antigenic activity are exhibited by the novel pE2 peptide. The first type of antigenic activity is associated with the monomeric form of the pE2 peptide which is a similar type of activity associated with other bacterially expressed HEV antigenic peptides described to date (Yarbough et al., 1991; Purdy et al., 1992; Li et al., 1994). This type of antigenic activity is primarily attributed to linear epitopes located to the primary structure of the respective peptides, although the activity may be influenced by secondary and tertiary structures corresponding to various configurations assumed by the respective peptides in aqueous solution (Li et al., 1997). However, the second and more salient antigenic activity exhibited by the pE2 peptide is associated with the dimeric form of the peptide and which was discovered to be more highly immunoreactive than its monomeric form. Experimental studies show that the levels of antibody reactive against the pE2 dimer present in HEV reactive human sera was frequently observed at much higher levels than for antibody reactive against the pE2 monomer. This new type of antigenic activity, which has hitherto never been described, is largely attributed to the new conformational antigenic determinants inherent to the pE2 homodimer. Moreover, the antigenic activity was abrogated upon dissociation of the dimer and the activity was reconstituted once the monomers had reassociated to form dimers. This behavior illustrates that the antigenic activity associated with the conformational antigenic determinants is related to the dimeric form, or quarternary structure, of the pE2 peptide brought about by non-covalent interactions between pE2 monomers to form homodimers.

E2 DNA Sequence

According to one aspect of the present invention there is provided a purified nucleic acid molecule, E2, which encodes the conformational peptide, pE2, and which comprises the cDNA sequence identified as SEQ I.D. NO: 1, and any homologous sequence or fragment thereof.

The nucleotide sequence, E2, was originally isolated from the carboxy-terminal end of the ORF2 region of the hepatitis E virus (HEV) genome of the Chinese strain D11092 of HEV (FIG. 2). The original cloned sequence, comprising 811 base pairs in length and spanning positions 6326 to 7136 with a stop codon located at positions 7127 to 7129, had inadvertently contained a single base pair deletion at position 6957, presumably due to a PCR amplification error (FIG. 2). The resulting frameshift mutation caused translation of the nucleotide sequence to terminate prematurely at a new stop codon (positions 6966 to 6968). Subsequent translation of the nucleic acid sequence led to the generation and discovery of the novel pE2 peptide and the novel E2 nucleotide sequence (i.e. SEQ ID NO: 1) encoded therefrom comprising 642 base pairs. Accordingly, with reference to FIG. 2, the novel E2 nucleotide sequence spans positions 6326 to 6968 wherein a fragment of the sequence located downstream of the new stop codon after position 6968 is removed and a single base pair deletion occurs at position 6957.

It will be appreciated by those skilled in the art that due to the degeneracy of the genetic code, more than one codon may code for any given amino acid residue of the sequence represented by SEQ ID NO: 2 (i.e. pE2), thereby resulting in a wide variety of nucleic acid sequences in addition to SEQ ID NO: 1 (i.e. E2) that may be generated and which will also encode the pE2 peptide. Accordingly, the invention contemplates each and every possible variation of nucleotide sequence that could be made by selecting combinations based on possible codon choices, including the complementary nucleic acid sequence for SEQ ID NO: 1. These combinations are made in accordance with the standard triplet genetic code as applied to the nucleic acid sequence of the pE2 peptide, and all such variations are to be considered as being specifically disclosed.

Moreover, a variety of pE2 peptide derivatives or antigenic equivalents may be made, including for example, various substitutions, insertions, deletions, or extensions, the net result of which do not alter the immunochemical reactivity of the pE2 peptide. Therefore, nucleic acid sequences that code for immunologically active derivatives of the pE2 peptide are also contemplated as being part of the present invention. Methods for making such derivatives may be readily accomplished by one of ordinary skill in the art (Sambrook et al., Molecular Cloning: A Laboratory Manual, $2^{nd}$ Ed., Cold Spring Harbor Laboratory Press, Plainview, N.Y., 1989). In accordance with the present invention, any nucleic acid sequence which encodes the amino acid sequence of the pE2 peptide, or antigenic equivalents, can be used to generate recombinant molecules which express pE2.

pE2 Amino Acid Sequence

According to another aspect of the present invention, there is provided a conformational HEV peptide antigen, pE2, comprising an amino acid sequence represented by SEQ ID NO: 2 or a homologous sequence, fragment, or analog thereof.

It is well established that the information for determining the three-dimensional structure of a polypeptide is carried entirely within its amino acid sequence. Moreover, portions of the sequence comprising amino acids that define specific conformational epitopes can be widely dispersed with intervening sequences along the length of the molecule. Based on the predicted tertiary (and quarternary) structure of the polypeptide, the three-dimensional coordinates of the conformational epitopes are eventually brought into their correct configuration due to the three-dimensional folding of the polypeptide's primary structure. Accordingly, it is expected that the amino acid sequence can be subject to a certain degree of modification based on the higher level of structural organization of the polypeptide which will not alter the conformational structure and immunochemical reactivity of the epitope substantially. Therefore, segments of the polypeptide located between groups of residues defining the various epitopes may not critically alter the presentation of the epitope following extension, deletion, insertion, or substitution of residues within these intervening sequences.

Moreover, depending on the chemical properties of the amino acid residues contained within a sequence which defines a particular epitope, substitutions with residues having similar functional groups may not alter the immunochemical reactivity of the epitope. In this regard, it is expected that as long as the immunochemical reactivity of the pE2 peptide is preserved so that it remains recognizable by anti-pE2 antibodies, various amino acid residues in the amino acid sequence may be deleted, inserted or substituted by other amino acid residues, to generate derivatives. This is providing, of course, that the particular change incorporated provides an advantage in its use, such as in dealing with strain-to-strain variations among different isolates of HEV (Table 1). Furthermore, amino acid substitutions which are contemplated within the scope of the invention are those in which the chemical nature of the substitute residue is similar to that of the original amino acid. Amino acids are generally considered to possess similar chemical properties based on their functional group and therefore, include combinations such as: Gly/Ala; Asp/Glu; Asn/Gln; Val/Ile/Leu; Ser/Thr; Lys/Arg; and Phe/Tyr. These derivatives of the pE2 peptide may therefore comprise extensions, substitutions, insertions and/or deletions of the amino acid sequences defined by SEQ ID NO: 2, providing their immunochemical reactivity to HEV antibodies is preserved. Two peptides are said to have equivalent immunochemical reactivity and within the scope of this invention when they are capable of being recognized by the same antibodies raised against the pE2 peptide.

Generating the pE2 Peptide

The pE2 peptide of the present invention can be generated by methods known in the art that provide the conformational epitopes of interest, including chemical synthetic methods and recombinant DNA technology. A preferred method of preparing the pE2 peptide is through recombinant DNA expression in a host cell followed by isolation and purification of the peptide. In accordance with the present invention, nucleic acid sequences which encode the pE2 peptide, fragments of the peptide, fusion proteins or functional equivalents thereof, may be used in recombinant DNA molecules that direct the expression of pE2 in appropriate host cells. In order to express an immunologically active pE2 peptide, the nucleotide sequence encoding pE2 (i.e. SEQ ID NO: 1), or its functional equivalent, is inserted into an appropriate expression vector which contains the necessary elements for the transcription and translation of the inserted coding sequence. Depending on the host cell selected, the expression vector will normally contain control elements of DNA that effect expression of the DNA sequence and usually include a promoter, ribosome binding site, translational start and stop sites, and a transcriptional termination site.

Therefore, according to yet another aspect of the present invention, there is provided a method for preparing the pE2 peptide of the present invention which comprises isolating the cDNA sequence from the HEV genome, inserting the cDNA sequence into an expression vector such that it is capable of being expressed in an appropriate host cell, transforming the host cell with the expression vector, culturing the transformed host cell, and isolating and purifying the pE2 peptide.

Methods which are well known to those skilled in the art can be used to construct expression vectors containing the pE2 coding sequence and appropriate transcriptional or translational controls. The desired cDNA sequence obtained as described above may be inserted into an expression vector using known and standard techniques (Sambrook et al., 1989 and Ausubel et al., 1989). The expression vector is normally cut using restriction enzymes and the cDNA sequence is inserted using blunt-end or staggered-end ligation. The cut is usually made at a restriction site in a convenient position in the expression vector such that, once inserted, the cDNA sequences are under the control of the functional elements of cDNA that effect its expression. Transformation and culturing of an host cell and isolation of the peptide as required may also be carried out using standard techniques.

In bacterial systems, a number of expression vectors may be selected depending upon the use intended for the peptide or protein to be expressed. For example, when large quantities of a peptide or protein are needed for the production of antibodies, vectors which direct high level expression of fusion proteins that are readily purified may be desired. According to a related aspect of the present invention, there is provided an expression vector containing the nucleic acid sequence, E2, identified by SEQ ID NO:1 which codes for the pE2 peptide and which vector is capable of expressing the nucleic acid sequence, E2. The expression vector is suitable for expression in a bacterial system, preferably *E. coli*, and includes, but is not limited to the multifunctional *E. coli* cloning and expression vector pGEX (Promega, Madison, Wis.). In this particular vector, the pE2 coding sequence is ligated, at its 5'-end, into the vector in frame with the heterologous sequence for the glutathione S-transferase (GST), at its 3'-end, and the resulting hybrid polynucleotide sequence expressed as a fusion protein. In general, such fusion proteins are soluble and can easily be purified from lysed cells by adsorption to glutathione-agarose beads followed by elution in the presence of free glutathione. Proteins made in such systems are designed to include cleavage sites so that the cloned peptide of interest can be released from the GST moiety by adding the appropriate protease, such as thrombin.

Therefore, according to a preferred embodiment of the present invention, there is provided a plasmid that expresses the fusion protein, GE2, comprising the HEV peptide, pE2 identified by SEQ ID NO: 2, which is fused to the glutathione-S-transferas (GST) polypeptide. The E2 nucleic acid sequence, represented by SEQ ID NO: 1, is inserted into a $pGEX_{20}$ expression vector such that the open reading frame of the E2 nucleotide sequence is in frame with the GST open reading frame. The plasmid of the invention comprised the 811 base pair sequence located at positions 6326 to 7136 (FIG. 2) with a stop codon located at positions 7127 to 7129. However, a single base pair deletion at position 6957, presumably due to a PCR amplification error had, in turn, resulted in a frameshift mutation that caused translation of the nucleotide sequence to terminate prematurely at a new stop codon (positions 6966 to 6968) resulting in the generation of the novel pE2 peptide. Accordingly, the novel E2 sequence spans positions 6326 to 6968 with a single base pair deletion at position 6957, and the fragment located downstream of the new stop codon after position 6968 removed (FIG. 2). The cloned E2 sequence, which encodes for the novel pE2 peptide, has 642 base pairs and is identified as SEQ ID NO: 1.

GE2 Protein

The isolated fusion protein, GE2, which contains the entire pE2 peptide fused to a full GST polypeptide is approximately 92 kD. However, the GE2 fusion protein of the invention can contain smaller portions of the pE2 peptide that are immunogenic and therefore can be expected to be smaller than 92 kD. The fusion protein, GE2, described herein is engineered to contain a cleavage site located between the pE2 amino acid sequence and the GST, or heterologous, protein sequence so that the pE2 peptide may be cleaved and purified away from the heterologous moiety when bound to a glutathione sepharose-4B column using thrombin. Moreover, in addition to purification and characterization purposes, the GE2 polypeptide is also useful for directing and confirming the expression of the pE2 peptide in appropriate host cells and developing polyclonal antisera or monoclonal antibodies specific to epitopes of the pE2 peptide. In turn, polyclonal antisera or monoclonal antibodies generated by immunizing a mammal with an isolated GE2 polypeptide are beneficial for assaying for the presence of HEV particles in a biological test sample, as described herein.

pE2 as a Diagnostic Reagent

The conformational pE2 peptide provided herein may be employed as an immunoreagent in diagnostic assays used to screen biological test samples for the presence of HEV antibodies and therefore, aid the practitioner or clinician in the detection and diagnosis of HEV infection. Accordingly, the present invention provides methods for immunochemically detecting anti-HEV antibodies in a biological test sample using the pE2 peptide. Essentially, any immunoassay format which is designed to utilize the pE2 as a capture antigen for detecting anti-HEV antibodies may be employed. Methods for performing immunoassays are well known in the art and the present invention is not intended to be limited to any particular immunoassay. Both homogeneous and heterogeneous immunoassays may be used.

In general, a biological test sample suspected of containing HEV antibodies is contacted and incubated with the pE2 peptide for a time and under conditions which allow a reaction to occur. Preferably, the pE2 peptide is attached to a suitable solid support. If HEV antibodies are present in the test sample, they will form an immunological complex (antigen-antibody complex) with the pE2 peptide and become attached to the solid support. As an option, the solid support may be washed with a buffer solution to remove any unbound components which in certain instances, will help to improve the sensitivity of the assay. After washing, the immunological complex is reacted with an indicator reagent and allowed to incubate for a time and under conditions for a second complex to form. Immunological complexes are detected by any of a number of known techniques, depending on the format of the assay. For example, a conjugate of an anti-mammalian immunoglobulin complexed with a label or signal-generating component (e.g. an enzyme) is commonly employed as an indicator reagent. The presence of an immunological complex confirms the presence of antibodies to HEV in the test sample and is determined by measuring the signal generated. As with many indicator reagents, the amount of antibody present is usually proportional to the signal generated. The presence of the immunological complex in the test sample may be detected visually or mechanically using, for example, an automated scanning and interpretation device.

A suitable solid support will depend upon the type of immunoassay format that is performed however, it is desired that the type of support chosen will have reasonable strength and not interfere with the immunoreactivity of the immunological complex, nor the production of a detectable signal from the signal-generating component. Examples of solid supports include the walls of microwells of a reaction tray, test tubes, sheets, plates, slides, beads (e.g. polystyrene or glass), nitrocellulose strips, membranes, microparticles such as latex particles, chips of glass, plastic, and others.

The label or signal-generating component used as a means to detect the formation of an immunological complex will allow visual detection of a precipitate or a color change, visual detection by microscopy, or automated detection by spectrometry, radiometric measurement, or the like. Examples of signal-generating components include colloidal gold, fluorescent compounds, luminescent compounds, a chromogen, radioactive elements, enzymes (e.g. alkaline phosphatase, horseradish peroxidase and beta-galactosidase) and enhancer compounds (e.g. biotin, anti-biotin and avidin).

Accordingly, another aspect of the present invention provides a method for the diagnosis or detection of HEV antibodies present in a biological test sample comprising the following steps:

providing a pE2 peptide comprising the amino acid sequence defined by SEQ ID NO: 2, or a homologous sequence, fragment, or analog thereof, characterized in that the pE2 peptide is preferably immobilized onto a solid support;

contacting and incubating the pE2 peptide with a biological test sample under conditions which allow the formation of an immunological (antigen-antibody) complex between the pE2 peptide and anti-HEV antibodies;

possibly removing unbound components from the resultant mixture;

incubating the resultant mixture with an indicator reagent; and examining the mixture for the presence of the immunological complex, whereby the formation of the immunological complex indicates the presence of antibodies to hepatitis E virus (HEV) in the test sample.

Generating Anti-pE2 Antibodies

It is further demonstrated by the methods and examples described herein that due to the high immunochemical reactivity displayed by the pE2 peptide, antibodies specifically reactive against the pE2 peptide can be generated through techniques well known in the art. Since the conformational antigenic determinants of the pE2 peptide of the present invention mimic similar structural features of the HEV capsid protein, the pE2 peptide is useful for the production of both polyclonal and monoclonal antibodies. Moreover, these antibodies, or fragments thereof, directed against the pE2 peptide are particularly useful in the development of diagnostics tests as valuable immunoreagents for determining HEV infection through isolation and screening of viral particles and/or antigen. Thus, anti-pE2 antibodies can be used in a number of clinical diagnostic procedures including conventional immunoassay formats to detect the presence of HEV antigen in biological samples and immune capture formats in which small samples of HEV virus particles can be isolated and concentrated. (Harlow and Lane, Antibodies: A laboratory Manual, 1988, Cold Springs Harbor Laboratory Press).

If polyclonal antibodies against the pE2 peptide of the present invention are desired, a selected non-human mammalian host (e.g., mouse, rat, sheep, rabbit, goat, etc.) is injected with the peptide, optionally coupled to a carrier, to promote an immune response and the antibody thus produced is subsequently recovered and purified. According to preferred embodiment of the present invention, the mammalian host is immunized with the GE2 polypeptide as described above bearing HEV conformational epitope(s). The GE2 polypeptide is administered in the form of an injectable formulation whereby the GE2 polypeptide is admixed with a physiologically acceptable diluent. Adjuvants, such as Freund's complete or incomplete adjuvant, may be included in the formulation. The formulation is injected into the host over a suitable period of time, plasma samples being taken at appropriate intervals to assay for HEV viral antibody. When an appropriate level of activity is obtained, the host is bled. Antibody is then recovered and purified from the blood plasma using standard procedures, for example, by immunoaffinity chromatography.

Although the polyclonal antibodies of the invention are preferred, a system containing various monoclonal antibodies functioning as a polyclonal system is also within the scope of the present invention. Monoclonal antibodies directed against HEV conformational epitopes can also be readily produced using the GE2 polypeptide of the present invention by one skilled in the art. The general methodology for producing monoclonal antibodies using immortal antibody-producing cell lines, commonly known as hybridomas, is well known. Hybridomas can be created by the fusion of cells which produce anti-pE2 antibody and an immortalizing cell which imparts long-term tissue culture stability to the hybrid cell. In the formation of the hybrid cell line, the first fusion partner, the antibody-producing cell, can be a spleen cell of a non-human mammalian host, such as a mouse or rat, is innoculated with the GE2 polypeptide. After sufficient time has elapsed for the host to mount an antibody response, the antibody-producing cells are removed. Cells of an immortalizing cell line, such as a mouse or rat myeloma cell line, are fused with the antibody-producing cells and the resulting fusions screened to identify a cell line, such as a hybridoma, that secretes the desired monoclonal antibody. The fusion of an antibody-producing cell with an immortal cell can be accomplished by standard procedures (Kohler and Milstein, (1975) Nature (London) 256, 495–497; Kennet, R., (1980) in Monoclonal Antibodies (Kennet et al., Eds. pp. 365–367, Plenum Press, NY). The fused cell line may be cultured and the monoclonal antibody screened and purified for the production of anti-pE2 antibody from the culture media in a similar manner to recovering polyclonal antibody.

Therefore, according to a further aspect of the present invention, there is provided a method for producing a purified antibody against HEV antigen, wherein an effective amount of a conformational HEV peptide, pE2, having an amino acid sequence represented by SEQ ID NO: 2 or a homologous sequence, fragment, or analog thereof, is injected into a non-human mammalian host, and collecting the antibody produced. In a preferred embodiment of the present invention, the recombinant fusion protein, GE2, which contains the amino acid sequence represented by SEQ ID NO: 2 is injected into the non-human mammalian host to generate the desired antibody.

Utilization of Anti-pE2 Antibody as a Capture Reagent

Monoclonal or polyclonal antibodies that have been raised or developed using the pE2 peptide of the present invention can be used in an immunoassay as a capture reagent to detect the presence of HEV capsid protein, or viral particle, in a biological test sample. Essentially, any immunoassay format which is designed to utilize the anti-pE2 antibody as a capture reagent may be employed. Methods for performing immunoassays are well known in the art and the present invention is not intended to be limited to any particular immunoassay.

In general, since the conformational antigenic determinants of the pE2 peptide of the present invention mimic similar structural features of the HEV capsid protein, anti-pE2 antibodies may be employed in immune capture methods to isolate and concentrate HEV viral particles which can subsequently be detected by extracting viral RNA and applying reverse transcriptase polymerase chain reaction (RT-PCR). According to a preferred embodiment of the invention, an immune capture method is provided for the purpose of isolating and concentrating HEV viral particles whereby polystyrene paddles, or other suitable solid absorbent materials, are coated with antisera raised against the pE2 peptide. This method is highly effective in detecting small amounts of the virus in a test sample which is determined by extraction of viral RNA and applying RT-PCR thereon, preferably a nested polymerase chain reaction.

A suitable solid support or absorbent material will depend upon the type of immunoassay format that is performed however, it is desired that the type of support chosen will have reasonable strength and not interfere with the immunoreactivity of the immunological complex. Examples of solid supports include the walls of microwells of a reaction tray, test tubes, sheets, plates, slides, beads (e.g. polystyrene or glass), nitrocellulose strips, membranes, microparticles such as latex particles, chips of glass, plastic, and others.

Accordingly, another aspect of the present invention provides a method for the detection of HEV viral particles (i.e. analyte) in a biological test sample, comprising the following steps:

- providing a purified antibody raised against an pE2 peptide having an amino acid sequence defined by SEQ ID NO: 2, or a homologous sequence, fragment, or analog thereof, characterized in that the anti-pE2 antibody is preferably immobilized onto a solid support;
- contacting and incubating the anti-pE2 antibody with a biological test sample under conditions which allow the formation of a complex between the anti-pE2 antibody and any HEV analyte which may be present in the test sample;
- possibly removing unbound components from the resultant mixture; and
- examining the mixture for the presence of HEV analyte.

Diagnostic Test Kits

The novel HEV peptide, pE2, or the anti-pE2 antibody, described herein will typically be packaged in the form of a diagnostic kit for use in the detection and diagnosis of HEV infection. The kit will normally contain, in a separate container, the pE2 peptide or the anti-pE2 antibody as the immunoreagent. Moreover, depending on the immunoreagent employed and the type of HEV analyte to be detected, the kit may additionally contain positive and negative control samples, an indicator reagent, such as a labeled anti-human antibody and a signal generating reagent (e.g. enzyme substrate in the case of an enzyme label) if the label does not generate a signal directly. As described herein, the term "separate container" refers to any material capable of holding within fixed limits the pE2 peptide or the anti-pE2 antibody of the present invention, as well as other components provided in the diagnostic test kit. Instructions for carrying out the assay will normally be included in the kit. Such instructions generally describe the immunoreagent concentration or at least one assay method parameter such as the relative amounts of immunoreagent and sample to be admixed, time periods for immunoreagent/sample admixtures, temperature, buffer conditions and the like.

If desired, the pE2 peptide or anti-pE2 antibody of the present invention can be typically immobilized to a solid support material by passive adsorption or through covalent linkage in which there are many techniques available that are well known to those skilled in the art. Solid supports advantageous for immobilizing the pE2 peptide or anti-pE2 antibody of the present invention are also well known to those skilled in the art. A suitable support will depend upon the type of immunoassay format that is performed however, it is desired that the type of support chosen will have reasonable strength and not interfere with the immunoreactivity of the immunological complex, nor the production of a detectable signal from the signal-generating component. Examples of solid supports include the walls of microwells of a reaction tray, test tubes, sheets, plates, slides, beads (e.g. polystyrene or glass), nitrocellulose strips, membranes, microparticles such as latex particles, chips of glass, plastic, and others.

The indicator reagent should comprise a label or signal-generating component capable of indicating the formation of an immunological complex by the immunoreagent of the present invention and the captured HEV analyte. The indicator reagent of the diagnostic test kit can be provided in solution, as a liquid dispersion or as a substantially dry power, e.g. in a lyophilized form. Where the indicator reagent utilizes an enzyme as the signal-generating component, the enzyme's substrate can also be provided in a separate container of the diagnostic test kit. Moreover, the label or signal-generating component used as a means to detect the formation of an immunological complex through antigen-antibody binding will allow visual detection of a precipitate or a color change, visual detection by microscopy, or automated detection by spectrometry, radiometric measurement, or the like. Examples of signal-generating components include colloidal gold, fluorescent compounds (e.g. fluorescein and rhodamine), luminescent compounds, a chromogen, radioactive elements, enzymes (e.g. alkaline phosphatase, horseradish peroxidase and beta-galactosidase) and enhancer compounds (e.g. biotin, anti-biotin and avidin).

As an example of a kit for detecting HEV antibody, a predetermined amount of pE2 of the present invention can be immobilized to a microwell of a reaction tray so that it is capable of immunologically binding to incoming HEV antibody. The indicator reagent can be a labeled mammalian anti-human antibody which will recognized and bind to any HEV antibody that may be present in the test sample. The labeled mammalian anti-human antibody can utilize an enzyme as the signal-generating component, and the enzyme's substrate additionally provided if the enzyme does not generate a signal directly.

Vaccine

Presently, it has not yet been possible to produce attenuated HEV vaccines because the virus cannot be successfully propagated in culture. Candidate vaccines being currently developed are recombinant peptides of the major structural protein expressed eukaryotes (Tsarev et al., 1993a; Tsarev et al., 1994a). Advantages to using recombinant peptides in vaccine formulations compared to attenuated viruses are that peptides can be more efficiently produced and conveniently purified. Furthermore, there is no possibility that the resulting vaccine will contain any live intact virus particles, thereby avoiding a risk of infectivity.

The pE2 peptide was found to be more immunogenic in its dimeric form than in its monomeric form. In an experimental study in which antiserum was raised against the pE2 peptide, levels of antibody reactive against the dimer were substantially higher than for those reactive against the monomeric form. Moreover, unlike HEV reactive human sera which exhibited a broad spectrum of HEV antibody specificity, the pE2 antisera had a restricted spectrum of HEV antibody specificity. Notably, however, the pE2 antisera was capable of recognizing and binding HEV particles as evidenced by their ability to effect efficient immune capture of the virus. The antigenic relationship thus established between the dimeric form of the pE2 peptide and the virus is that the pE2 dimer mimics certain structural features of the virus capsid which makes it morphologically and antigenically related to the HEV capsid protein. Accordingly, it is highly probable that the hepatitis E virus capsid and the pE2 peptide share certain common antigenic determinants, more particularly the new conformational antigenic determinants associated with the dimeric form of the pE2 peptide. This contention is consistent with the finding that the dimeric form of the peptide was recognized strongly and commonly by HEV reactive human sera.

In view of the fact that the pE2 homodimer appears to be structurally and antigenically related to the HEV capsid protein, this makes the bacterially expressed peptide appealing as a potential candidate for a vaccine against HEV infection. Moreover, conservation within the HEV genome of different HEV isolates (Table 1) further suggests that while the pE2 peptide is derived from a Chinese isolate, it is also likely to afford protection against other HEV isolates, including the most genetically divergent strains recently isolated from Mexico and the U.S.

Therefore, according to yet another aspect of the present invention, there is provided a vaccine composition comprising the pE2 peptide, identified by SEQ ID NO: 2, or a homologous sequence, fragment, or analog thereof, and a pharmaceutically acceptable carrier, which protects mammals against challenge with hepatitis E virus following immunization.

Moreover, a use of the vaccine for immunizing a individual against infection against hepatitis E virus, wherein the vaccine comprises an immunologically effective amount of the pE2 peptide, in combination with a pharmacologically acceptable carrier, is also provided. Pharmacologically acceptable carriers are well known to those of ordinary skill in the art (Arnon, R. (Ed.) Synthetic Vaccines I:83–92, CRC Press, Inc., Boca Raton, Fla., 1987). They include liquid media suitable for use as vehicles to introduce the peptide into a patient but should not in themselves induce the production of antibodies harmful to the individual receiving the composition. An example of such liquid media is saline solution. Moreover, the vaccine formulation may also contain an adjuvant for stimulating the immune response and thereby enhancing the effect of the vaccine.

An "immunologically effective amount" means that the administration of that amount to a subject, either in a single dose or as part of a series, is effective for treatment, as defined above. This amount varies depending upon the health and physical condition of the subject to be treated, the species of the subject to be treated (e.g. non-human mammal, primate, etc.), the capacity of the subject's immune system to synthesize antibodies, the degree of protection desired, the formulation of the vaccine, the strain of infecting HEV, and other relevant factors. It is expected that the amount will fall in a relatively broad range that can be determined through routine trials.

Vaccines of the present invention may be administered by any convenient method for the administration of vaccines including oral and parenteral (e.g. intravenous, subcutaneous or intramuscular) injection. The treatment may consist of a single dose of vaccine or a plurality of doses over a period of time.

These and other advantages and features of novelty which characterize the invention are pointed out with particularity in the claims annexed hereto and forming a part hereof. For a better understanding of the invention, its advantages, and objects obtained by its use, reference may be made to the accompanying drawings and descriptive matter, in which there is illustrated and described preferred embodiments of the invention.

Although any methods and materials similar or equivalent to those described herein can be used in the practice or testing of the present invention, the preferred methods, devices, and materials are now described.

BRIEF DESCRIPTION OF THE DRAWINGS

In the following description, the invention will be explained in detail with the aid of the accompanying figures which illustrate preferred embodiments of the present invention and in which:

FIGS. 2A to 2D provide the nucleotide sequence for the ORF2 (SEQ ID NO:4) of Chinese HEV strain (DDBJ Accession No. D11092) and the E2 fragment (SEQ ID NO:1, which sequence is shown continuing with nt1823-1990 of SEQ ID NO:4) derived therefrom; the single base pair deletion is indicated by a box;

FIG. 3 provides the nucleotide sequence for the ORF3 (SEQ ID NO:5) of Chinese HEV strain (DDBJ Accession No. D11092) and the E3 fragment (SEQ ID NO:6) derived therefrom;

FIG. 4 provides the amino acid sequence of the pE2 peptide (SEQ ID NO:2) encoded by E2;

FIG. 5 provides the amino acid sequence of the pE3 protein (SEQ ID NO:7) encoded by E3;

FIG. 18 shows the production of pE2 antibody by Macaque monkeys in response to immunization with purified pE2. Three monkeys (M1, M2 and M3) were each immunized with 4 weekly injections of 100 ug of purified pE2. Three control monkeys (M5, M7 and M8) were given placebo. Two weeks after the completion of immunization, both groups of animals were infected by intravenous injection of $10^5$ genome equivalent dose of HEV and the animals were further observed for 7 weeks. Serum samples were taken weekly and analysed for the presence of anti-pE2 antibody using an ELISA test;

DETAILED DESCRIPTION OF THE INVENTION

Figure 1:
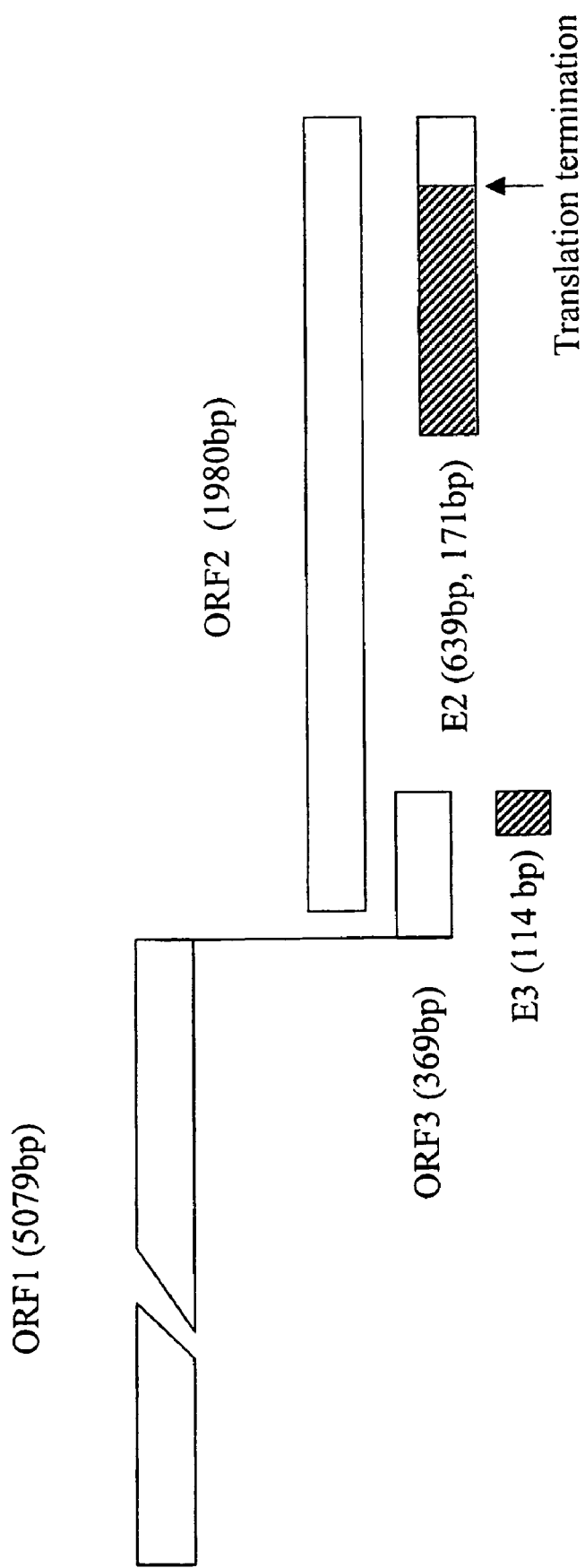
FIG. 1 illustrates the genomic organization of the open reading frames ORF1, ORF2 and ORF3 within the HEV genome and the approximate location of the coding region for the pE2 and pE3 peptides.

Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry described below are those well known and commonly employed in the art. Standard techniques are used for recombinant nucleic acid methods, cell culture and transformation. Generally, enzymatic reactions and purification steps are performed according to the manufacturer's specifications. The techniques and procedures are generally performed according to conventional methods in the art and various general references (Sambrook et al., Molecular Cloning: A Laboratory Manual, $2^{nd}$ Ed., Cold Spring Harbor Laboratory Press, Plainview, N.Y., 1989). As employed throughout the disclosure, the following terms, unless otherwise indicated, shall be understood to have the following meanings:

Biological test sample refers to a component of an individual's body which is the source of the analyte of interest. Examples of test samples include, without limitation, human and animal body fluids such as whole blood, serum, plasma, cerebrospinal fluid, white blood cells, secretions of the intestinal tract, urine and lymph fluids.

E2 is the cloned cDNA fragment which spans positions 6326 to 6968 of the genome of the Chinese HEV strain (DDBJ Accession No. D11092) illustrated in FIG. 2 and which contains a single base pair deletion at position 6957 (i.e. SEQ ID NO: 1).

pE2 is the peptide encoded by E2 (i.e. SEQ ID NO: 2).

E3 is the cloned cDNA fragment which corresponds to position 5364 to 5477 of the genome of the Chinese HEV strain (DDBJ Accession No. D11092) as illustrated in FIG. 3.

pE3 is the peptide encoded by E3 as illustrated in FIG. 4.

GE2 is a fusion protein whereby the amino terminus of pE2 is linked with the carboxy-terminus of glutathione S-transferase.

GE3 is a fusion protein whereby the amino terminus of pE3 is linked with the carboxy-terminus of glutathione S-transferase.

Hepatitis E Virus (HEV) is a single stranded positive RNA virus morphologically similar to members of the calcivirus. It can cause sporadic cases or endemic outbreaks of hepatitis, and is serologically distinct from hepatitis A virus (HAV), hepatitis B virus (HBV), hepatitis C virus (HCV) and hepatitis D virus (HDV).

Homodimer is a molecule formed by the union of two identical monomers.

Homologous sequence is a nucleic acid or amino acid sequence having at least 80%, and more preferably 90%, sequence identity to the E2 nucleic acid sequence, or pE2 amino acid sequence, identified as SEQ ID NO: 1 or 2, respectively.

I HEV Genomic Sequences

The HEV genomic sequences illustrated in FIGS. 2A to 2D and FIG. 3 correspond to the ORF2 and ORF3 regions, respectively. Similarly, the peptide sequences shown in FIGS. 4 and 5 correspond to the gene products derived from the ORF2 and ORF3 regions, respectively. Accordingly, the genomic sequences listings shown are as follows:

SEQ ID NO. 1 is the nucleic acid sequence of the cloned DNA fragment E2, derived from ORF2.

SEQ ID NO.2 is the amino acid sequence of peptide pE2.

SEQ ID NO: 3 is the nucleic acid sequence of the downstream primer, ORF2Rc.

II HEV Peptides pE2 and pE3

Expression of pE2 and pE3 Peptides from the HEV Genome

Figure 6:
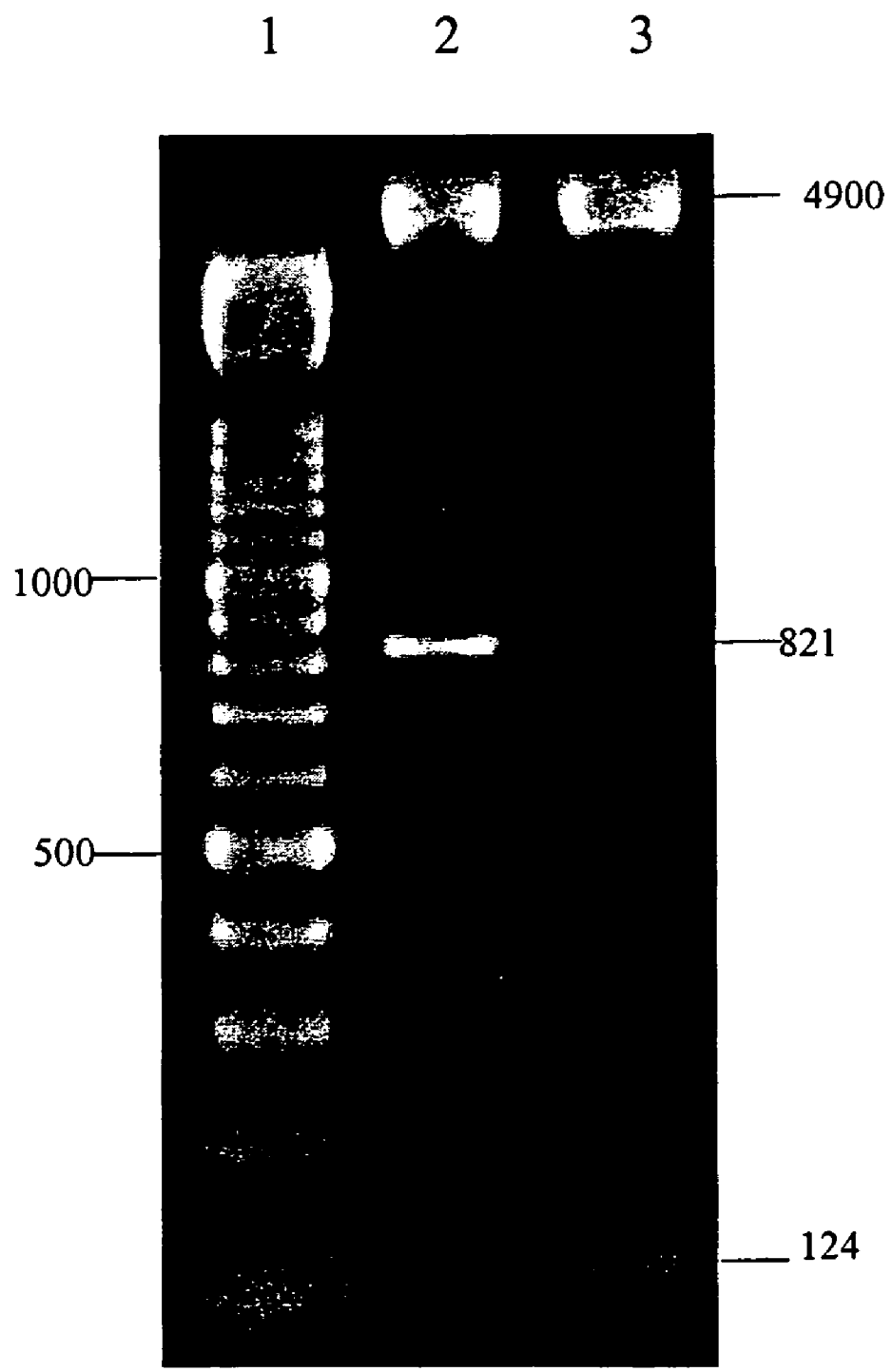
FIG. 6 shows the characterization of recombinant plasmids carrying the HEV genomic sequences. A 821 bp insert containing a 810 bp sequence of ORF2 (Lane 2) and a 124 bp insert containing a 114 bp sequence of ORF3 (Lane 3) of the HEV genome were obtained by digestion of recombinant pGEX$_{20}$ plasmids with BamHI and EcoRI. The molecular weight of these products were compared with markers (Lane 1)

A 114 bp region from the 3' end of the ORF3 sequence and a 811 bp region from the 3' end of the ORF2 sequence located within the genome of a Chinese strain D11092 of HEV were cloned and amplified by reverse transcription-polymerase chain reaction (RT-PCR). These sequences were subsequently ligated to the BamHI and EcoRI cloning sites on a pGEX vector. The cloned viral genes were recovered by digestion of the respective plasmids with EcoRI and BamHI (FIG. 6, Lanes 2 and 3) and subjected to sequence analysis. The analysis located the 114 bp sequence to positions 5364 to 5477 within the viral genome. It was predicted to specify a 37 aa peptide, pE3, with a MW of 3.9 kD. The 811 bp sequence was located at position 6326 to 7136, however, the analysis also revealed a single base pair deletion at position 6957 (FIG. 2D), presumably due to a PCR amplification error. The resulting frameshift was predicted to cause translation of the nucleic acid sequence to terminate prematurely at a new stop codon at position 6968, thus giving a smaller than expected peptide of 213 amino acid residues in length, pE2, with a MW of 23 kD, instead of 267 amino acid residues as initially expected. Three amino acid residues at the carboxy-terminus of pE2 which were produced by the frameshift are non-HEV sequence (SEQ ID NO: 2).

The nucleotide sequences shown in FIGS. 2A to 2D and 3 correspond to the ORF-2 and ORF-3 regions, respectively, of the Chinese strain of HEV (DDBJ Accession No. D11092).

The amino acid sequences shown in FIGS. 4 and 5 correspond to the peptides, pE2 and pE3, derived from the ORF-2 and ORF-3 regions, respectively, of the Chinese strain of HEV (DDBJ Accession No. D11092).

Characterization of the HEV ORF2 and ORF3 Specified Proteins

The sequences cloned from both the ORF-2 and ORF-3 regions of the HEV genome were expressed as glutathione S-transferase (GST) fusion peptides, GE2 and GE3, respectively. This expression system gave a high yield of the viral peptides and permitted efficient purification when using the Glutathione Sepharose-4B system. This method yielded about 2 mg of purified GE2 and 7 mg of GE3 from one liter of bacterial culture. Alternatively, GE2 bound to sepharose-4B could be eluted using thrombin, which cleaved the fusion protein at the carboxy-terminus of GST to release the viral peptide pE2. This procedure yielded about 1 mg of the purified pE2 peptide from one liter of bacterial culture.

Figure 7:
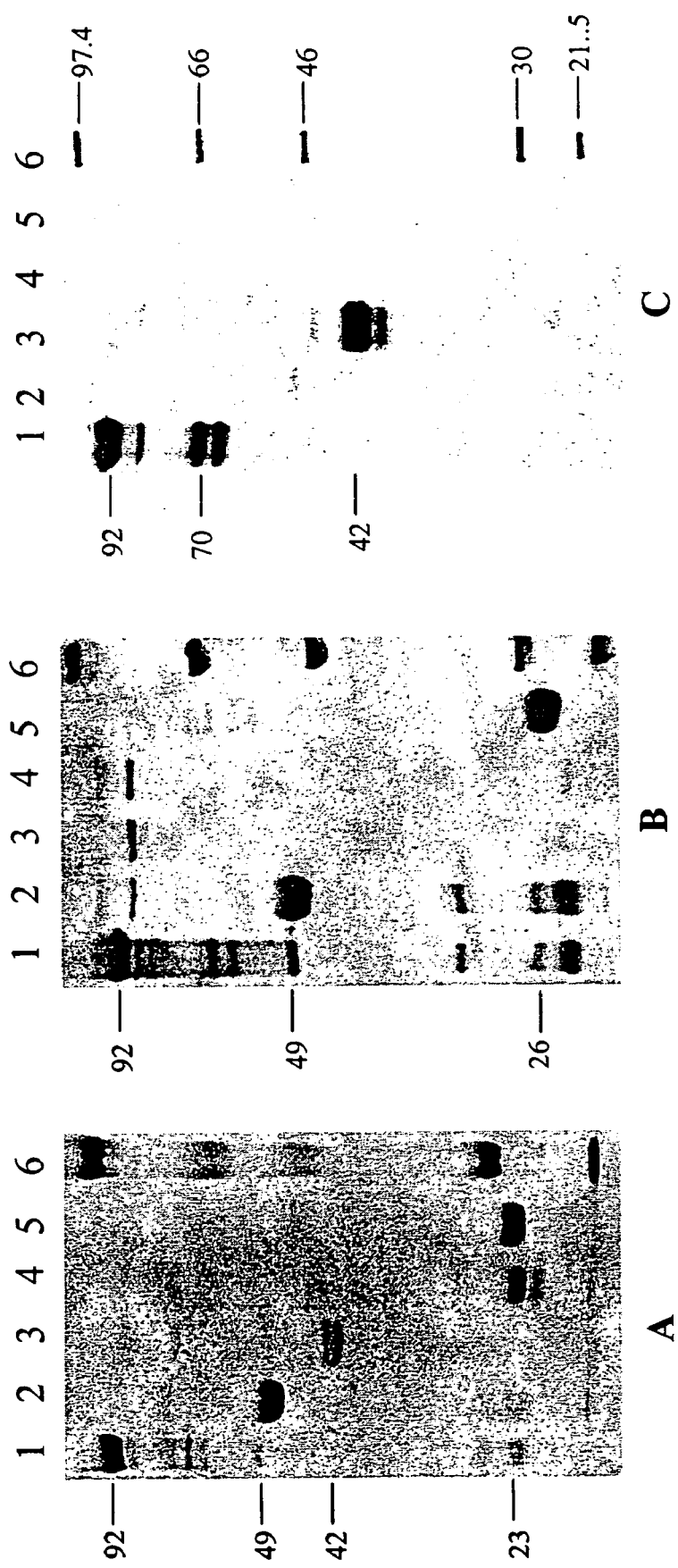
FIG. 7 shows the characterization of purified HEV recombinant peptides expressed from ORF2. Purified pE2 fusion protein, GE2 (Lanes 1 and 2), pE2 peptide (Lanes 3 and 4) and glutathione S-transferase (GST) fusion protein (Lane 5) were subjected to analysis by (A) SDS PAGE and (B) Western blotting using a GST-specific antiserum and (C) a pooled human HEV reactive human serum. In addition, samples of the GE2 and pE2 peptides were heated at 100° C. for 3 minutes for subsequent analysis (Lanes 2 and 4) by SDS PAGE (A) and Western blotting (B and C). The molecular weight of these products were compared with markers (Lane 6)

The purified preparations of GE2 and pE2 were characterized by SDS PAGE and Western blotting techniques (FIG. 7). Purified pE2 fusion protein, GE2 (Lanes 1 and 2), pE2 peptide (Lanes 3 and 4) and glutathione S-transferase (GST) fusion protein (Lane 5) were subjected to analysis by (A) SDS PAGE and (B) Western blotting using a GST-specific antiserum and (C) a pooled human HEV reactive human serum. In addition, samples of the GE2 and pE2 peptides were heated at 100° C. for 3 minutes for subsequent analysis (Lanes 2 and 4) by SDS PAGE (A) and Western blotting (B and C). Purified GE2 was resolved as a major band in a dimeric form with a MW of 92 kD (FIG. 7A, Lane 1), but dissociated into a 49 kD band after the sample had been heated at 100° C. for 3 minutes (FIG. 7A, Lane 2). Both the dimeric and monomeric forms of GE2 were recognized by anti-GST serum in the corresponding Western blot (FIG. 7B, Lanes 1 and 2). It was noted that the 49 kD GE2 monomer, one of the minor components in this preparation, was only reactive with anti-GST and not with the human HEV reactive serum (FIG. 7C, Lane 2). Accordingly, when GE2 was heated at 100° C. for 3 minutes, the 49 kD monomer became the major band but its antigenicity against human HEV sera was markedly reduced (FIG. 7C, Lane 2). The pE2 peptide, which was purified by digestion of the bound fusion peptide with thrombin, had naturally formed a dimer of 42 kD which also became dissociated into a 23 kD monomer after heating at 100° C. for 3 minutes (FIG. 7A, Lanes 3 and 4, respectively). Neither the dimeric nor the monomeric forms of pE2 were recognized by anti-GST serum (FIG. 7B, Lanes 3 and 4). Furthermore, only the dimeric form of pE2 was reactive with the human HEV serum (FIG. 7C, Lanes 1 and 3).

Figure 8:
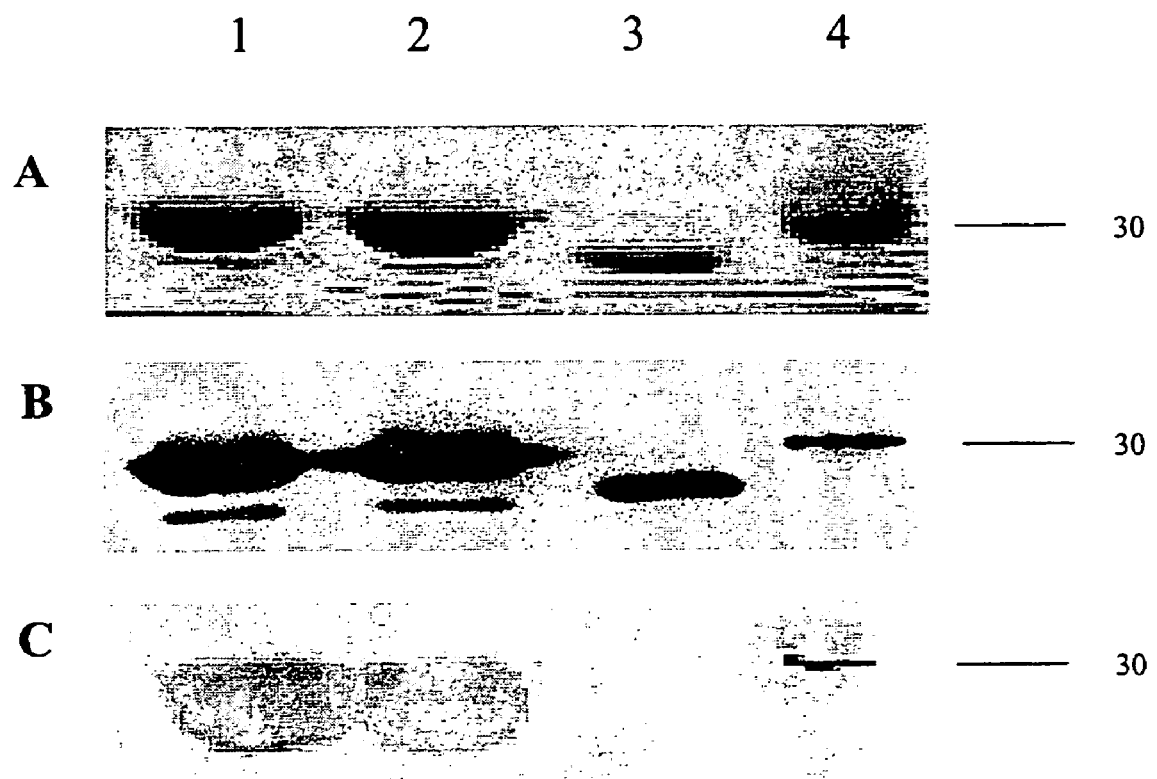
FIG. 8 shows the characterization of the GST fusion peptide, GE3, expressed from ORF3 of the HEV genome. The GE3 peptide (Lane 1), which was heated at 100° C. for 3 minutes (Lane 2), and GST (Lane 3) were subjected to analysis by (A) PAGE and (B) Western blotting using a GST specific antiserum and (C) a pooled human serum. The molecular weight of these products were compared with markers (Lane 4)

The purified GST fusion protein expressed from ORF3 (GE3) was also characterized by SDS PAGE and Western blot (FIG. 8). The GE3 protein occurred as a monomer which migrated as a band with the expected MW of 30 kD. Western blot showed that GE3 was reactive with both the anti-GST antiserum and the pooled HEV human serum. However, in contrast to pE2 and GE2, the reactivity of GE3 was associated only with a monomeric form since its antigenic activity was not affected by heating. Therefore, it is likely that such activity is attributed, at least partly, to epitopes located by previous peptide mapping studies to the carboxy-terminus of the ORF3 specified full length protein.

III E2 and Its Antigenic Activity pE2 Peptide Naturally Occurs as a Homodimer

Previous studies have described recombinant peptides of the HEV structural protein encoded by ORF2 of the HEV genome which are recognized by HEV reactive human sera (Yarbough et al., 1991; Li et al, 1994). By the technique of peptide mapping using overlapping short peptides spanning the length of the structural protein, the activity of these antigenic peptides has been attributed to the number and the nature of antibody binding sites located to different regions along the length of the polypeptide. Referred to as linear epitopes, these antibody binding sites are related to the primary structure of the protein as determined by its amino acid sequence. The configuration assumed by the recombinant peptides in solution, which is determined by their secondary and tertiary structures, may affect accessibility of the epitopes to antibodies and hence, reduce their antigenic activity.

The recombinant pE2 peptide of the present invention exhibits two types of antigenic activity recognizable by HEV reactive human sera. One type of antigenic activity is related to the primary structure of the pE2 peptide, whereas the second type of activity is related to the quarternary structure of the peptide in its dimeric form. The first antigenic activity is attributed to linear epitopes contained within the amino acid sequence of the pE2 peptide and which are associated with its monomeric form, as identified by Western blotting and described below. However, the second type of antigenic activity is strictly conformational in nature and only results when monomers of the pE2 peptide associate with one another to form homodimers. Therefore, an outstanding feature of the pE2 peptide which differentiates it from other HEV recombinant peptides is that it naturally and predominantly forms homodimers (e.g. higher oligomers) under physiological conditions and that the antigenic activity of this peptide is attributed to conformational antigenic determinants presumably arising from the quarternary structure of the pE2 peptide achieved through its dimeric form alone. Furthermore, the antigenic activity is abrogated upon dissociation of the dimer but the activity can be restored upon reconstitution of the dimer from the monomeric form. Accordingly, this type of antigenic activity is the first of its kind to be reported for a recombinant peptide derived from the ORF2 region of the HEV genome.

FIG. 7 shows that a pooled human HEV reactive serum is strongly reactive against the dimeric form of the glutathione S-transferase (GST) fusion protein of pE2 (i.e. GE2) and purified pE2. Purified GE2 (Lanes 1 and 2) and purified pE2 (Lanes 3 and 4) were produced as described herein and subjected to analysis by (A) SDS-PAGE and (B) Western blotting using an antiserum raised against GST and (C) a pooled HEV reactive human serum. The samples appearing in Lanes 2 and 4 were heated at 100° C. for 3 minutes immediately before the analysis. A purified sample of GST and a mixture of molecular weight markers were loaded to Lanes 5 and 6, respectively. In the unheated samples (7A, Lanes 1 and 3), the fusion protein, GE2, migrated mainly as a dimer of an approximate molecular weight of 92 kDa (7A, Lane 1) and pE2 as a dimer of an approximate molecular weight of 42 kDa (7A, Lane 3). However, as illustrated in FIG. 7A, Lanes 2 and 4, heating caused the dimeric forms of both proteins to dissociate into a 49 kDa monomeric GE2 fusion protein and a 23 kDa monomeric pE2 peptide, respectively. It was discovered following Western blotting that the fusion protein, GE2, in either its dimeric or monomeric forms, was recognized by antiserum raised against GST (7B, Lanes 1 and 2), as well as GST, as expected (7B, Lane 5). The HEV reactive human sera strongly recognized the dimeric form of the GE2 fusion protein (7C, Lane 1) and the pE2 peptide (7C, Lane 3). Heating of the samples at 100° C. for 3 minutes resulted in the dissociation of the dimeric form of both the GE2 fusion protein and the pE2 peptide into their corresponding monomeric forms. However, this dissociation is associated with a concomitant loss of antigenic activity as indicated by the inability of the HEV reactive human sera to recognize and bind to the monomeric forms of the GE2 protein and the pE2 peptide (7C, Lanes 2 and 4, respectively).

Figure 9:
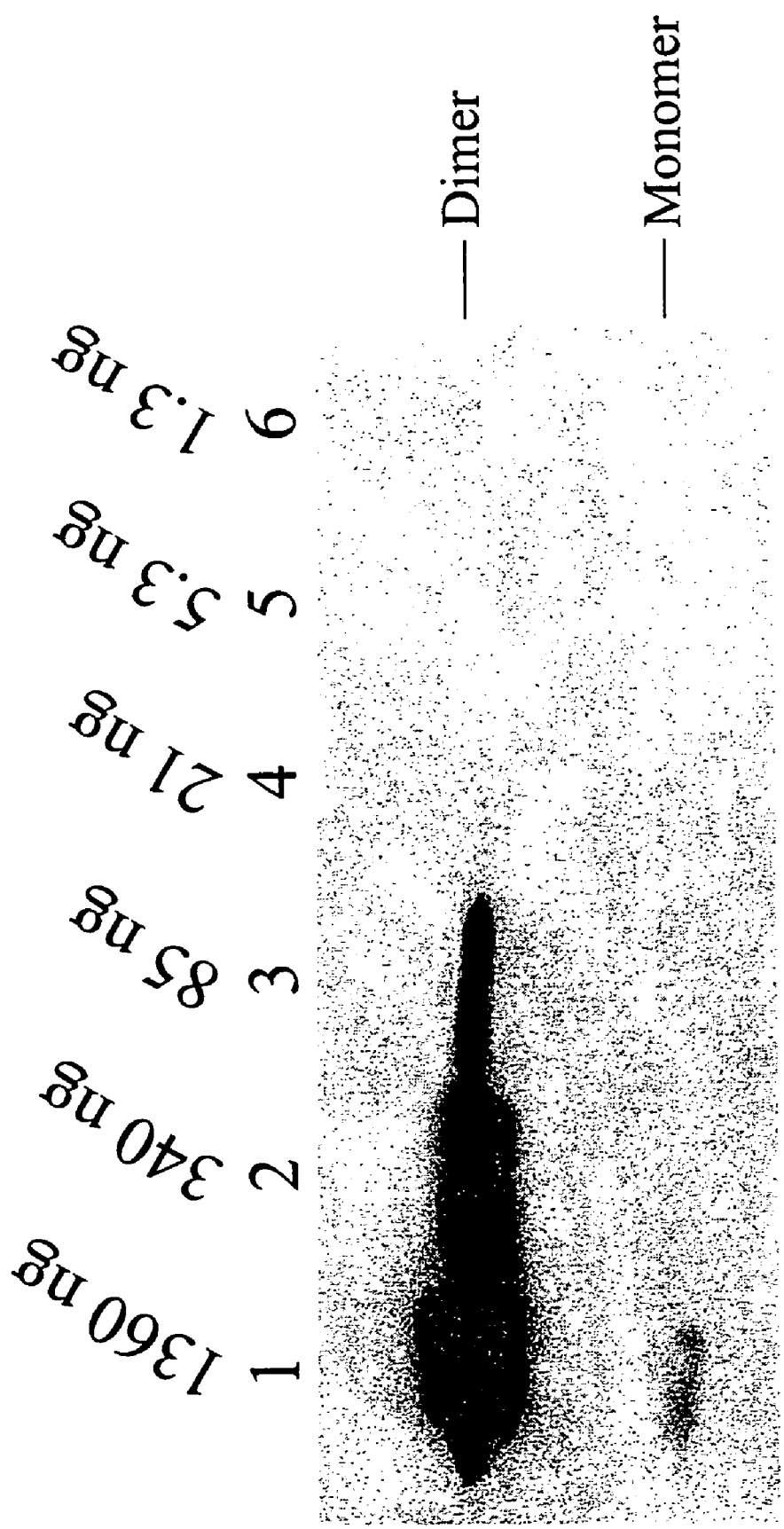
FIG. 9 shows that the antigenic activity of the pE2 dimer is about 80 times stronger than the antigenic activity of the pE2 monomer. Graded amounts from between 1.3 and 1,360 nanograms of equivalent samples of heated and unheated purified pE2, as described below for FIG. 10, were subjected to Western blotting using a pooled HEV reactive human serum at 1:200 dilution. The minimum amount of the pE2 monomer detected by the pooled serum was 1,360 ng, which is about 16 times higher than the minimum amount of the pE2 dimer detected at 86 ng, under the same conditions. The reactivity against the dimer at limiting concentration was estimated to be at least 5 times more intense than the reaction observed against the limiting concentration of the monomer. Therefore, taken together, the antigenic activity of the pE2 dimer was estimated to be about 80 times stronger than that of the pE2 monomer.

The antigenicity of the pE2 monomer was assessed and compared with that of pE2 dimer by Western blot (FIG. 9). Equal amounts of unheated and heated samples of the purified pE2 peptide were mixed. The mixture was diluted serially at 4 fold dilution and loaded into lanes 1 to 6. After electrophoresis, the antigenicity of both forms of pE2 was determined with a pooled HEV reactive human serum used previously in FIG. 7 at 1:200 dilution. FIG. 9 shows that the minimum amount of the pE2 monomer in which the pooled human serum gave a positive reaction was 1,360 ng, which is about 16 times higher than the minimum amount of 86 ng determined for the pE2 dimer when tested under the same conditions. Furthermore, the intensity of the reaction against the pE2 dimer was estimated to be approximately 5 times stronger than the intensity of the reaction against the pE2 monomer. Therefore, the combined results demonstrate that the antigenic activity associated with the pE2 dimer is largely distinct from the monomer and that the overall reactivity of the pE2 dimer is approximately 80 times greater than that of the pE2 monomer. The antigenic activity of the pE2 monomer is attributed to several linear epitopes contained within the primary structure of the pE2 amino acid sequence.

Figure 10:
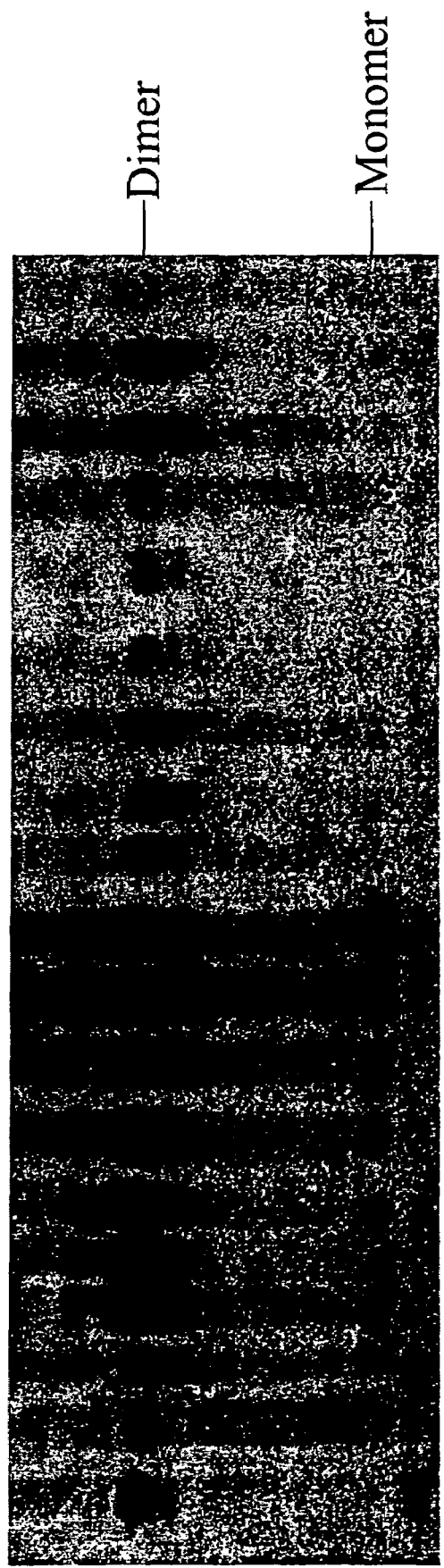
FIG. 10 shows the different antigenicity of the recombinant pE2 peptide in its dimeric and monomeric forms. An equivalent sample containing 1,300 nanograms of purified pE2 was heated for 3 minutes at 100° C. to dissociate the dimeric form of the peptide into its monomeric form. The heated sample was mixed in equal proportions with a sample of purified pE2, which had not been heated. The 23 kDa monomeric, and the 42 kDa dimeric, forms of the peptide were separated by SDS PAGE and transblotted onto membrane. The membrane was cut into strips for Western blot analysis. Tested at a serum dilution of 1:50, 8 sera were reactive against both the pE2 monomer and pE2 dimer, whereas the other 10 sera were only reactive against the pE2 dimer.

In addition, 18 individual human sera positive for a commercial HEV ELISA kit (Genelabs Diagnostics Pte Ltd., Singapore) were tested at dilution 1:50 by Western blotting (FIG. 10) against an equal mixture of a sample of purified pE2 (1360 ng for each form of pE2 per reaction) which, prior to analysis, was either left untreated to conserve the dimeric form of the pE2 peptide, or heated at 100° C. for 3 minutes to dissociate the pE2 dimer into its monomeric form. According to the results shown in FIG. 10, only 8 of the 18 sera were reactive against the both the pE2 dimer and monomer while the remaining 10 sera were reactive only against the pE2 dimer. The higher prevalence of antibody reactivity against the pE2 dimer compared to the monomeric form is a further indication that the dimer is more antigenically reactive than the monomer.

Figure 11:
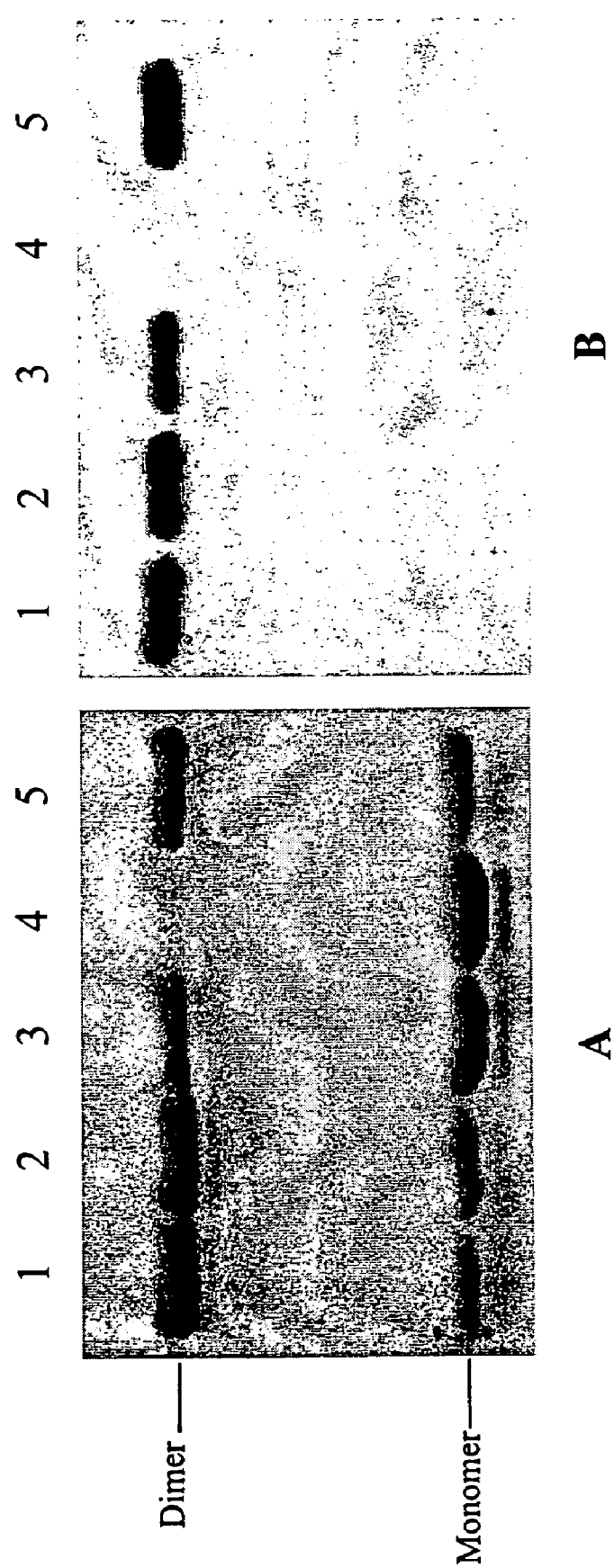
FIG. 11 shows the treatment of purified pE2 peptide with 8 M urea for 1 hour at 4° C. (Lane 1), 20° C. (Lane 2), 37° C. (Lane 3) and 45° C. (Lane 4). An equivalent sample of purified pE2 that was treated with 8 M urea at 45° C. for 1 hour was also dialyzed against 1×PBS overnight (Lane 5). The five samples were subjected to (A) PAGE and (B) Western blotting using a pooled HEV reactive human serum.

FIG. 11 shows that the second type of antigenic activity inherent to the pE2 dimer is related to the quarternary structure of dimeric, or oligomeric, forms of the pE2 peptide. Referred to as conformational antigenic determinants, this type of antigenic reactivity associated with recombinant peptides, other than pE2, which are derived from the ORF2 region of the HEV genome is hitherto unknown. Prior to SDS PAGE (A) and Western blot analysis (B), separate samples of purified pE2 were treated with 8M urea for 1 hour at four different temperatures: 4° C. (Lane 1); 20° C. (Lane 2); 37° C. (Lane 3); and 45° C. (Lane 4). Moreover, a portion of the sample treated at 45° C. was subsequently dialysed overnight to remove the urea (Lane 5) prior to SDS PAGE and Western blot analysis. Western blotting was carried out using a pooled HEV reactive human serum at a dilution of 1:250. The results obtained by SDS PAGE (FIG. 11A) show that the extent to which the pE2 dimer dissociated into its monomeric form had increased with an increase in temperature during the heating process until complete dissociation of the pE2 dimer was eventually achieved at 45° C. (Lane 4). Consistent with these results, the corresponding Western blot analysis (FIG. 11B) illustrates that only in samples in which the pE2 dimer is present (i.e. Lanes 1 to 3 and Lane 5) does the HEV reactive serum exhibit any degree of reactivity. Alternatively, the HEV reactive human serum shows no reactivity whatsoever towards the heated sample which contained only the monomeric form of the pE2 peptide (i.e. Lane 4).

These results suggest that under physiological conditions, pE2 monomers naturally associate with one another to form homodimers and that the conformational antigenic determinants recognized by HEV reactive human serum are likely due to the occurrence of such dimeric interactions since antibodies against the monomeric form of pE2 could not be detected. Accordingly, this second type of antigenic activity which is determined by the quarternary structure of the pE2 dimer appears to be strictly conformational in nature and is only functional when the pE2 peptide is in its dimeric form. Consequently, dissociation of the dimeric form of the pE2 peptide was shown to be associated with a loss of conformational antigenic activity (i.e. FIG. 11B, Lane 4). However, the conformational antigenic activity could be restored upon reassociation of pE2 monomers to form dimers following overnight dialysis of the urea-treated samples against PBS (FIG. 11B, Lane 5).

pE2 Conformational Antigenic Determinants Important in HEV Infection

As shown and described above, of the two types of pE2 antigenic activity recognizable by HEV reactive human sera, the conformational antigenic determinants of the dimeric form appear to play a more significant role in natural HEV infection than the linear epitopes of the monomeric form. This was concluded when the results of a Western blot analysis (FIG. 10) showed that out of a total of 18 HEV reactive human sera, all 18 sera were reactive against the dimeric form of the pE2 peptide, while only 8 of the sera were additionally reactive against the monomeric form of the pE2 peptide. Furthermore, based on the results shown in FIG. 9, the overall reactivity of the pE2 conformational antigenic determinants was estimated to be about 80 greater than that of the linear epitopes contained within the monomer.

The role of the pE2 conformational antigenic determinants in natural HEV infection was further evaluated by testing sera from 21 healthy blood donors and 96 patients having non-A, B and C acute hepatitis taken at different times after onset of hepatitis (Table 2). The sera used in the study was obtained from patients admitted to the Princess Margaret Hospital in Hong Kong with current, or a past history of non-A, B and C acute hepatitis. The results show that pE2 specific IgG antibody was markedly more prevalent among the non-A, B and C hepatitis patients than the healthy donors. The difference is consistent with epidemiological studies indicating that HEV is a common cause of non-A, B and C hepatitis. The detection of the IgG antibody suggests that some of these patients may be currently infected and others may have been previously infected with the virus. About 10% of the healthy donors had been infected with the virus in the past and this is in agreement with the level of HEV infection in the community from which these blood samples were taken.

TABLE 2

Detection of HEV Antibodies in Human Sera by Western Blotting

| Antibody (IgG) Profiles pE2 | Number of Sera From: | |
|---|---|---|
| | Non-A, B and C Hepatitis Patients | Healthy Blood Donors |
| + | 56 | 3 |
| − | 40 | 18 |
| Total | 96 | 21 |

IV Determining the HEV Specificity of pE2 and GE3

To ascertain that the antigenetic activity of pE2 dimer and pE3 is HEV specific, 74 of the 96 serum specimens obtained from patients with acute, or history of acute non-A, B and C acute hepatitis were further tested by a commercial HEV specific ELISA (Table 3). The high concordance rates between the commercial test and pE2 or GE3 tests demonstrate the HEV antigenic specificity of the pE2 and pE3.

TABLE 3

Detection of IgG antibody against pE2, GE3 and IgG HEV antibody by a commercial ELISA.

| Western Blotting | | EIA | | | Overall* |
|---|---|---|---|---|---|
| | | + | − | Total | Concordance |
| pE2 | + | 37 | 7 | 44 | 89.2% |
| | − | 1 | 29 | 30 | |
| GE3 | + | 30 | 0 | 32 | 89.2% |
| | − | 8 | 36 | 54 | |
| Total | | 38 | 36 | 74 | |

*Overall concordance = number of the specimens with concordant result/ number of total specimens × 100%.

V Establishment of ELISA to Detect IgG and IgM Anti-HEV

Figure 12:
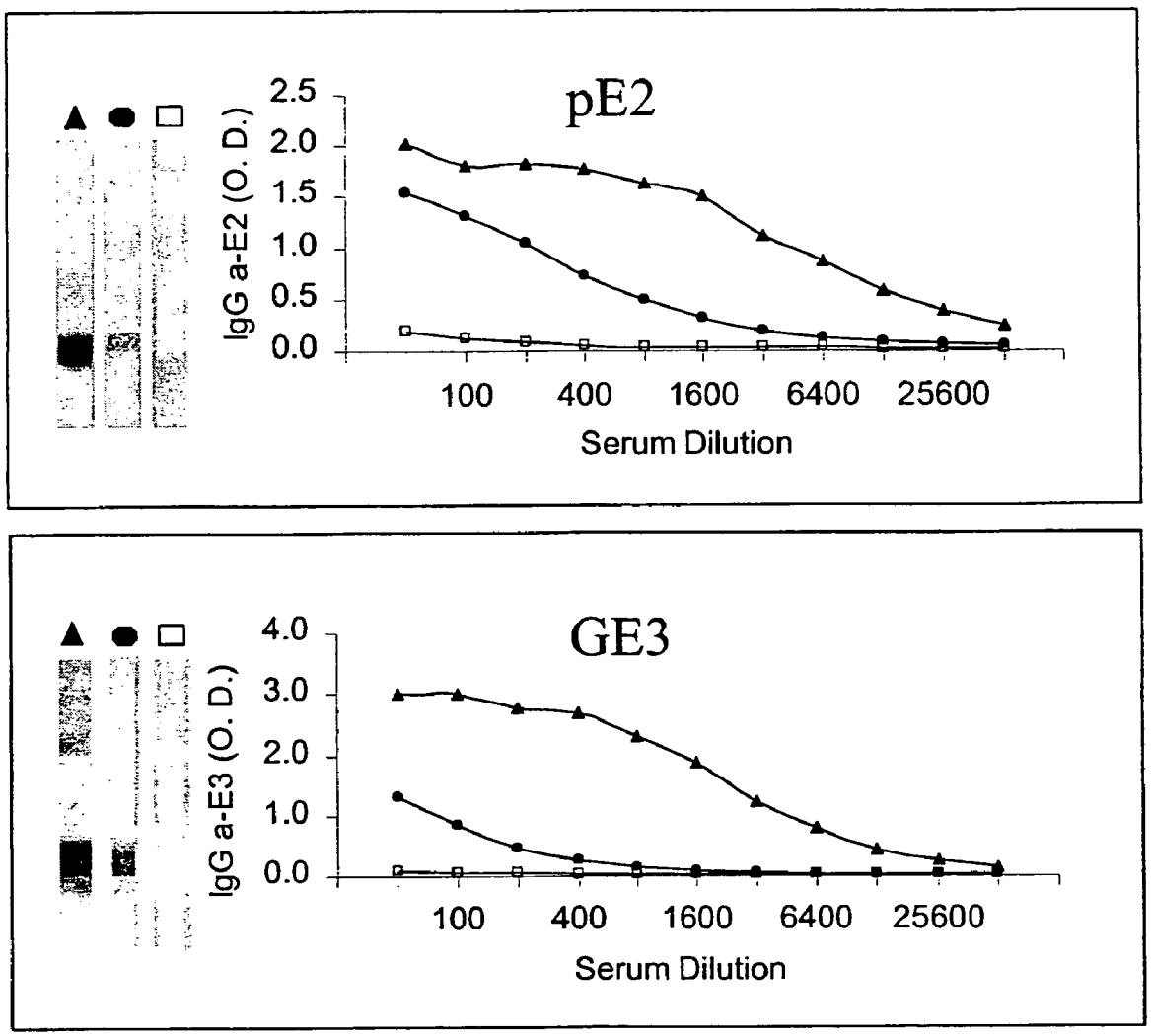
FIG. 12 compares the levels of IgG antibody present in three types of human sera which reacted with purified pE2 or GE3, as determined by ELISA. The level of IgG antibody contained in these sera was determined by titration using microplates that had been coated with a predetermined optimum concentration of a preparation of purified pE2 or GE3. The peptide preparations were analysed by SDS PAGE (left lane) and tested by Western blotting at 1:100 serum dilution. The human sera was either strongly reactive (solid circle), weakly reactive (hatched circle), or not reactive (open circle) against the corresponding recombinant peptides. The antibody level was defined as the reciprocal of the serum dilution, which gave an OD value that exceeded the cutoff OD value of 0.37.

The two separate ELISAs were conducted by coating microplates separately with purified preparations of either pE2 or glutathione S-transferase fusion protein GE3. Production and purification of these HEV peptides have been previously described. The purity of these preparations was determined by the relative intensity of the 42 kD pE2 dimer and the 30.4 kD GE3 fusion peptide such that they constitute 89% and 95% of the total proteins in their respective preparations (FIG. 12, left lane). Western blotting showed that these peptides were the principal antigens in these preparations as shown by a reaction with HEV positive human sera (FIG. 12, solid and hatched circles), but not with the control negative human serum (FIG. 12, open circles). Titration of these sera by assays produced with these purified HEV peptide preparations yielded typical results which correlated with the reactivity of these sera against corresponding peptides as determined by Western blotting.

Figure 13:
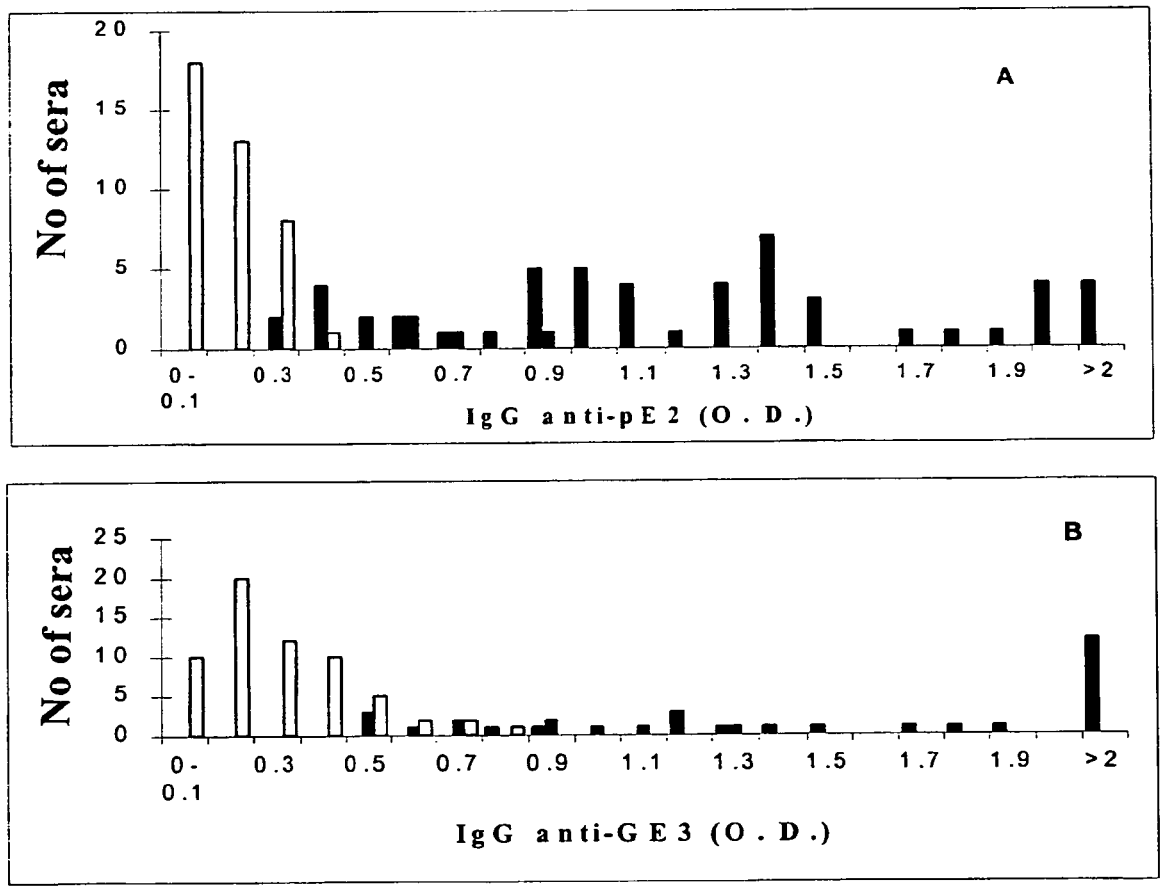
FIG. 13 shows the distribution levels of IgG antibody contained in sera obtained from 96 patients having non-A, B and C hepatitis as determined by ELISA which are strongly reactive (solid bar), weakly reactive (hatched bar) and not reactive (open bar) against purified pE2 or GE3. Each serum specimen was tested at 1:100 serum dilution by Western blotting and analysed by ELISA using microplates coated with purified pE2. The levels of the antibody were evidenced by OD values and the reactivity of the serum against the peptide was assessed according to the intensity of the reaction.

In an extended study, levels of HEV IgG antibodies were determined in serum specimens obtained from 90 healthy donors and 96 patients with current, or past history of non-A, B and C acute hepatitis using pE2 and GE3 specific assays. Antibody levels of individual patients sera generally correlated with their reactivity against the corresponding viral peptides as previously determined by Western blotting (FIG. 13). OD values obtained for the reactive sera (FIG. 13, solid bars) determined by Western blotting were higher than the weakly reactive (FIG. 13, hatched bars) or the non-reactive (FIG. 13, open bars).

By setting cutoff values at 5 SD above the mean OD values of non-reactive sera evidenced by Western blotting, 85.7% of pE2 reactive or weakly reactive sera gave a positive result by pE2 specific assay, and 66.6% of GE3 reactive sera gave a positive result by GE3 specific assay. Total concordance between Western blotting and pE2 and GE3 specific assays were 91.7% and 88.5%, respectively. Based on the Western blot results, both of the ELISA tests have 100% specificity, and discrepant results obtained by these assays and Western blotting were confined to the weakly reactive sera. These results confirmed that the pE2 assay was specific for the 42 kD pE2 dimer and the GE3 assay was specific for the 30.4 kD pE3 peptide. Seroprevalence of IgG pE2 antibodies as determined by ELISA was 50% for the HEV patients and 5.5% for the donors, and that of IgG GE3 was 22.9% for the HEV patients and 1.1% for the donors. Seroprevalence of pE2 specific antibody of either group of test subjects was higher than the GE3 specific antibody. This suggested that pE2 is the dominant of the two antigens and that a higher prevalence of either of these antibodies was associated with acute hepatitis.

Antibody Responses to Distinct Antigenic Domains of HEV Capsid Proteins

For a further comparison, IgG antibodies of 74 sera, out of the 96 sera, were further tested by a commercial test kit (Genelabs Diagnostics Pte Ltd., Singapore). The commercial test kit was made from a mixture consisting of a 42 amino acid peptide and a 33 amino acid peptide encoded from the 3' end of ORF2 and ORF3, respectively, of a Burmese and a Mexican strain of HEV (Yarbough et al., 1991). The 33 amino acid peptide of ORF3 used in the commercial test is found within a portion of pE3 (i.e. GE3) because, as previously described, pE3 is a 38 amino acid peptide which is also expressed from the 3' end of ORF3. Therefore, it is expected that the antigenic specificity of the ORF3-specified peptide in the commercial test would be closely related to that of GE3. On the other hand, the ORF2-specified peptide used in the commercial test is located further downstream from the carboxy-terminal end of the 213 amino acid pE2 peptide. Therefore, the antigenic specificity of the commercial test kit, which is partly determined by the ORF2 peptide contained within the kit, is expected to be different from the pE2 peptide of the present invention. Unlike previously reported HEV peptides derived from the ORF2 region, the antigenic activity of pE2 is unique in that it is mainly attributed to conformational antigenic determinants which are only exposed when pE2 monomers associate with one another to form homodimers.

Figure 15:
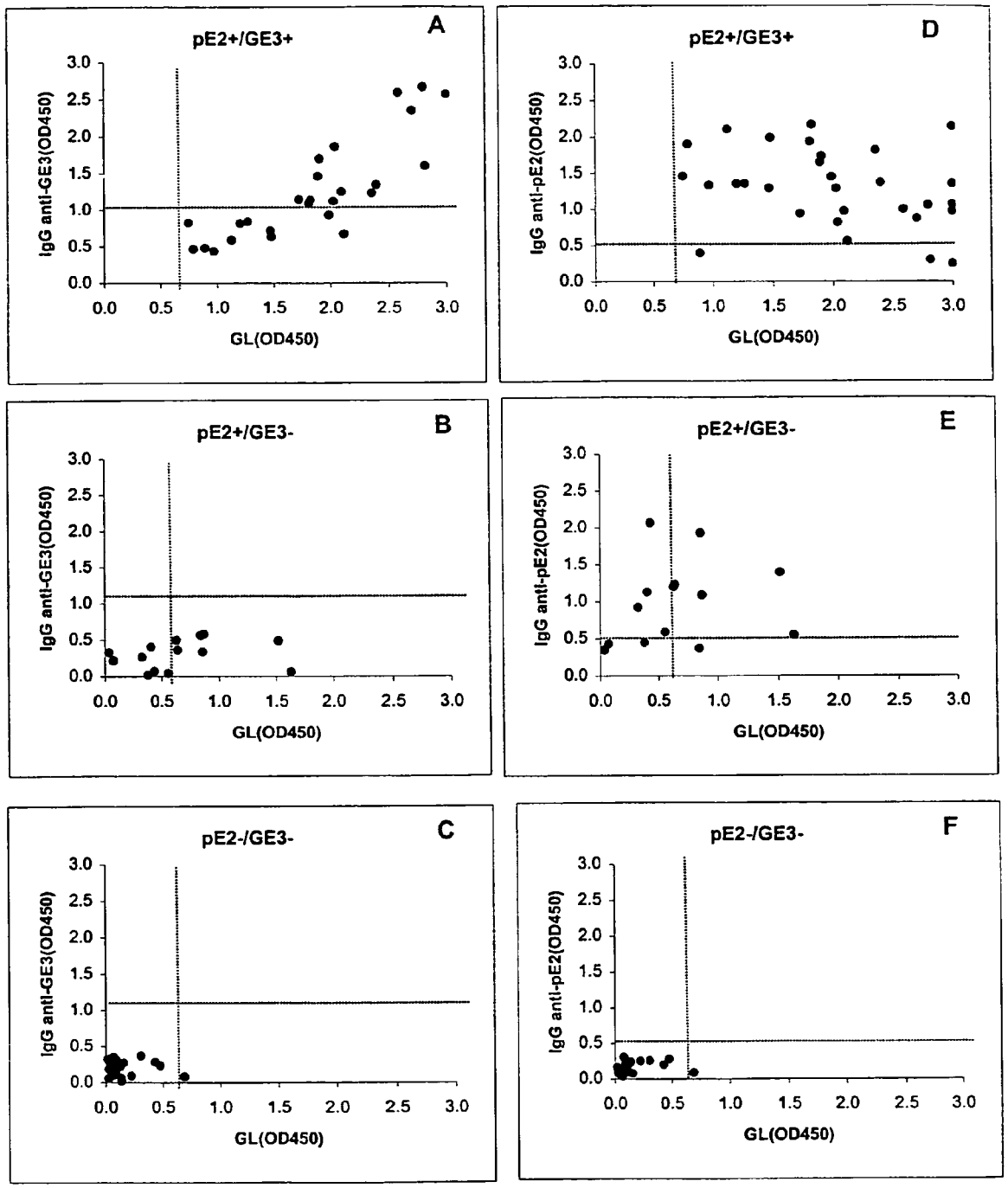
FIG. 15 illustrates the determination of antibodies by three ELISAs of distinct HEV specificity. HEV specific antibodies in sera from 74 hepatitis patients out of 96 non-A, B, and C hepatitis patients, were further tested by a commercially available assay (GeneLabs Diagnostics Pte Ltd., Singapore). The results were compared with those obtained by assay specific for GE3 (A, B and C) or specific for pE2 (D, E and F). Previously performed Western blotting showed that 32 of these sera were reactive against pE2 and GE3 (A and D), 14 were reactive against pE2 alone (B and E) and 40 were unreactive with either of these peptides (C and F). Cut-off OD values (dotted lines) were 0.6 for the commercial assay, 0.52 for pE2 specific IgG and 1.05 for GE3 specific IgG.

As evidenced by Western blotting, 30 of the sera were previously tested to be reactive for both pE2 IgG and GE3 IgG (pE2+/GE3+, FIGS. 15A and 15D), 14 were reactive for pE2 IgG only (pE2+/GE3−, FIGS. 15 B and 15E) and 30 were not reactive against either peptide (pE2−/GE3−, FIGS. 15 C and 15F). Consequently, levels of antibody determined by the commercial assay for the pE2 and GE3 reactive sera varied coordinately with levels of GE3 antibody (FIG. 15A) but independently with the levels of pE2 specific antibody (FIG. 15D). Eleven of these sera were weakly reactive for GE3 and gave low OD values which were below the cut-off values of the GE3 specific ELISA (FIG. 15A). Ten of the 14 sera reactive only against pE2 were found to contain different levels of the corresponding antibody. Seven of the 14 sera were reactive by the commercial assay (FIG. 15E). However, all of them gave a negative result by the GE3 specific ELISA (FIG. 15B). The remaining sera were unreactive against either peptide. All of them gave a negative result by both pE2 and GE3 specific ELISA, and all but one also gave a negative result by the commercial assay.

The spectrum of HEV antibody detected by the three assays is summarized in Table 4. Despite their distinct antigenic specificity, 33 sera were positive by both the pE2 specific assay and the commercial assay and 30 were negative by both assays, giving a total concordance of 87.8% between the two assays. Similarly, total concordance between the GE3 specific assay and the commercial assay was 74.3%. Overall concordance between the three assays combined was 66.2%. Frequency of detection of HEV antibody by the commercial assay (47%) was slightly lower than the pE2 specific assay (50%) and higher than the GE3 specific assay (29%). Based on the antibody spectrum exhibited by individual sera, antibody detected by the commercial assay in 15 of 40 sera can be attributed to those which are specific for the ORF2 specified peptide used to produce this assay because the sera were not reactive when tested by the GE3 specific assay. The remaining 23 sera gave a positive result by both the commercial assay and the GE3 specific assay, but it was not ascertained if these sera also contained antibody against the ORF2 specified peptide used to produce the commercial assay.

TABLE 4

Viral Hepatitis Patients' Sera Reaction Patterns Against HEV Peptides and Commercial ELISA Kit

| pE2 ELISA | GE3 ELISA | Genelabs Kit | Number of Sera (n = 74) |
|---|---|---|---|
| + | + | + | 17 |
| + | − | + | 16 |
| + | − | − | 4 |
| − | + | + | 2 |
| − | − | + | 3 |
| − | − | − | 32 |
| 37 (50%) | 19 (25.7%) | 38 (51.3%) | Prevalence (%) |
| 87.8% | 74.3% | − | Total Concordance (%)[1] |

[1]Total concordance (%) with the commercial ELISA kit equals the number of sera giving a positive result or a negative result by either pE2 or GE3 specific assays and the commercial assay simultaneously/total number of sera tested × 100%. Overall concordance between the three assays combined similarly was calculated to be 66.2%.

VI Antibody Responses in Current and Past HEV Infection

Figure 14:
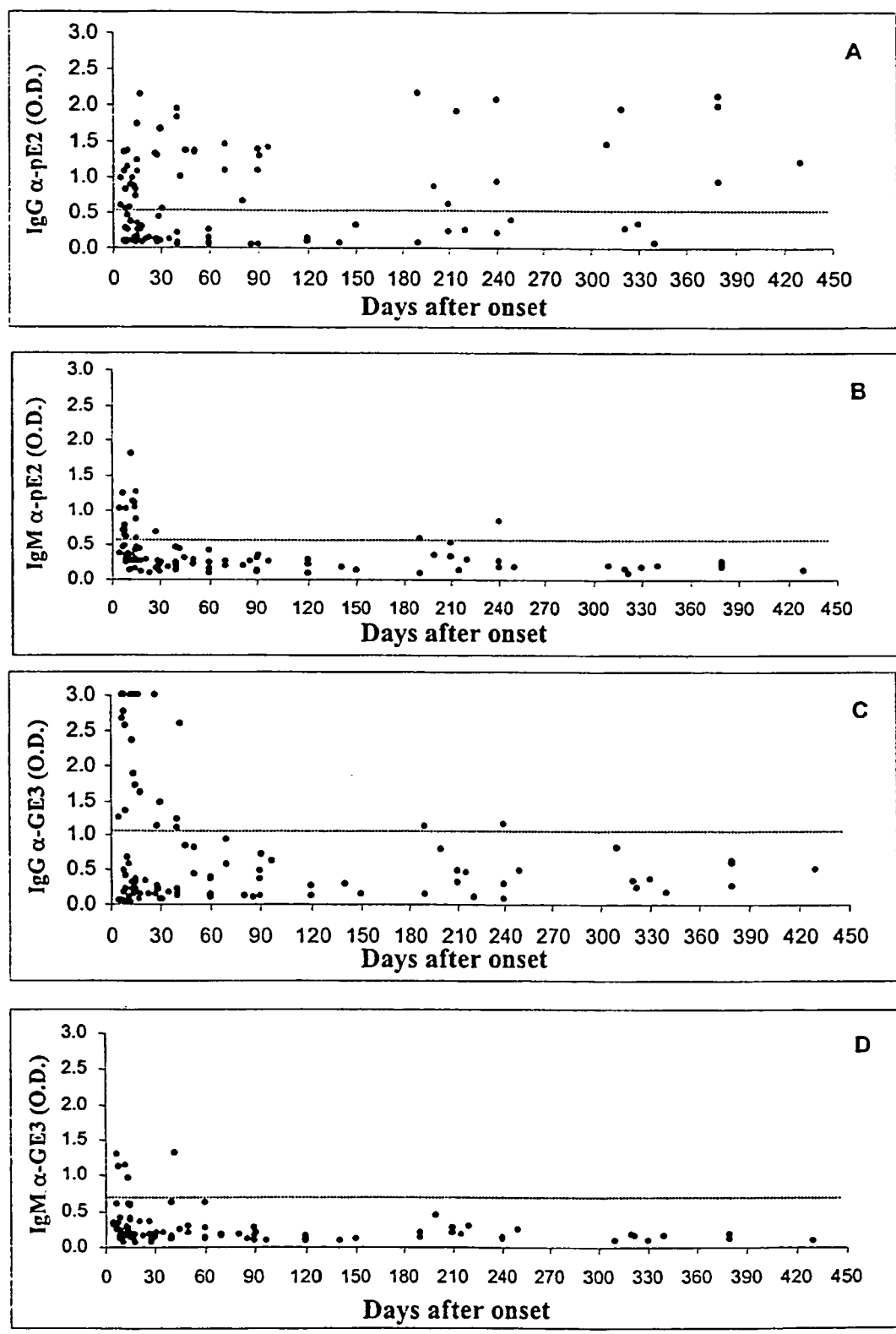
FIG. 14 illustrates the time distribution of HEV antibodies following the onset of the disease. pE2 specific (A) IgG and (B) IgM and pE3 specific (C) IgG and (D) IgM antibodies in sera from 96 hepatitis patients having non-A, B and C hepatitis were determined by ELISA produced with the respective HEV peptides. The results were compared with the lengths of time after disease onset when these sera were taken. Cut-off OD values (dotted line) were 0.52 for pE2 IgG, 0.57 for pE2 IgM, 1.05 for GE3 IgG and 0.74 for GE3 IgM.

The level of pE2 and GE3 specific IgM antibodies of sera from HEV patients and healthy donors was also determined. In a preliminary study, it was shown that the assay was not affected by the presence of IgG antibodies, such that results obtained in the presence and absence of anti-human IgG were essentially the same. Subsequent determinations were therefore done in the absence of anti-human IgG and cutoff values were set at 3 SD above the mean OD values of sera from 90 donors. FIG. 14 compares the occurrence of pE2 and GE3 antibodies in sera from patients with time of onset of hepatitis E. pE2 and GE3 specific IgM antibodies and GE3 specific IgG antibodies were mainly present in serum samples obtained early after onset of hepatitis E while occurrence of pE2 specific IgG antibodies were not related to disease onset.

Based on HEV antibody levels determined by pE2 and GE3 specific assays as in FIG. 14, individual serum specimens tested exhibited 9 distinct HEV serological profiles. A total of 53 patients' sera were found to variously reactive for one or more of these antibodies (Table 5). Eighteen sera exhibited five serological profiles which are consistent with current infection (Table 5, profiles 1 to 5). These include 3 sera which were reactive for pE2 IgM only (Table 5, profile 1), 11 sera which were additionally reactive for pE2 and GE3 specific IgG antibody (Table 5, profile 2) and another 3 which were reactive for these and also GE3 specific IgM antibody (Table 5, profile 4). The other sera were reactive for pE2 specific IgM and various other antibodies. It was noted that 16 of these samples were taken within 30 days after onset of hepatitis E. The other 2 patients' sera were taken more than 60 days after onset. These and the other sera from donors presumably were due to asymptomatic HEV infection unrelated to previous episodes of hepatitis E. Another 35 patients' sera exhibited serological profiles, which are consistent with past HEV infection (Table 5, profiles 6 to 8) being positive for IgG antibodies but not IgM antibodies. Twenty-seven of these sera were reactive for pE2 specific IgG (Table 5, profile 6) and seven were also reactive for GE3 specific IgG (Table 5, profile 7), but none were reactive for the IgM antibodies (Table 5, profiles 6 to 8). One profile showed sera that was not reactive to any of these antibodies (Table 5, profile 9). However, occurrence of these serological profiles were not related to time of onset of hepatitis E. Most of the specimens showing current infection profiles were obtained within 27 days (median=13 days) after onset of hepatitis E and the other specimens were obtained on days indicated in parenthesis. Past infection profiles did not correlate with disease onset, and these specimens were cumulated at a similar rate after disease onset as the non-reactive sera (median=50 and 40 days).

ments were carried out to determine if antisera raised against pE2 may effect immune capture of HEV particles.

Specificity of RT-PCR Primers

Figure 16:
FIG. 16 shows specific immune capture of HEV by polystyrene paddles coated with antiserum raised against purified pE2. The antiserum, taken from the animal M1 described in FIG. 19, was diluted 1:100 and used to coat the polystyrene paddles. The paddles were separately immersed overnight in solutions containing HEV (Lane 2), HAV (Lane 3), calicivirus (Lanes 4 and 5), or enterovirus (Lane 6). The paddles were removed from the solution, exhaustively washed in 4 changes of buffer solution. The RNA bound to the paddles was extracted, reverse transcribed and the cDNA was subjected to PCR amplification using primers for the corresponding viruses. The molecular weight of these products was compared with markers (Lane 1)

In this study, two pairs of primers, A5R/A3F and B5R/B3F (Table 9) were chosen for RT-PCR. The specificity of these primers was evaluated by direct RT-PCR with specimens separately containing HEV, HAV, enteroviruses and caliciviruses. FIG. 16 shows that only the specimen con-

TABLE 5

Serological Profiles of HEV Infection

| Profiles Identified | IgM | | IgG | | Donors No. of Sera (n = 90) | Patients No. of Sera (n = 96) | Days After Onset |
| --- | --- | --- | --- | --- | --- | --- | --- |
| | pE2 | GE3 | pE2 | GE3 | | | |
| 1 | + | − | − | − | 0 | 3 | 9–15 |
| 2 | + | − | + | + | 0 | 11 | 5–27 (190,240) |
| 3 | + | + | − | − | 1 | 1 | 8 |
| 4 | + | + | + | + | 0 | 3 | 7–14 |
| 5 | − | + | + | + | 0 | 1 | 18 |
| Total (Current Infection) | | | | | 1 | 18 | Median = 13 |
| 6 | − | − | + | − | 5 | 27 | 5–430 |
| 7 | − | − | + | + | 0 | 7 | 9–40 |
| 8 | − | − | − | + | 0 | 1 | 18 |
| Total (Past Infection) | | | | | 5 | 35 | Median = 50 |
| 9 | − | − | − | − | 84 | 42 | Median = 40 |

ELISA for the Determination of Low Avidity IgG Anti-pE2 Antibody

A further application of the ELISA method is for the determination of low avidity IgG antibody in serum using the pE2 dimer. This was accomplished by titrating serum specimens in the presence, and in the absence, of 4 M urea. The presence of low avidity IgG antibody is indicated when the urea treatment has caused the apparent antibody level to decrease significantly by more than 4 fold. Table 6 shows that the low avidity antibody was exclusively detected in the patients' sera, which were taken within 2 weeks after the onset of hepatitis E and that this antibody is subsequently replaced by avid IgG antibody on a gradual basis. Thus, the transient occurrence of the low avidity IgG antibody makes it potentially useful for the diagnosis of acute hepatitis E.

TABLE 6

D termination of low avidity pE2 IgG antibody by ELISA in serum samples of non-A, B and C hepatitis patients at different times after onset of the disease.

| | pE2 IgG Avidity Test (Cases) | | |
| --- | --- | --- | --- |
| Days After Onset | Low Avidity | High Avidity | Total |
| 0–7 | 3 | 0 | 3 |
| 8–14 | 3 | 3 | 6 |
| 15–21 | 3 | 0 | 3 |
| 22–84 | 0 | 12 | 12 |
| >84 | 0 | 7 | 7 |
| Total | 9 | 22 | 31 |

VII Establishment of Immune Capture RT-PCR to Detect HEV RNA

The above described reactivity of human sera may be explained if the pE2 dimer were to mimic certain structural features of the HEV capsid. To test this possibility, experitaining HEV presented a specific band with the expected size of the 203 bp HEV sequence following RT-PCR amplification.

pE2 Dimer Mimics Structural Properties of HEV

The antigenic relationship between pE2 dimer and HEV viral particles was studied by immune capture experiments using polystyrene paddles coated with antisera raised against the pE2 peptide. The antiserum used was obtained from a monkey immunized with 4 doses of 100 μg of purified pE2 and which was predominantly reactive against the pE2 dimer. The antiserum was weakly reactive against the pE2 monomer and it was not reactive with other HEV antigen. The paddles coated with the antiserum were found to effect specific immune capture of HEV particles and the bound virus was subsequently detected (Lane 2) by reverse transcriptase polymerase chain reaction (RT-PCR) as described herein under the section entitled "Materials and Methods". The paddles were similarly allowed to react with, but had failed to effect the capture of HAV (Lane 3), calicivirus (Lanes 4 and Lane 5) and enterovirus (Lane 6) (FIG. 16).

These results further support the contention that the pE2 dimer may mimic certain structural features of HEV viral particles which have enabled the antiserum to be predominantly reactive against the dimer and therefore, effect efficient and specific immune capture of the HEV particles. Application of this finding to develop an immune capture assay for the detection of HEV in clinical, food and environmental samples is discussed below.

Immune Capture RT-PCR (IC-RT-PCR)

Figure 17:
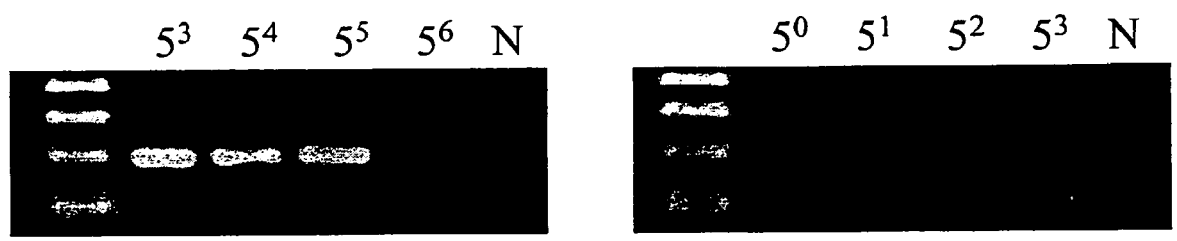
FIG. 17 illustrates the immune capture of HEV using polystyrene paddles coated with either (A) an pE2-specific antiserum or (B) a pre-immune serum, taken from animal M1 described in FIG. 18, and reacted with 4.5 ml samples of a serially-diluted bile containing HEV. After washing, HEV particles bound to the paddles were detected by RT-PCR. The molecular weight of these products were compared with markers (left lane)

Antiserum raised against pE2 in rabbits was tested for its ability to immune capture HEV. Polystyrene paddles, coated separately with the antiserum and the pre-immune serum, were used for capture of the virus. RT-PCR on the captured particles was performed. It was discovered that the antiserum could capture HEV particles up to a dilution of $5^5$ of the stock virus (FIG. 17A), while the pre-immune serum failed to capture the virus even with undiluted stock solution (FIG. 17B).

Comparison of a Commercial Viral RNA Detection Kit to IC-RT-PCR

The immune capture RT-PCR (IC-RT-PCR) method described above can be used routinely for the detection of HEV for public health and environmental monitoring because of the availability of a stable source of antisera derived from the expression of HEV specified protein, pE2.

In the method described below, immune capture of HEV partciles was followed by the extraction of HEV RNA with a commercial kit (QIAamp Viral RNA Kit, QIAGEN), the use of which is familiar to molecular biologists. If it is assumed that the efficiency of RNA extraction using a commercial kit is 100% without interference, then theoretically, IC-RT-PCR should be 32 times more sensitive than direct RT-PCR because the former can accommodate 32 times more volume of a sample. In this study, the seeding virus was diluted in 5-fold serial dilution so the expected results should be that IC-RT-PCR is 25-fold more sensitive than RT-PCR.

In this study, three types of HEV-seeded specimens were prepared which included plain water, the supernatant of human stool specimens and the supernatant of homogenized shellfish specimens. The water sample, a shellfish (e.g. oyster) sample and a stool sample were spiked with the same amount of HEV. The spiked samples were serially diluted in 5 fold increments and aliquots of the diluted samples were tested for the presence of HEV by the commercial (conventional) method and by the immune capture method. The comparative efficiency of HEV capture from these specimens was examined and the results are provided in Table 7. According to these results, the immune capture method demonstrates increased sensitivity over the conventional RT-PCR method for the detection of HEV in the water sample by 25 fold, in the stool sample by 125 fold and in the shellfish samples by more than 125 fold. Therefore, the results show that IC-RT-PCR is at least 25 times more sensitive than the commercial viral RNA kit. The reason for increased sensitivity observed with the water samples was because the sample volume tested by the immune capture method was 32 times the sample volume tested by the conventional RT-PCR method. Moreover, the results also indicate that there are unknown factors in the supernatant of stool and shellfish which inhibit the extraction of RNA for subsequent synthesis of cDNA. This is why the results for the water samples are significantly higher than for the shellfish and stool supernatant samples as the water samples are not expected to contain substances which may inhibit detection. However, this interference observed with the stool and shellfish samples is reduced to a minimum using IC-RT-PCR over the convention RT-PCR method. The increased sensitivity of the IC-RT-PCR method in excess of 25 fold over the conventional RT-PCR method is attributed to the removal of inhibitory substances by the immune capture method.

TABLE 7

Comparative Efficiency of HEV Detection by Immune Capture-RT-PCR and Conventional RT-PCR Methods

| Method | Water | Stool Supernatant | Shellfish Supernatant |
| --- | --- | --- | --- |
| IC-RT-PCR | 1:3, 125 | 1:125 | 1:125 |
| Conventional RT-PCR | 1:125 | 1 (not diluted) | not detected |

Sensitivity of detection is indicated as the limiting sample dilution required for virus detection.

In conclusion, both the commercial RT-PCR method and the IC-RT-PCR method have a lower sensitivity for the stool and shellfish samples than for the water sample. However, this phenomenon may be caused by some unknown factors in the stool and shellfish samples which can possibly accelerate the degradation of viruses. On the other hand, the IC-RT-PCR results are 125-fold more sensitive than using direct RT-PCR which implies that the immune capture method successfully overcame the interference from unknown facts in the stool and shellfish samples and further illustrates that IC-RT-PCR is practical as a clinical and environmental monitor.

VIII The Role of pE2 in HEV Protection

The previous results of the study of non-A, B and C hepatitis patients, indicated that the dimeric form of the recombinant peptide, pE2, may assume an important role in natural HEV infection through the exposure of conformational antigenic determinants which are generated from the dimerization of the monomeric form of the peptide.

As previously shown in the study of non-A to C acute hepatitis patients, the dimeric form of pE2 was found to assume a more prominent role in natural HEV infection. pE2 specific IgM antibodies were commonly produced during acute HEV infection. The corresponding IgG antibodies were also produced and persisted for a protracted period of time accompanied by increasing avidity. Furthermore, they were the most prevalent HEV antibodies present in convalescent sera and sera from individuals previously infected with the virus. These results suggested that pE2 may afford protection against HEV and is further supported by a protection study in the experimental infection of Macaque monkeys. Moreover, the results also suggest that the protective effects are mainly attributed to the conformational antigenic determinants exhibited through dimerization of the pE2 peptide as opposed to the presentation of linear epitopes and provides a rational basis for vaccine development.

A protection study in experimental infection using a Macaque monkey model shows that immunization with a purified preparation of the pE2 peptide confers protection of the animals against a HEV challenge and therefore, makes it a prime vaccine candidate. The infective dose was found to approximate the genomic dose and the pathology associated with experimental infection was comparable to that associated with natural infection in humans (Tsarev et al., 1993b; Tsarev et al., 1994b). In order to obtain a clear indication as to whether the bacterially expressed peptide affords protection against HEV, the animals used in the present study were challenged with a relative large dose containing at least $10^5$ genome equivalent of the homologous strain of HEV virus. Virus excretion in stool and viraemia seen in the control animals were essentially abrogated in the immunized animals. None of these animals developed additional HEV antibodies apart from anti-pE2 antibodies already present before the challenge. Since anti-pE2 antibodies present in the pre-challenge sera were predominated by those which specifically recognize the pE2 dimer rather than its monomeric form, it was concluded that to a large extent, the protective effects are attributed to the conformational antigenic determinants that arise from the dimerization of this viral peptide. Consistent with this belief, study and characterization of the pE2 peptide suggests that it probably encompasses a domain in the major structural protein of HEV, which interacts to form HEV capsid. Therefore, the viral capsid is generated with the same or similar conformational antigenic determinants compared to those generated through the pE2 dimerization. Consequently, antibodies specific for pE2 dimers are the dominant antibody response to natural HEV infections.

The nucleotide sequence specifying the 210 aa HEV peptide, pE2, was compared with the reported nucleotide sequence and predicted amino acid sequences in the corresponding regions of prototype HEV strains. The 210 aa peptide is encoded in a highly conserved region in the ORF2 of the HEV genome (Table 1). Purity of the viral peptide used for immunization was assessed by SDS PAGE (FIG. 7A, Lane 3) and its antigenicity, by immune blotting using a human HEV reactive (FIG. 7C, Lane 3). PE2 constituted over 90% of the protein present in the purified preparation used for immunization. The dimeric form was specifically recognized by the HEV reactive human serum (FIG. 7C, Lane 3), but not the 23 kD monomeric form (FIG. 7C, Lane 4). These results suggest that anti-HEV antibodies present in the human serum are mainly directed against conformational antigenic determinants arising from the dimerization of the viral peptide.

Immunization

Three test monkeys (M1, M2, M3) were immunized with four weekly intra-muscular doses of 100 μg of a preparation of purified pE2 dimer. Another three monkeys (M5, M7, M8) were given placebo and served as controls. The animals were bled 2 weeks after the fourth immunization dose and the sera tested by Western blotting against purified pE2, GE3 and by a commercial ELISA test. The animals were subsequently challenged with $10^5$ genome equivalent of the homologous strain of HEV two weeks following the final immunization dose.

The antibody response to the immunization was monitored using an ELISA produced with purified pE2 peptide (FIG. 18). The results showed that immunization elicited a vigorous antibody response against the viral peptide in all the three animals (M1 to M3). The antibody was first detected one week after the first immunization and reached the maximum level about one week after receiving the third dose. The control animals did not show detectable pE2 specific antibody. This vigorous response seen in all three animals shows that pE2 is strongly immunogenic.

The HEV specificity of the sera obtained immediately before virus challenge was further analyzed by Western blotting against equal samples of native (i.e. pE2 dimer) and heat-denatured purified pE2 (i.e. pE2 monomer) (FIG. 19A, Lanes 1 to 4), a purified GE3 fusion protein (FIG. 19B), and by a commercial ELISA assay for detecting HEV (FIG. 19C). The latter assay is an ELISA produced with a mixture of two synthetic HEV peptides corresponding to the amino acid sequences of the carboxy-terminal regions of the ORF2 and ORF3 specified proteins. According to the manufacturer's instructions, the assay utilized two HEV peptides, one is similar to pE3 (i.e. GE3) and the other corresponds to the carboxy-terminal region of the major structural protein of HEV which is located adjacent to, but does not overlap with pE2.

FIG. 19A shows the determination of the level of antibodies against the pE2 dimer and monomer by Western blotting using aliquots of the sera which were serially diluted in 4-fold increments. The serum from M1 was tested between a dilution of 1:4000 (Lane 1) and 1:256,000 (Lane 4); the serum from M2 was tested between 1:100 (Lane 1) and 1:6,400 (Lane 4); and the serum from M3 was tested between 1:250 (Lane 1) and 1:16,000 (Lane 4). The blots were produced with equivalent preparations of the dimeric and monomeric forms of purified pE2 peptide. The level of the antibody against either form is defined as the maximum dilution (limiting dilution) of the serum which is reactive against the respective form of the peptide. The results show that the level of the antibody against the dimer in the serum taken from M1 is 1:64,000, which is 16 times higher than the level of the antibody against the monomer, the limiting dilution being 1:4,000. The levels of the antibody against the dimer in the serum taken from M2 and M3 were 1:1,600 and 1:4,000, respectively, which were more than 16 times and 4 times higher than the corresponding levels of the antibody against the monomer in the same sera. None of the sera obtained from these animals before immunization showed detectable activity at 1:100 serum dilution (FIG. 19A, Lane 5).

FIG. 19B shows that at a dilution of 1:100, none of the sera were reactive against purified GE3. The same sera was tested at the same dilution by a commercial ELISA, which was produced with a synthetic peptide corresponding to the carboxy-terminal of the major HEV structural protein and the protein specified by ORF 3 of the HEV genome. FIG. 19C shows that none of the sera contained detectable antibody against these HEV peptides. Sera from the control animals was also similarly tested by the methods described above and none of the sera showed detectable HEV antibody by any of these methods as well.

Therefore, these results show that the pE2 peptide is highly immunogenic and capable of eliciting a vigorous antibody response in monkeys, as well being capable of promoting an immune response in other mammalian hosts, such as mouse, rat, sheep or rabbit. The antibody produced in response to the immunization was predominantly reactive against the pE2 dimer. The levels of these antibodies, as determined by limiting dilution, were 4 to 16 times higher than the corresponding levels of the antibodies against the monomer. This shows that the pE2 dimer is the dominant immunogen because it caused a higher level of antibody production than the monomeric form. Moreover, immunization with purified pE2 did not elicit the production of other HEV antibodies detectable by other commercially available methods. Therefore, it may be concluded from these results that the antisera thus raised against purified pE2 is specific for pE2, more particularly the dimeric form of the peptide.

Moreover, the antiserum diluted beyond the limiting dilution for the monomer can only be rendered reactive against the dimer and not the monomer. In accordance with the normal practice in immunology, such antisera rendered "monospecific" for the dimer by appropriate dilution as described herein can be used to distinguish the dimer and the conformational antigenic determinants expressed by the dimers from the monomers and the linear epitopes contained therein.

HEV Challenge

Three test animals (M1,M2,M3) and three control animals (M5, M7, M8) were challenged 2 weeks following their immunization by intra-peritoneal injection of a homologous strain of HEV. The challenging virus was originally isolated from an outbreak in China in 1986 (Table 1, Strain D11092) and the amount of the virus injected was estimated by PCR to be $10^5$ HEV genome equivalent per dose (FIG. 20). The primate infection dose of the challenging virus injected was not determined. Recent studies by other investigators showed that primate infectivity titres of HEV are of the same order of magnitude as genomic titres.

Following the experimental infection, the animals were observed daily for the development of hepatitis E virus. Virus excretion was monitored in stool samples obtained before, and every two days after the infection. Peripheral blood samples were obtained twice per week for the determination of viral load in the plasma and peripheral blood monocytic cells (PBMC). Serum specimens were taken for determination of ALT levels. Both groups of animals had normal levels of ALT and did not develop symptoms of hepatitis E. This presumably was because the virus has been attenuated through previous passages in primates (Zhuang et al., 1992). Nevertheless, Table 8 shows that one control animal, M5, excreted the virus in every stool sample taken between the $5^{th}$ and $17^{th}$ days post-infection. Virus excretion persisted for 10 days from the $7^{th}$ to $17^{th}$ days in the other two control animals, M7 and M8. The HEV genome was also detected in the PBMC specimens taken from M7 on the $9^{th}$ day and from M8 on the $13^{th}$ day after the infection. The HEV genome was not detected in any plasma samples taken from these animals. Immunization with the pE2 peptide completely abrogated virus excretion in two of the test animals, M1 and M2, it reduced virus excretion to one day in the third test animal, M3, and the viral genome was not detected in any of the plasma or PBL samples taken from these animals.

TABLE 8

HEV Excretion in Stool and Viraemia After Virus Challenge

| | | Day After Challenge | | | | | | | | | |
|---|---|---|---|---|---|---|---|---|---|---|---|
| Group | Monkey | 3 | 5 | 7 | 9 | 11 | 13 | 15 | 17 | 19 | 21 |
| Test | No. 1 | − | − | − | − | − | − | − | − | − | − |
| | No. 2 | − | − | − | − | − | − | − | − | − | − |
| | No. 3 | − | + | − | − | − | − | − | − | − | − |
| Control | No. 5 | − | + | + | + | + | +[1] | + | + | − | − |
| | No. 7 | − | − | + | +[1] | + | + | + | + | − | − |
| | No. 8 | − | − | + | + | + | + | + | + | − | − |

[1]The HEV genome was detected in peripheral blood monocytes by RT-PCR. None of the plasma samples contained detectable HEV genome.

HEV Seroconversion After Virus Challenge

Figure 19:
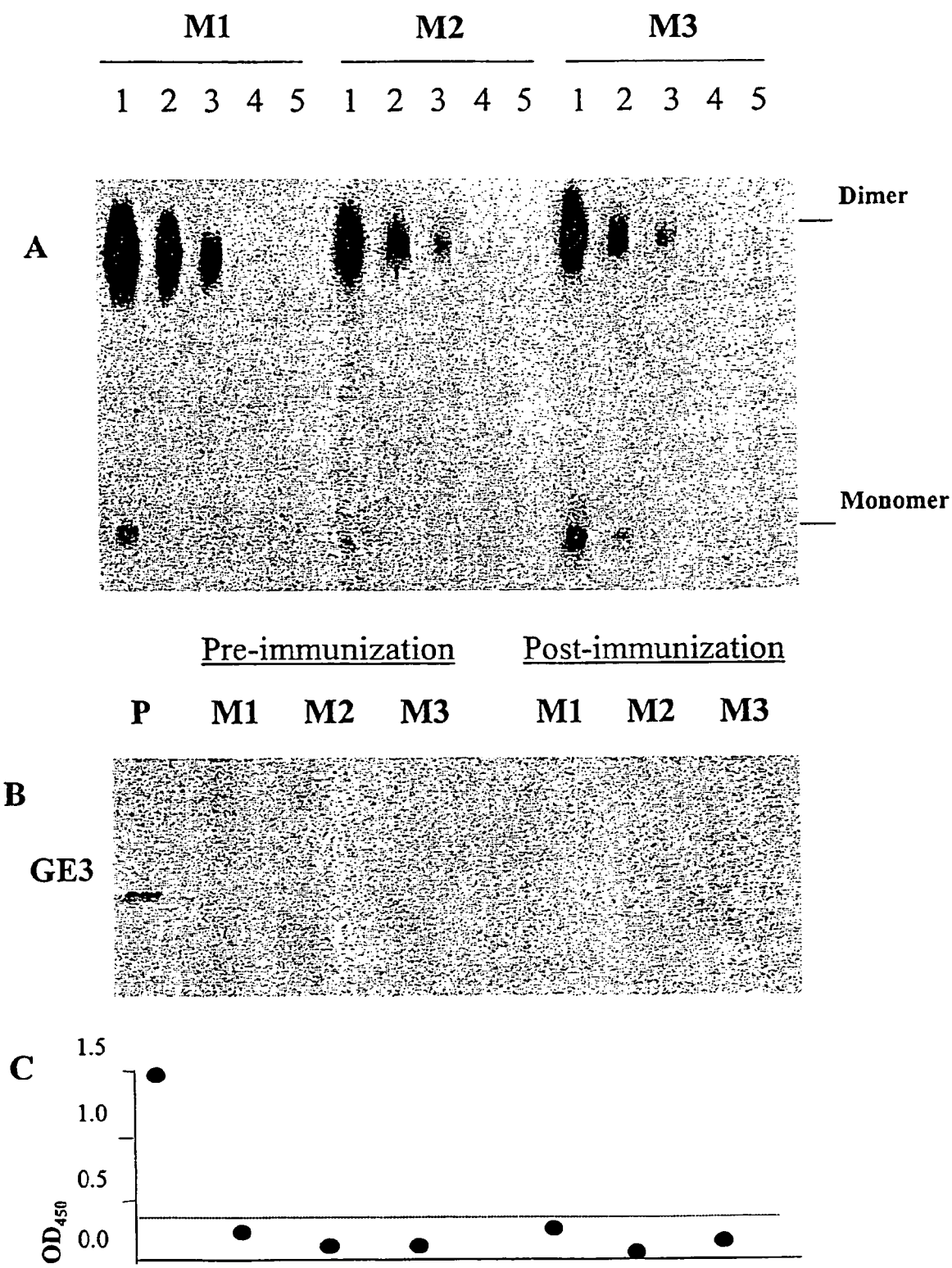
FIG. 19 illustrates the spectrum of HEV antibodies present in sera taken from Macaque monkeys following immunization with preparations of purified pE2 peptide, and before HEV challenge. Three adult monkeys (M1, M2 and M3) were injected four times at weekly intervals with a preparation containing 100 ug of purified pE2. The sera obtained 2 weeks after the final injection was serially diluted in 4 fold increments and tested by Western blotting against equal mixtures of the monomeric (heated for 3 minutes at 100° C.) and dimeric (untreated) forms of purified pE2. The immune serum from M1 was tested at 4-fold serial dilutions of 1:4,000 to 1:256,000 (Lanes 1 to 4); the sample from M2 was tested at the dilutions of 1:100 to 1:6,400; and the sample from M3 was tested at 1:250 to 1:16,000. Pre-immunized sera was tested at 1:100 as a negative control (lane 5) (A). Both the preimmune and the immune sera from these animals and a positive control serum, P, were further tested at 1:100 dilution by Western blotting against GE3 (B), the 30 kDa GST fusion protein containing the pE3 peptide, and by ELISA (C) using a commercial assay (Beijing Medical University, Beijing). The cutoff OD value of the ELISA recommended by the manufacturer is indicated by the dotted line.
Figure 20:
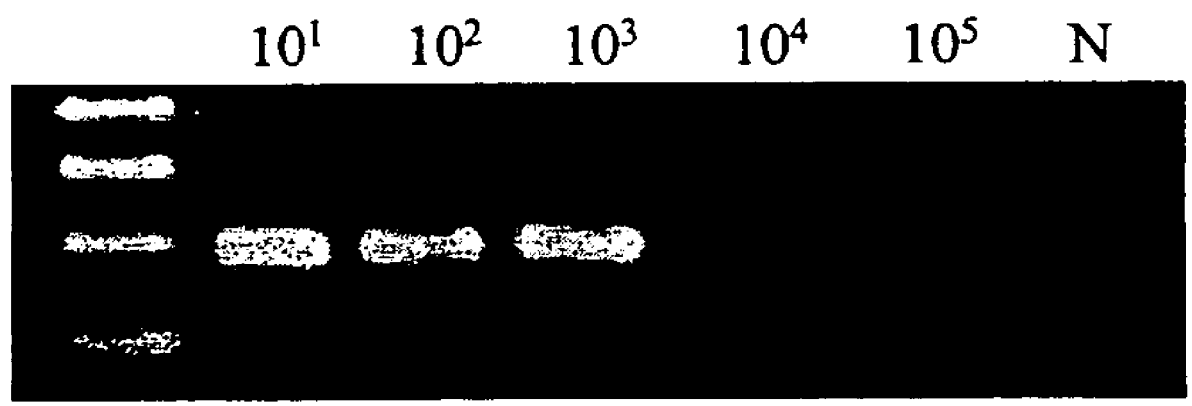
FIG. 20 illustrates the genomic dose of challenging hepatitis E virus. Animals were inoculated with 1 ml of a 1:100 dilution of a stock HEV. A genomic dose of the inoculating virus was determined by RT-PCR in serially diluted aliquots of the virus preparation as described herein under the subsection entitled "Materials and Methods"
Figure 21:
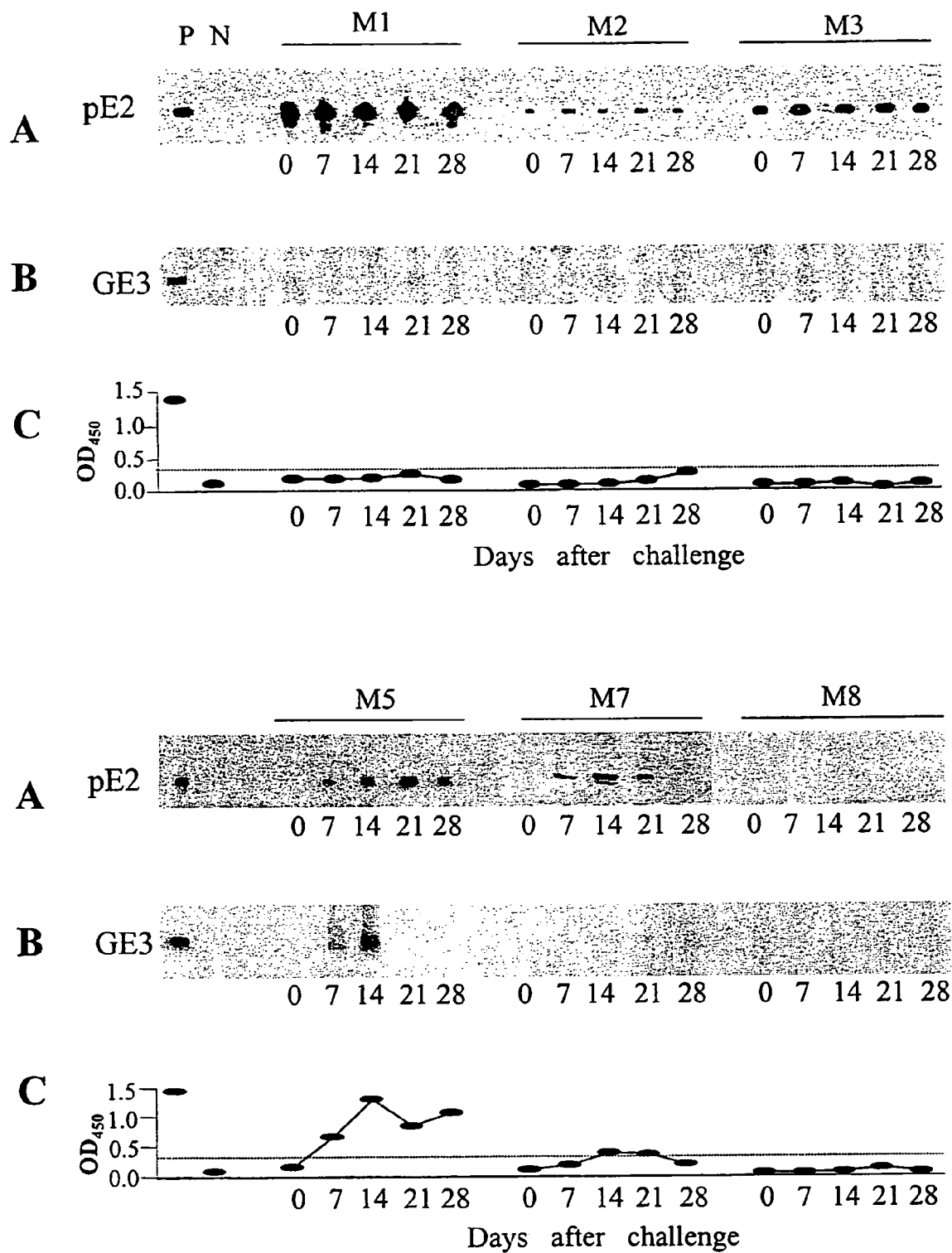
FIG. 21 illustrates the antibody response to the HEV challenge. Plasma samples were obtained from immunized (M1, M2, M3) and non-immunized control animals (M5, M7, M8) immediately before and at the indicated times following the HEV challenge. The serum samples as well as positive, P, and negative, N, control human serum samples were tested by Western blotting against purified pE2 and GE3, and by ELISA using a commercial assay (Genelabs Diagnostics Pte Ltd., Singapore)

The spectrum of HEV antibodies present in the serum samples obtained before and up to 4 weeks after virus challenge was analyzed according to the experimental methods and conditions described for FIG. 19. FIG. 21 shows that the sera obtained from all three control animals (M5,M7, M8) before virus challenge gave a negative result by all three HEV antibody assays initially. HEV seroconversion occurred 7 days following infection in one control animal, M5. This was evidenced by the detection of the pE2 homodimer specific antibody in sera taken on this day and all subsequent occasions (FIG. 21). All these serum samples also gave a possible test result for HEV antibody by the commercial ELISA test and the consecutive samples obtained on the $7^{th}$ day and $14^{th}$ day were reactive against purified GE3 as well. The broad specificity spectrum of the antibody response to the infection was in contrast to the restricted specificity spectrum of the antibody response to immunization with the pE2 peptide described earlier (FIG. 21). The serum specimens obtained from another control animal, M7, on the $14^{th}$ and $21^{st}$ days after infection were weakly reactive against the pE2 dimer and gave a positive result by the commercial assay, but none of the specimens were reactive against the ORF3 specified peptide, GE3. The remaining control animal, M8, did not mount a detectable antibody response to the infection. In contrast, except for the pE2 antibody, the immunized animals did not acquire other HEV antibodies after the infection (FIG. 21).

The sera obtained from the immunized animals (M1,M2, M3) were already reactive against the pE2 dimer before the virus challenge on day 0 and the antibodies persisted in the subsequent samples taken from these animals on days 7, 14 and 28 after the virus challenge. However, in contrast to the control animals, none of the immunized animals acquired additional HEV antibodies after the virus challenge (FIG. 21A).

Discussion

Previous studies had established the Rhesus monkey as to be a suitable animal model for HEV. The infective dose was found to approximate the genomic dose (Tsarev et al., 1994b) and the pathology associated with experimental infection was comparable to that associated with natural infection in humans (Tsarev et al., 1993b). In order to obtain a clear indication as to whether the bacterially expressed peptide affords protection against HEV, the animals used in the present study were challenged with a relative large dose containing at least $10^5$ genome equivalent of the homologous strain of HEV virus. We have shown that the infection has resulted in protracted virus excretion in the fecal samples for at least 10 days by all three control animals and a transient viraemia evidenced in two animals by the detection of the virus genome in the PBMC specimens. Moreover, the infection was accompanied by HEV seroconversion in two animals. Presumably because the challenging virus has been attenuated by previous passages in primates, however, all the control animals remained healthy with normal ALT levels.

Immunization with purified pE2 was found to elicit a vigorous antibody response against the peptide in both its monomeric and dimeric forms. The levels of the dimer reactive antibody were substantially higher than the corresponding levels of the monomer specific antibody. Apart from these antibodies, the sera did not exhibit other HEV reactivity. The pE2 reactive antibodies evidently had served to prevent the experimental infection in the immunized animals. It was shown fecal virus excretion was abrogated in two immunized animals and in the third animal, the duration of excretion was reduced from 10 or more days, observed in the control animals, to one day. It was further shown that none of the immunized animals harboured detectable viral load in PBMC or plasma specimens and apart from the pE2 specific antibodies, none of these animals had acquired additional HEV antibody after the virus challenge.

The results taken together show that immunization with the recombinantly expressed pE2 peptide has prevented experimental infection of primates with a homologous strain of HEV and that the protection was largely attributed to antibodies against the dimeric form of the pE2 peptide. Since pE2 is highly conserved among different HEV isolates including the most genetically divergent isolates from Mexico (Huang et al., 1992) and the U.S.A. (Schlauder et al., 1998), it is possible that the pE2 peptide may protect against infection by other strains of HEV as well.

The following examples are provided for purposes of illustration of the inventive concepts, and are not intended to limit the scope of the invention as defined by the appended claims.

EXAMPLES

Virus Strain—The Chinese HEV strain with DDBJ accession No. D11092 was a generous gift from Professor H. Zhuang, Beijing Medical University, P.R. China (Aye et al., 1992). It was obtained in the bile of Macaque monkeys, which were experimentally infected according to methods described by Zhuang (Zhuang et al., 1992) with stool specimens taken from hepatitis E patients.

Sera—The ninety-six (96) sera used as described herein were obtained from patients admitted to the Princess Margaret Hospital in Hong Kong with current, or a past history of non-A, B and C acute hepatitis. The specimens were collected from the patients during their hospitalization or at different times after they had been discharged.

downstream primer, ORF2Rc. The new cloned sequence encodes the identical pE2 peptide (i.e. SEQ ID NO: 2), except that the sequence located downstream of the new stop codon has been removed.

TABLE 9

RT and PCR Primers

| Primer* | Purpose | Position | Sequence | Enzyme Site |
|---|---|---|---|---|
| 3R | RT | 5508–5529 | 5'-CGGGGAGTCAACATCAGGCACT-3' (SEQ ID NO:8) | |
| E5R | RT | 7117–7140 | 5'-AAGCAAATAAACTATAACTCCCGA-3' (SEQ ID NO:9) | |
| ORF2F | Cloning | 6326–6350 | 5'-<u>GCTGGATCC</u>CAGCTGTTCTACTCTCGTCCCGTCG-3' (SEQ ID NO:10) | BamHI |
| ORF2Ra | Cloning | 7117–7136 | 5'-<u>GGCGAATTCC</u>AAATAAACTATAACTCCCGA-3' (SEQ ID NO:11) | EcoRI |
| ORF2Rb | Cloning | 6932–6956 | 5'-<u>GGCGAATTC</u>GGGGGGCTAAAACAGCAACCGCGGA-3' (SEQ ID NO:19) | EcoRI |
| ORF2Rc | Cloning | 6943–6968 | 5'-GGCGAATCCCTAGCGCGGAGGGGGGGCTAAAACA-3' (SEQ ID NO:3) | |
| ORF3F | Cloning | 5364–5384 | 5'-<u>CCGGGATCC</u>GACCTCGTGTTCGCCAACCCG-3' (SEQ ID NO:12) | BamHI |
| ORF3R | Cloning | 5457–5477 | 5'-<u>CAGGAATTCC</u>TTAGCGGCGCGGCCCCAGCTG-3' (SEQ ID NO:13) | EcoRI |
| A3R | RT-PCR | 4566–4586 | 5'-GGCTCACCGGAGTGTTTCTTC-3' (SEQ ID NO:14) | |
| A5F | RT-PCR | 4341–4362 | 5'-CTTTGATGACACCGTCTTCTCG-3' (SEQ ID NO:15) | |
| B3R | RT-PCR | 4554–4575 | 5'-GTGTTTCTTCCAAAACCCTCGC-3' (SEQ ID NO:16) | |
| B5F | RT-PCR | 4372–4392 | 5'-GCCGCAGCAAAGCATCCATG-3' (SEQ ID NO:17) | |

*Primers were designed by reference to the sequence of a Chinese HEV isolate (DDBJ accession No. D11092). Non-HEV sequences are underlined.

Example 1

Cloning of the HEV Capsid Gene

Extraction of HEV RNA

Viral RNA was extracted from the bile of an experimentally HEV-infected Macaque monkey (Zhuang et al., 1992) using the QIAamp Virus RNA Kit [QIAGEN GbmH, Hilden, Germany] according to the manufacturer's instructions. The purified RNA was mixed with 2 volumes of isopropanol [BDH Laboratory Supplies, England] and 1/10th volume 3M NaAc (pH 6.4) [Sigma, USA] and left to stand at −20° C. for 1 hour. Afterwards, the mixture was centrifuged at 15,000 rpm for 15 minutes. The pellet was washed once with 70% ethanol [BDH Laboratory Supplies, England] and then resuspended in reverse transcription buffer.

RT-PCR of Target Sequences

For reverse transcription, the RNA pellet was added to 20 μl of RT master mixture (4 μl 5×RT buffer [Boeringer Mannheim]; 1.6 μl of 2.5 mM dNTP; 0.2 μl Avian Myeloblastosis Virus (AMV) [Boeringer Mannheim]; 0.625 μl RNAsin [Boeringer Mannheim]; 1 μl reverse primer E5R or E3R (150 μg/μl); 12.6 μl RNAse-free water) and incubated at 42° C. for 1 hour.

The primers used are listed in Table 9. E3R and E5R were designed to construct cDNA fragments of the virus. The cDNA sequences corresponding to the 3' terminal regions of ORF2 and ORF3 were amplified using the primer pairs ORF2F/ORF2Rb and ORF3F/ORF3R, respectively. These primers were modified to contain BamHI and EcoRI restriction sites to facilitate cloning of the amplified cDNA fragments. All primers were synthesized by Life Technologies, U.S.A.

The original cDNA sequence, which spanned positions 6326 to 7136 with a single base pair deletion at position 6957, was cloned from the ORF2 region using the primer pair ORF2F/ORF2Ra. However, the novel E2 cDNA sequence (i.e. SEQ ID NO: 1) can be cloned from the same region using the same upstream primer, ORF2F, and the new PCR amplification of the target sequence cDNA was carried out by adding 5 μl of cDNA to 45 μl PCR master mixture (5 μl 10×Taq buffer) [Boeringer Mannheim]; 4 μl of 2.5 mM dNTP mixture; 1.0 μl of each primer (150 ng/μl); 1 μl of Taq DNA polymerase (1 U/μl) [Boeringer Mannheim]) and 33 μl ultrapure water. The PCR mixture was overlaid with 50 μl mineral oil. The thermal cycling conditions were: denaturation at 94° C. for 40 seconds; annealing at 57° C. for 40 seconds; and extension at 72° C. for 1 minute. The resulting PCR products were designated E2 and E3 from ORF2 and ORF3, respectively.

Cloning into pGEX Plasmid

The PCR products were extracted with phenol-chloroform and then precipitated with ethanol. The products, E2 and E3, and the vector $pGEX_{20}$ were digested using BamHI and EcoRI (Boeringer Mannheim). The $pGEX_{20}$ vector was a gift from Dr. Cao Liang, Department of Microbiology, the University of Hong Kong. It was a derivative of a pGEX expression vector (Smith et al., 1988) with the multiple cloning site 5'-CCGCGTGGATCCGAAATTCCTCGAGATCGATTAG-3' (SEQ ID NO:20) containing BamHI, EcoRI, XhoI and ClaI restriction cleavage recognition sequences. The digested fragments were separated on agarose gels, recovered by cutting the band out of the gel, electro-elution and then precipitated by ethanol. Afterwards, E2 and E3 were ligated to $pGEX_{20}$ using T4 ligase (Boeringer Mannheim). The recombinant plasmids $pGEX_{20}$-E2 and $pGEX_{20}$-E3 were transformed into *E. Coli* DH5α by electro-transformation with a gene pulser [BIO-RAD] and plated on LB agar plates (Sambrook et al., 1989) with ampicillin (100 μg/ml). Twenty colonies of transformants were picked up for plasmid preparation. BamHI and EcoRI digestion was subsequently carried out and recombinants with the expected insert size were chosen (FIG. 6). All plasmids used in this study were prepared using the QIAgen mini-plasmid kit [QIAgen, Hilden, Germany].

Sequencing

DNA sequencing was performed using an ABI PRISM Dye Terminator Cycle Sequencing Ready Reaction Kit [PERKIN ELMER]. The results showed that the 811 bp E2 sequence was located at position 6326–7136 and also revealed a single base pair deletion at position 6957, presumably due to a PCR amplification error. The resulting frameshift was predicted to cause translation to terminate prematurely at a new stop codon at position 6968 giving a smaller than expected peptide of 213 aa with a MW of 23 kD, instead of 267 aa as initially expected. The position of E2 and relative fragments are shown in FIG. 1.

Example 2

Production and Purification of HEV Peptides

Expression of GST Fusion Protein

The recombinant plasmids were transformed into *E. coli* BL21. Single colonies were picked for growth in 2×YTA medium (tryptone 16 g/l; yeast extract 10 g/l; NaCl 5 g/l; ampicillin 100 µg/l). The overnight culture (4 ml) was inoculated in 400 ml of 2×YTA medium and incubated at 28° C. until the OD600 was ≧0.5. Isopropyl β-D-Thioglactoside (IPTG) [Pharmacia Biotech, U.S.A.] (400 µl of 100 mM solution) was added and the culture grown for 5 to 6 hours. The cells were pelleted by centrifugation at 7,000 rpm for 10 minutes in a Beckman J2-MC rotor JA-14.

Purification

The pellet was washed once in phosphate buffer saline (PBS: 0.8% NaCl; 0.02% KCl; 0.144% $Na_2HPO_4$; 0.024% $KH_2PO_4$, pH 7.0), resuspended in 20 ml PBS and sonicated in a SONIPREP 150 [MSE] (30 seconds on; 30 seconds off; 35 cycles; power 18 to 22). After sonication, Triton-X100 (Sigma, U.S.A.) was added to give a final concentration of 1% and the mixture was gently shaken for 30 minutes. The bacterial lysate was centrifuged at 4° C. and the supernatant was collected. Batch purification of the fusion protein was carried out according to the "GST Fusion Protein System Manual" using glutathione sepharose-4B [Pharmacia Biotech, U.S.A.]. The bound fusion peptide was eluted twice with elution buffer (10 mM reduced glutathione in 50 mM Tris-HCl, pH 8.0) and are referred to as GE2 and GE3 to correspond to the cDNA fragments of ORF2 and ORF3, respectively.

Thrombin Cleavage of Fusion Proteins Bound to Bulk Matrix

Thrombin [Pharmacia Biotech, U.S.A.] (5 µl of a 1 U/µl solution) and 95 µl of PBS were added to a 100 µl bed volume of GE2 bound to glutathione sepharose-4B and incubated at 22° for 16 hours. The supernatant was collected by centrifugation and pooled with the supernatant of a second wash of the matrix. This thrombin-cleaved protein was designated pE2.

Example 3

Identification of HEV Peptides

Analysis of SDS Polyacrylamide Gel Electrophoresis (SDS-PAGE)

A 10% of SDS-polyacrylamide gel was set according to standard methods (Sambrook et al., 1989). The peptide specimens (4 µg) were loaded on the gel and electrophoresed at 100 volts for 3 hours using Minigel Twin G42 [Biometra, Germany]. The gel was stained with Coomassie brillant blue R250 in a mixture of 45 ml methanol, 45 ml $H_2O$ and 10 ml of glacial acetic acid.

Western Blotting

After SDS-PAGE, the proteins in the gel were transferred to 0.45 µm nitrocellulose membranes [BIO-RAD, U.S.A.] at 100 volts for 1 hour using Mini-PROTEAN II Cell [BIO-RAD]. After being blocked with 5% of skim milk [Carnation, Nestle] in 1×PBS at 4° C. overnight, the membrane was reacted with pooled sera (1:500) collected from hepatitis E patients or anti-GST sera (1:1000) obtained from guinea pigs at room temperature for 1.5 hours. After washing three times, 5 minutes each time with 0.05% Tween®$_{20}$ in PBS, the membrane was reacted with horseradish peroxidase (HRP) conjugated Protein-A [BIO-RAD, U.S.A.] at room temperature for another 1.5 hours. After washing three times again, the positive bands were developed by incubation of the membrane with 3-amino-9-ethyl carbazole [AEC Single Solution, ZYMED, U.S.A.] at room temperature for 5 to 10 minutes. The colour reaction was stopped by transferring the membrane into water. The sera and conjugates described above were diluted in blocking buffer (5% of skim milk [Carnation, Nestle] in 1×PBS).

Example 4

Establishment of ELISA to Detect IgG and IgM Anti-HEV

Serum Source

The sera from 96 non-A, B and C hepatitis patients collected at the Princess Margaret Hospital, Hong Kong, was studied. Of these sera, 74 out of 96 were further tested with a commercial HEV kit [Genelabs, Singapore]. Sera from 90 healthy donors was obtained at the Queen Mary Hospital.

ELISA Using HEV Peptide Antigen

The assay specific for either pE2 or pE3 was produced by coating each well of a polystyrene microtitre plate [Nunc, Denmark] with either 0.063 µg/ml of purified pE2 peptide (6.3 ng/100 µl in 0.05 M sodium carbonate, pH 9.5) or with 0.23 µg/µl of GE3 (23.0 ng/100 µl in 0.05 M sodium carbonate, pH 9.5). Concentrations of the peptides used were previously determined to be optimal. After overnight incubation at 4° C., the wells were washed with 350 µl washing buffer (0.05% Tween®$_{20}$ in PBS) and then blocked with 2% bovine serum albumin (BSA) [Sigma, U.S.A.] in PBS at 4° C. for 24 hours. The plates were rewashed twice again with washing buffer. HEV antibody levels were determined by adding 0.1 ml serum specimens at 1:100 dilution to duplicate wells (diluent: 1% BSA, 0.2% Bronidox in PBS). After incubation at 37° C. for 30 minutes, the wells were washed five times with 0.05% Tween®$_{20}$ in PBS. IgM antibodies were determined by reaction with a horseradish peroxidase (HRP)-conjugated human IgM specific antiserum at 1:25,000 dilution [BIOSOURC] and IgG antibodies with a HRP-conjugated protein A at 1:16,000 dilution [BIO-RAD] (diluent: 1% BSA, 0.2% bronidox, 10% sucrose in PBS). After incubation at 37° C. for 30 minutes, the wells were washed five times and 100 µl TMB substrate (3,3',5,5'-tetramethylbenzidine) [Diesse, Italy] was added. The reaction was stopped by 0.3 M $H_2SO_4$ after incubation at 37° C. for 15 minutes. The plate was read at 450 nm with an Anthos 2001 microplate reader [ANTHOS LAB]. To enable comparison of the results obtained on separate test runs, a reference serum was included in each test run, and OD values obtained with test sera on each test run was normalized against that obtained concurrently with the reference sera. Anti-pE2 IgG cut-off values were set at 3 SD above the mean OD value of non-reactive sera previously tested by Western blot. The anti-pE2 IgM cut-off value was set at 3 SD above the mean OD value of the healthy blood donors' sera.

pE2 IgG Avidity Test

The sera was serially diluted and reacted with pE2-coated microplates in duplicate wells. After incubation at 37° C. for 30 minutes, the wells were washed and then treated with PBS (control) or PBS containing 4 M urea at room temperature for 10 minutes. The plate was washed and then reacted with HRP-Protein A conjugate as before.

Example 5

IgG Anti-pE2 Detected by Western Blot

Serum Source

All the sera used in Example 4 was retested by using the Western blot technique.

Western Blot

Thirty-four (34) µg of purified pE2 was loaded to a 70 mm wide single lane SDS-polyacrylamide gel and electrophoresed at 100 volts for 3 hours. After electrophoresis, the peptides were transferred to a 0.45 µm pure nitrocellulose membrane [BIO-RAD] at 100 volts for 1 hour in a MINI-PROTEAN II Cell [BIO-RAD]. After shaking in blocking buffer at 4° C. overnight, the membrane was cut into 2 mm strips. Strips were incubated with each of the sera separately at 1:250 dilution for 1.5 hours. They were subjected to three 5 minute washings in washing buffer and then incubated with goat anti-human IgG alkaline phosphatase conjugate at 1:30,000 [Sigma, U.S.A.] at room temperature for 1.5 hours. After three washings, BCIP/NBT mixture [Gibico BRL, U.S.A.] was added for colour development and the reaction was stopped by putting the strips into water.

The results confirmed that most of the antibody determined by ELISA could be attributed to those which could bind to the dimeric form of pE2, but not its monomeric form.

Example 6

Immune Capture RT-PCR (IC-RT-PCR)

Production of Specific Rabbit Polyclonal Antibodies

The antigen used for production of antibodies to HEV is the pE2 peptide developed as the glutathione S-transferase fusion protein, GE2. Female white rabbits weighing 2.5–3.0 kg were immunized with 100 µg of antigen. The first dose contained an equal volume of complete freund adjuvant. Incomplete freund adjuvant was used in subsequent doses in a 10 to 14 day interval schedule. When specific antibodies rose to a level detectable by ELISA at 1:10,000 dilution of the rabbit serum, the rabbit was given an intravenous booster of 100 µg of the antigen in PBS. On the 4$^{th}$ day after the booster, blood was collected by cardiac puncture. Specific antibodies were evaluated by Western blotting and ELISA.

Preparation of Stool Suspensions

Thirteen acute hepatitis E patient's stool was collected at the First People's Hospital of Guangzhou. Stools of three experimentally HEV-infected monkeys were collected from day 0 to day 30 after HEV inoculation.

Stool specimens (5 g) were mixed with 20 ml 1×PBS and incubated at 4° C. for 1 hour. The mixture was centrifuged at 1500 rpm for 10 minutes and the supernatant was collected for immune capture.

Preparation of Homogenized Suspension of Shellfish

Sixty-four shellfish specimens were collected from street markets around Hong Kong and 17 were collected by the Department of Environmental Protection.

Twenty grams of shellfish meat was blended thoroughly and the homogenate was mixed with 100 ml 0.2 M glycine-0.15 M NaCl buffer (pH 9.5) and 2 ml of stock solution of Cat-Floc (1% w/v). The resulting mixture was vortexed and incubated for 10 minutes at 4° C. The mixture was then centrifuged at 1000 rpm for 5 minutes. The supernatant was collected for immune capture.

HEV Particles Seeding

The bile containing HEV particles was collected from a confirmed experimentally HEV-infected Macaque monkey generously donated by Professor Zhuang Hui (Beijing Medical University). The bile was diluted 200 fold with 1% BSA in PBS and this was referred to as stock solution. The stock solution was diluted from $5^0$ to $5^6$ with five serial dilutions and these were referred to as working solution. A 10 µl aliquot of each of the working solutions was mixed with 5 ml of either water, stool supernatant or shellfish supernatant to produce HEV-seeded specimens for IC-RT-PCR and direct RT-PCR comparison.

Immune Capture

Antiserum, diluted 1:200 with 50 mM sodium carbonate/sodium bicarbonate buffer (pH 9.6), was used as a coating solution. Nunc-Immuno paddle [Nunc, Denmark] was coated by incubation with 1 ml of the coating solution in a tube at 37° C. for 4 hours. The antisera was removed and replaced by 1 ml of 2% bovine serum albumin (BSA) in PBS in which the paddle was incubated at 37° C. for 1 hour. The paddle was then washed with 0.05% Tween®$_{20}$ in PBS and transferred into a tube for immune capture. Shellfish suspension or 20% stool suspension (4.5 ml) was added to the tube and the tube was gently shaken overnight at 4° C. The paddle, referred to as immuno-paddle, was then washed 3 times with 0.05% Tween®$_{20}$ in PBS and transferred to a microcentrifuge tube for RNA extraction and nested RT-PCR for detection of HEV RNA.

Extraction of Viral RNA

RNAse-free water (140 µl) and AVL buffer (560 µl) was added to the tube containing the immuno-paddle. The viral RNA was then extracted according to the instructions of the "QIAgen Viral RNA Handbook". Afterwards, ⅒ volume 2 M sodium acetate (pH 4.6) and 1 volume isopropanol was added to the purified RNA. The mixture was vortexed, left to stand at −20° C. for 1 hour and then centrifuged at 14,000 rpm at 4° C. for 15 minutes. The pellet was rinsed once with pre-cooled 70% ethanol. After centrifugation, the ethanol was carefully removed and the pellet was air-dried at room temperature for 15 minutes before it was reverse transcribed to specific cDNA.

Reverse Transcription (RT) and Nest PCR

Primers used for RT and PCR are listed in Table 9. The outer primer pair was A5F and A3R and the inner primer pair was B5F and B3R.

RT-PCR: Each RNA pellet was mixed with 20 µl of RT master mixture (4 µl 5×RT buffer [Boeringer Mannheim], 1.6 µl 2.5 mM dNTP, 0.2 µl of 25 U/µl Avian Myeloblastosis Virus (AMV) [Boeringer Mannheim], 0.625 µl of 40 U/µl RNAsin [Boeringer Mannheim], 1 µl of 150 ng/µl reverse primer (A3) and 12.6 µl RNAse-free water). After 1 hour incubation at 42° C., cDNA (5 µl) was added to 45 µl PCR master mixture (5 µl 10×Taq buffer [Boeringer Mannheim], 4 µl of 2.5 mM dNTP mixture, 1.0 µl of forward and reverse primer (150 ng/µl) (A3 and A5), 1 µl of 1 U/µl Taq DNA polymerase [Boeringer Mannheim] and 33 µl ultrapure water). The PCR mixture was overlaid with 50 µl mineral oil. The amplification was carried out in a DNA thermal cycler 480 (Perkin-Elmer Cetus) with the following cycling conditions: denaturation at 94° C. for 40 seconds; annealing at 57° C. for 40 seconds; and extension at 72° C. for 1 minute 20 seconds. Processing was carried out for a total of 35 cycles followed by a final auto-extension at 72° C.

Nested PCR and amplicon detection: 2 µl of the first PCR production was added to 48 µl of PCR master mixture which contained the same composition as the first PCR except that the primers were B3 and B5. 5 µl of the PCR product and a 50 bp DNA ladder [GibcoGRL] were loaded to 2% agarose gel in TBE buffer and electrophoresed at 100 volts for 30 minutes. The gel was stained with 0.5 µg/ml ethidium bromide for 15 minutes and then visualized under UV light.

Example 7

The Role of pE2 in HEV Protection

Animals

Wild monkeys, rhesus macaques, were quarantined for 1 month and then bled for a test of ALT and HEV antibodies. The monkeys with ALT/AST over 60 or IgG anti-HEV positive were excluded from the study. The monkeys recruited were divided into three groups, one test group and one control group. Each group consisted of three animals.

Immunization

The test group was immunized by four weekly intramuscular doses, each containing 100 µg of purified pE2. The first dose contained an equal volume of complete freund adjuvant. Incomplete freund adjuvant was used in subsequent doses. The control animals received placebo made up with the respective adjuvants. Serum specimens were obtained weekly for determination of HEV antibodies. When the specific antibodies were elicited to a satisfactory level, the animals were then given an I/V booster. Both groups of the animals were challenged two weeks after the last immunization by intravenous injection of a $10^5$ genome equivalent dose of the homologous strain of HEV. The stool specimens were collected every two days and peripheral blood samples were taken weekly for five weeks after infection. The plasma and peripheral mononuclear blood cells (PMBC) were separated by ficoll-hypaque gradient centrifugation (Kanof et al., 1998). Alanine amino transferase (ALT) levels were determined on freshly collected serum samples in an autoanalyzer (Model 7170, HITACHI, Japan). The plasma specimens were stored for the determination of HEV antibodies and the HEV genome.

Challenge of HEV Particles

Both groups of the animals were challenged two weeks after the last immunization by intravenous injection of $10^5$ genome equivalent dose of the homologous strain of HEV.

Monitoring of Primates

The stool specimens were collected every 2 days and peripheral blood samples were taken weekly for 5 weeks after infection. The plasma and peripheral mononuclear blood cells (PMBC) were separated by ficoll-hypque gradient centrifugation (Kanof et al., 1998). Alanine amino transferase (ALT) levels were determined on freshly collected serum samples in an autoanalyzer (Model 7170, HITACHI, Japan). The plasma specimens were stored for the determination of HEV antibodies and the HEV genome.

The levels of HEV antibodies were determined by a commercial HEV ELISA kit produced by Beijing Medical University and also by an assay produced by coating microtiter plates with the purified pE2 peptide. Antibodies against the purified viral peptides were detected by Western blotting in which approximately 0.5 µg of pE2 or 100 µg of GE3 was loaded on a 70 mm wide slab of 10% SDS-polyacrylamide gel. After electrophoresis, the viral peptide was electrophoretically transblotted onto nitrocellulose membrane. The membrane was shaken in 5% skim milk at 4° C. overnight and cut into 2 mm strips for use. Horseradish perioxidase conjugated Protein-A (BIO-RAD, USA) was used at the dilution 1:2000 as the second antibody.

Viral RNA in PMBC and plasma was extracted using QIAmp RNA blood mini-kit and QIAgen Viral RNA kit (QIAGEN, Germany), respectively, according to the manufacture's instructions. The purified viral RNA was reverse transcribed and then amplified by nested PCR. The primer used for reverse transcription was A3R. The outer primer pair was A5F and A3R and the inner primer pair was B5F and B3R (Table 9).

An immune capture method was used for the detection of HEV in the stool specimens. Polystyrene paddles (Nunc-Immuno paddles, Nunc, Denmark) were coated with 1 ml of 1:100 hyperimmune rabbit anti-pE2 serum at 37° C. for 4 hours. The coated paddle was blocked with 1 ml blocking buffer (2% bovine serum albumin in PBS) at 37° C. for 1 hour. After washing with 0.05% Tween®$_{20}$ in PBS, the paddle was transferred into a tube containing 4.5 ml of 20% stool suspension. The tube was gently shaken overnight at 4° C. The paddle was then washed three times with 0.05% Tween®$_{20}$ in PBS and placed in a clean tube for extraction of RNA using QIAgen Viral RNA kit (QIAGEN, Germany). The purified viral RNA was reverse-transcribed and amplified as previously described.

INDUSTRIAL APPLICABILITY

The highly immunoreactive viral peptide, pE2, cloned from the genome of a Chinese strain of hepatitis E virus (HEV), is extremely useful in the development of reliable diagnostic methods and diagnostic assays for the detection of HEV, as well as in the development of a vaccine composition and a vaccine method for the prevention of HEV in humans.

REFERENCES

Arnon. R. 1987. *Synthetic Vaccines*. *1*:83–92, CRC Press, Inc., Boca Raton, Fla.

Ausubel, F. M. et al., *Current Protocols in Molecular Biology*, John Wiley & Sons, New York, N.Y., 1989.

Aye, T. T., T. Uchida, X. Z. Ma, F. Iida, T. Shikata, H. Zhuang and K. M. Win. 1992. *Complete Nucleotide Sequence of a Hepatitis E Virus Isolated from the Xinjiang Epidemic (1986–1988) of China*. Nucleic Acids Res. 20:3512.

Aye, T. T., T. Uchida, X. Z. Ma, F. Iida, T. Shikata, M. Ichikawa, T. Rikihisa, and K. M. Win. 1993. *Sequence and Gene Structure of the Hepatitis E Virus Isolated from Myanmar*. Virus Genes. 7:95–109.

Balayan, M. S., A. G. Andjaparidze, S. S. Savinskaya, E. S. Ketiladze, D. M. Braginsky, A. P. Savinov, and V. F. Polescschuk. 1983. *Evidence for a Virus in non-A, non-B Hepatitis Transmitted Via the Fecal-Oral Route*. Intervirology. 20:23–31.

Belabbes, E. H., A. Bourgurmouh, A. Benatallah, and G. Illoul. 1985. *Epidemic Non-A, Non-B Viral Hepatitis in Algeria: Strong Evidence for is Spending by Water*. J. Med. Virol. 16:257–263.

Beril, C., J. M. Crance, F. Leguyader, V. Apaire-Marchais, F. Leveque, M. Albert, M. A. Goraguer, L. Schwartzbrod, and S. Billaudel. 1996. *Study of Viral and Bacterial Indicators in Cockle and Mussels*. Marine Pollution Bulletin. 32:404–409.

Berke, T., B. Golding, X. Jiang, W. C. David, M. Wolfaardt, A. W. Smith, and D. O. Matson. 1997. *Phylogenetic Analysis of the Caliciviruses*. J. Med. Virol. 52:419–424.

Bi, S. L., M. A. Purdy, K. A. McCaustland, H. S. Margolis, and D. W. Bradley. 1994. *The Sequence of Hepatitis E Virus Isolated Directly From a Single Source During an Outbreak in China*. Virus Res. 33:98.

Bradley, D. W. and M. S. Balayan. 1988. *Virus of Enterically Transmitted non-A, non-B Hepatitis* [letter]. Lancet. 1:819.

Briton, M. A., and F. X. Heinz. *New Aspects of Positive-Strand RNA Virus*. American Society for Microbiology, Washington D.C., 1990.

Coursaget, P., Y. Buisson, N. Depril, P. L. Canne, M. Chavaud, C. Molinie, and R. Roue. 1993. *Mapping of Linear B Cell Epitopes on Open Reading Frames 2 and 3 Encoded Proteins of Hepatitis E Virus Using Synthetic Peptides*. FEMS Microbiol. Lett. 109:251–256.

Demeke, T. and R. P. Adams. 1992. *The Effects of Plant Polysaccharides and Buffer Additives on PCR* Biotechniques. 12:332–334.

Dilawari, J. B., K. Singh, Y. K. Chawla, G. N. Ramesh, A. Chauhan, S. R. Bhusnurmath, T. R. Sharma, and C. S. Sokhey. 1994. *Hepatitis E Virus: Epidemiological, Clinical and Serological Studies of North Indian Epidemic*. Indian J. Gastroenterol. 13:44–48.

Donati, M. C., E. A. Fagan, and T. J. Harrison. 1997. *Sequence Analysis of Full Length HEV Clones Derived Directly From Human Liver In Fulminant Hepatitis E*. In "Viral Hepatitis E and Liver Diseases" (M. Rizzetto, R. H. Purcell, J. L. Gerin, and G. Verme, Eds.), p.p. 313–316. Edizioni Minerva Medica, Torino.

Harlow and Lane, *Antibodies: A Laboratory Manual*, Cold Spring Harbor Lab., New York, 1988.

Hau, C. H., T. T. Hien, N. T. Tien, H. B. Khiem, P. K. Sac, V. T. Nhung, R. P. Larasati, K. Laras, M. P. Putri, R. Doss, K. C. Hyams, and A. L. Corwin. 1999. *Prevalence of Enteric Hepatitis A and E Viruses in the Mekong River Delta Region of Vietnam*. Am. J. Trop. Med. Hyg. 60:277–280.

Huang, C. C., D. Nguyen, J. Fernandez, K. Y. Yun, K. E. Fry, D. W. Bradley, A. W. Tam, and G. R. Reyes. 1992. *Molecular Cloning and Sequencing of the Mexican Isolate of Hepatitis E Virus (HEV)*. Virology. 191:550–558.

Hussaini, S. H., S. J. Skidmore, P. Richardson, L. M. Sherratt, B. T. Cooper, J. G. O'Grady. 1997. *Severe Hepatitis E Infection During Pregnancy*. J. Viral. Hepat. 4:51–54.

Imai, H., O. Yamada, S. Morita, S. Suehiro, and T. Kurimura. 1992. *Detection of HIV-1 RNA in Heparinized Plasma of HIV-1 Seropositive Individuals*. J. Virol. Methods. 36:181–184.

Kanof, E. M., P. Smith, and H. Zola. 1998. *Isolation of Whole Mononuclear Cells From Peripheral Blood and Cord Blood*. In "Current Protocols in Immunology" (J. E. Coligan, A. H. Kruisbeek, D. M. Margulies, E. M. Shevach, and W. Strober, Eds.), p.p. 7.1.1–7.1.3. John Wiley & Sons, Inc., Greene.

Kennet, R., *Monoclonal Antibodies*, Kenneth et al., Eds., Plenum Press, New York, p.p. 365–367.

Khudyakov, Y. E., M. O. Favorov, D. L. Jue, T. K. Hine, and H. A. Field. 1994. *Immunodominant Antigenic Regions in a Structural Protein of the Hepatitis E Virus*. Virology. 198:390–393.

Khudyakov., Y. E., N. S. Khudyakov, H. A. Field, D. Jue, C. Starling, M. O. Favorov, K. Krawczynski, L. Polish, E. Mast, and H. Margolis. 1993. *Epitope Mapping in Proteins of Hepatitis E Virus*. Virology. 194:89–96.

Khuroo, M. S. 1980. *Study of an Epidemic of non-A, non-B Hepatitis. Possibility of Another Human Hepatitis Virus Distinct From Post-Transfusion non-A, non-B Type*. Am. J. Med. 68:818–824.

Kohler and Milstein, 1975. Nature 256:495–497.

Kolk, A. H., A. R. Schuitema, S. Kuijper, J. van Leeuwen, P. W. Hermans, J. D. van Embden, and R. A. Hartskeerl. 1992. *Detection of Mycobacterium Tuberculosis in Clinical Samples by Using Polymerase Chain Reaction and a Nonradioactive Detection System*. J. Clin. Microbiol. 30:2567–2575.

Krawczynski, K. 1993. *Hepatitis E*. Hepatology. 17:932–941.

Li, F., H. Zhuang, S. Kolivas, S. A. Locamini, and D. A. Anderson. 1994. *Persistent and Transient Antibody Responses to Hepatitis E Virus Detected by Western Immunoblot Using Open Reading Frame 2 and 3 and Glutathione S-Transferase Fusion Proteins*. J Clin Microbiol. 32:2060–2066.

Li, F., J. Torressi, S. A. Locamini, H. Zhuang, W. Zhu, X. Guo, and D. A. Anderson. 1997. *Amino-Terminal Epitopes Are Exposed When Full-Length Open Reading Frame 2 of Hepatitis E Virus is Expressed in Escherichia Coli, but Carboxy-Terminal Epitopes Are Masked*. J Med Virol. 52:289–300.

Li, T. C., Y. Yamakawa, K. Suzuki, M. Tatsumi, M. A. Razak, T. Uchida, N. Takeda, and T. Miyamura. 1997. *Expression and Self-Assembly of Empty Virus-Like Particles of Hepatitis E Virus*. J. Virol. 71:7207–7213.

Myint, H., M. M. Soe, T. Khin, T. M. Myint, and T. M. Tin. 1985. *A Clinical and Epidemiological Study of an Epidemic of Non-A, Non-B Hepatitis in Rangoon*. Am. J. Trop. Med. Hyg. 34:1183–1189.

Panda, S. K., R. Datta, J. Kaur, A. J. Zuckerman, and N. C. Nayak. 1989. *Enterically Transmitted non-A, non-B Hepatitis: Recovery of Virus-Like Particle From an Epidemic in South Delhi and Transmission Studies in Rhesus Monkey*. Hepatology. 10:466–72.

Purdy, M. A, K. A. McCaustland, K. Krawczynski, A. Tam, M. J. Beach, N. C. Tassopoulos, G. R. Reyes, and D. W. Bradley. 1992. *Expression of a Hepatitis E Virus (HEV)-trpE Fusion Protein Containing Epitopes Recognized by Antibodies in Sera From Human Cases and Experimentally Infected Primates*. Arch Virol. 123:335–349.

Purdy, M. A., K. A. McCaustland, K. Krawczynski, J. Spelbring, G. R. Reyes, and D. W. Bradley. 1993. *Preliminary Evidence That a trpE-HEV Fusion Protein Protects Cynomolgus Macaques Against Challenge With Wild-Type Hepatitis E Virus (HEV)*. J. Med. Virol. 41:90–94.

Reyes, G. R., C. C. Huang, A. W. Tam, and M. A. Purdy. 1993. *Molecular Organization and Replication of Hepatitis E Virus (HEV)*. Arch. Virol. Suppl. 7:15–25.

Sambrook et al., *Molecular Cloning: A Laboratory Manual*, 2$^{nd}$ Ed., Cold Spring Harbor Laboratory Press, Plainview, N.Y., 1989.

Schlauder, G. G., G. J. Dawson, J. C. Erker, P. Y. Kwo, M. F. Knigge, D. L. Smalley, J. E. Rosenblatt, S. M. Desai, and I. K. Mushahwar. 1998. *The Sequence and Phylogenetic Analysis of a Novel Hepatitis E Virus Isolated From a Patient With Acute Hepatitis Reported in the United States*. J. Gen. Virol. 79(Pt3):447–456.

Smith, D. B., and K. S. Johnson. 1988. *Single-Step Purification of Polypeptides Expressed in Escherichia Coli as Fusions With Glutathione S-Transferase*. Gene. 67:31–40.

Tam, A. W., M. M. Smith, M. E. Guerra, C. C. Huang, D. W. Bradley, K. E. Fry, and G. R. Reyes. 1991. *Hepatitis E Virus (HEV): Molecular Cloning and Sequencing of the Full-Length Viral Genome*. Virology. 185:120–131.

Tsai, Y. L., C. J. Palmer, and L. R. Sangermano. 1993. *Detection of Escherichia Coli in Sewage and Sludge by Polymerase Chain Reaction*. Appl. Environ. Microbiol. 59:353–357.

Tsai, Y. L. and B. H. Olson. 1992. *Rapid Method for Separation of Bacterial DNA From Humic Substances in Sediments for Polymerase Chain Reaction*. Appl. Environ. Microbiol. 58:2292–2295.

Tsarev, S. A., S. U. Emerson, G. R. Reyes, T. S. Tsareva, L. J. Legters, I. A. Malik, M. Iqbal and R. H. Purcell. 1992. *Characterization of a Prototype Strain of Hepatitis E Virus*. Proc. Natl. Acad. Sci. U.S.A. 89:559–563.

Tsarev, S. A., T. S. Tsareva, S. U. Emerson, A. Z. Kapikian, J. Ticehurst, W. London, and R. H. Purcell. 1993a. *ELISA For Antibody to Hepatitis E Virus (HEV) Based on Complete Open-Reading Frame-2 Protein Expressed in Insect Cells: Identification of HEV Infection in Primates*. J Infect Dis. 168:369–378.

Tsarev, S. A., S. U. Emerson, T. S. Tsareva, P. O. Yarbough, M. Lewis, S. Govindarajan, G. R. Reyes, M. Shapiro and R. H. Purcell. 1993b. *Variation in Course of Hepatitis E in Experimentally Infected Cynomolgus Monkeys*. J. Infect. Dis. 167:1302–1306.

Tsarev, S. A., T. S. Tsareva, S. U. Emerson, S. Govindararjan, M. Shapiro, J. L. Gerin, and R. H. Purcell. 1994a. *Successful Passive and Active Immunization of Cynomolgus Monkeys Against Hepatitis E*. Proc. Natl. Acad. Sci. U.S.A. 91:10198–10202.

Tsarev, S. A., T. S. Tsareva, S. U. Emerson, P. O. Yarbough, L. J. Legters, T. Moskal, and R. H. Purcell. 1994b. *Infectivity Titration of a Prototype Strain of Hepatitis E Virus in Cynomolgus Monkeys*. J. Med. Virol. 43:135–142.

Tsarev, S. A., T. S. Tsareva, S. U. Emerson, S. Govindarajan, M. Shapiro, J. L. Gerin, and R. H. Purcell. 1997. *Recombinant Vaccine Against Hepatitis E: Dose Response and Protection Against Heterologous Challenge*. Vaccine. 15:1834–1838.

Tsega, E., B-G. Hanson, K. Krawezynky, and E. Nordenfelt. 1992. *Acute Sporadic Viral Hepatitis in Ethiopia: Causes, Risk Factors and Effects of Pregnancy*. Clin. Infec. Dis. 14:961–965.

Visvanathan, R. 1957. *Infectious Hepatitis in Delhi (1955–1956): A Critical Study: Epidemiology*. Indian J. Med. Res. (Suppl.). 45:1–30.

Xing, L., K. Kato, T. Li., N. Takeda, T. Miyamura, L. Hammar, and R. H. Cheng. 1999. *Recombinant Hepatitis E Capsid Protein Self-Assembles Into a Dual-Domain T=1 Particle Presenting Native Virus Epitopes*. Virology 265:35–45.

Wong, D. C., R. H. Purcell, M. A. Sreenivasan, S. R. Prasad, and K. M. Pavri. 1980. *Epidemic and Endemic Hepatitis in India: Evidence for Non-A, Non-B Hepatitis Virus Etiology*. Lancet. 2:882–885.

Yarbough, P. O., A. W. Tam, K. E. Fry, K. Krawczynski, K. A. McCaustland, D. W. Bradley, and G. R. Reyes. 1991. *Hepatitis E Virus: Identification of Type-Common Epitopes*. J. Virol. 65:5790–5797.

Yin, S., R. H. Purcell, and S. U. Emerson. 1994. *A New Chinese Isolate of Hepatitis E Virus: Comparison With Strains Recovered From Different Geographical Regions*. Virus Genes. 9:23–32.

Zhang, J. Z., M. H. Ng, N. S. Xia, S. H. Lau, X. Y. Che, T. N. Chau, S. T. Lai, and S. W. K. Im, (In Press). *Conformational Antigenic Determinants Generated By Interactions Between a Bacterially Expressed Recombinant Peptide of the Hepatitis E Virus Structural Protein*. J. Med. Virol.

---

The invention claimed is:

1. A purified and isolated peptide, pE2, consisting of the amino acid sequence identified by SEQ ID NO: 2, wherein the peptide is present as a homodimer thereof.

2. A recombinant fusion protein comprising a heterologous amino acid sequence fused to the peptide pE2 as defined in claim 1.

3. A recombinant fusion protein according to claim 2, characterized in that the heterologous amino acid sequence codes for glutathione S-transferase.

4. A method for producing a purified antibody against the pE2 peptide, as defined in claim 1, comprising injecting into a non-human mammalian host, an immunologically effective amount of the pE2 peptide, and isolating and purifying the antibody produced.

5. A vaccine composition for immunizing an individual against infection from hepatitis E virus (HEV) comprising the pE2 peptide, as defined in claim 1, and a pharmacologically acceptable carrier.

6. A method for immunizing an individual against infection from hepatitis E virus, which comprises steps of administration of a vaccine composition as defined in claim 5 into subject in need.

7. A method for determining the presence or absence of HEV antibodies in a biological test sample, comprising:

providing a purified and isolated peptide, pE2 according to claim 1;

contacting the biological test sample suspected of containing HEV antibodies with said pE2 peptide;

incubating the resultant mixture under conditions sufficient to allow the formation of an immunological (antibody-antigen) complex; and examining the mixture for the presence of such an immunological complex, whereby the formation of the complex indicates the presence of HEV antibodies in the test sample.

8. A method according to claim 7, characterized in that the biological test sample is human blood, serum or plasma.

9. A method according to claim 7, characterized in that the presence of the immunological complex is determined following incubation with an indicator reagent under conditions permitting a reaction to occur.

10. A method according to claim 9, characterized in that the indicator reagent is a mammalian anti-human immunoglobulin attached to an enzyme which reacts with a substrate to form a colored product.

11. A diagnostic test kit for the detection of antibodies to hepatitis E virus (HEV), comprising:

a purified and isolated peptide, pE2, according to claim 1; and an indicator reagent capable of detecting an immunological (antigenantibody) complex which contains said pE2 peptide.

12. A diagnostic test kit according to claim 11, which further comprises:—control standards; and
a specimen diluent and/or washing buffer.

13. A diagnostic test kit according to claim 11, characterized in that said peptide, pE2, is immobilized to a solid support.

14. A diagnostic test kit according to claim 13, characterized in that the solid support is the well of a titration microplate.

15. A diagnostic test kit for the detection of antibodies to hepatitis E virus (HEV), comprising:
a purified and isolated peptide, pE2, comprising the amino acid sequence identified by SEQ ID NO: 2, wherein the peptide is present as a homodimer;
an indicator reagent capable of detecting an immunological (antigen-antibody) complex which contains the pE2 peptide, and at least one of the following:
a) a solid support immobilizing the pE2 peptide; and
b) a well of a titration microplate containing the pE2 peptide.

* * * * *

SEQUENCE LISTING

```
<160> NUMBER OF SEQ ID NOS: 20

<210> SEQ ID NO 1
<211> LENGTH: 642
<212> TYPE: DNA
<213> ORGANISM: Hepatitis E virus
<220> FEATURE:
<221> NAME/KEY: CDS
<222> LOCATION: (1)..(642)

<400> SEQUENCE: 1 cag ctg ttc tac tct cgt ccc gtc gtc tca gcc aat ggc gag ccg act      48
Gln Leu Phe Tyr Ser Arg Pro Val Val Ser Ala Asn Gly Glu Pro Thr
1               5                   10                  15 gtt aag ctt tat aca tct gta gag aat gct cag cag gat aag ggt att      96
Val Lys Leu Tyr Thr Ser Val Glu Asn Ala Gln Gln Asp Lys Gly Ile
            20                  25                  30 gca atc ccg cat gac atc gac ctc ggg gag tct cgt gta gtt att cag     144
Ala Ile Pro His Asp Ile Asp Leu Gly Glu Ser Arg Val Val Ile Gln
        35                  40                  45
```

```
gat tat gac aac caa cat gag cag gac cga ccg aca cct tcc cca gcc    192
Asp Tyr Asp Asn Gln His Glu Gln Asp Arg Pro Thr Pro Ser Pro Ala
    50                  55                  60 cca tcg cgc cct ttt tct gtc ctc cga gct aat gat gtg ctt tgg ctt    240
Pro Ser Arg Pro Phe Ser Val Leu Arg Ala Asn Asp Val Leu Trp Leu
65                  70                  75                  80 tct ctc acc gct gcc gag tat gac cag tcc act tac ggc tct tcg acc    288
Ser Leu Thr Ala Ala Glu Tyr Asp Gln Ser Thr Tyr Gly Ser Ser Thr
                85                  90                  95 ggc cca gtc tat gtc tct gac tct gtg acc ttg gtt aat gtt gcg acc    336
Gly Pro Val Tyr Val Ser Asp Ser Val Thr Leu Val Asn Val Ala Thr
            100                 105                 110 ggc gcg cag gcc gtt gcc cgg tca ctc gac tgg acc aag gtc aca ctt    384
Gly Ala Gln Ala Val Ala Arg Ser Leu Asp Trp Thr Lys Val Thr Leu
        115                 120                 125 gat ggt cgc ccc ctt tcc acc atc cag cag tat tca aag acc ttc ttt    432
Asp Gly Arg Pro Leu Ser Thr Ile Gln Gln Tyr Ser Lys Thr Phe Phe
130                 135                 140 gtc ctg ccg ctc cgc ggt aag ctc tcc ttt tgg gag gca ggt act act    480
Val Leu Pro Leu Arg Gly Lys Leu Ser Phe Trp Glu Ala Gly Thr Thr
145                 150                 155                 160 aaa gcc ggg tac cct tat aat tat aac acc act gct agt gac caa ctg    528
Lys Ala Gly Tyr Pro Tyr Asn Tyr Asn Thr Thr Ala Ser Asp Gln Leu
                165                 170                 175 ctc gtt gag aat gcc gct ggg cat cgg gtt gct att tcc act tac acc    576
Leu Val Glu Asn Ala Ala Gly His Arg Val Ala Ile Ser Thr Tyr Thr
            180                 185                 190 act agc ctg ggt gct ggt ccc gtc tct att tcc gcg gtt gct gtt tta    624
Thr Ser Leu Gly Ala Gly Pro Val Ser Ile Ser Ala Val Ala Val Leu
        195                 200                 205 gcc ccc cct ccg cgc tag                                            642
Ala Pro Pro Pro Arg
210

<210> SEQ ID NO 2
<211> LENGTH: 213
<212> TYPE: PRT
<213> ORGANISM: Hepatitis E virus

<400> SEQUENCE: 2

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Ser Thr Tyr Gly Ser Ser Thr
                85                  90                  95

Gly Pro Val Tyr Val Ser Asp Ser Val Thr Leu Val Asn Val Ala Thr
            100                 105                 110

Gly Ala Gln Ala Val Ala Arg Ser Leu Asp Trp Thr Lys Val Thr Leu
        115                 120                 125

Asp Gly Arg Pro Leu Ser Thr Ile Gln Gln Tyr Ser Lys Thr Phe Phe
130                 135                 140
```

| Val | Leu | Pro | Leu | Arg | Gly | Lys | Leu | Ser | Phe | Trp | Glu | Ala | Gly | Thr | Thr |
| 145 | | | | | 150 | | | | | 155 | | | | | 160 |

| Lys | Ala | Gly | Tyr | Pro | Tyr | Asn | Tyr | Asn | Thr | Thr | Ala | Ser | Asp | Gln | Leu |
| | | | | 165 | | | | | 170 | | | | | 175 | |

| Leu | Val | Glu | Asn | Ala | Ala | Gly | His | Arg | Val | Ala | Ile | Ser | Thr | Tyr | Thr |
| | | | 180 | | | | | 185 | | | | | 190 | | |

| Thr | Ser | Leu | Gly | Ala | Gly | Pro | Val | Ser | Ile | Ser | Ala | Val | Ala | Val | Leu |
| | | 195 | | | | | 200 | | | | | 205 | | | |

| Ala | Pro | Pro | Arg |
| 210 | | | |

<210> SEQ ID NO 3
<211> LENGTH: 34
<212> TYPE: DNA
<213> ORGANISM: Artificial
<220> FEATURE:
<223> OTHER INFORMATION: Cloning Primer ORF2Rc

<400> SEQUENCE: 3
ggcgaatccc tagcgcggag gggggctaa aaca                             34

<210> SEQ ID NO 4
<211> LENGTH: 2054
<212> TYPE: DNA
<213> ORGANISM: Hepatitis E virus

<400> SEQUENCE: 4

| atgcgccctc ggcctatttt gctgttgctc ctcatgtttc tgcctatgct gcccgcgcca | 60 |
| ccgcccggtc agccgtctgg ccgccgtcgt gggcggcgca gcggcggttc ggcggtggt | 120 |
| ttctggggtg accgggttga ttctc

```
caggattatg acaaccaaca tgagcaggac cgaccgacac cttccccagc cccatcgcgc    1380 ccttttctg  tcctccgagc taatgatgtg ctttggcttt ctctcaccgc tgccgagtat    1440
gaccagtcca cttacggctc ttcgaccggc ccagtctatg tctctgactc tgtgaccttg    1500
gttaatgttg cgaccggcgc gcaggccgtt gcccggtcac tcgactggac caaggtcaca    1560
cttgatggtc gccccctttc caccatcaag cagtattcaa agaccttctt tgtcctgccg    1620
ctccgcggta agctctcctt tgggaggca  ggtactacta agccgggta  cccttataat    1680 tataacacca ctgctagtga ccaactgctc gttgagaatg ccgctgggca tcgggttgct    1740
atttccactt acaccactag cctgggtgct ggtcccgtct ctatttccgc ggttgctgtt    1800 ttagccccc  actccgcgct agcattgctt gaggatacca tggactaccc tgcccgcgcc    1860
catactttcg atgacttctg cccggagtgc cgccccttg  gcctccaggg ctgtgctttt    1920
cagtctactg tcgctgagct tcagcgcctt aagatgaagg tgggtaaaac tcgggagtta    1980
tagtttattt gcttgtgccc cccttctttc tgttgcttat ttctcttttc tgcgttccgc    2040
gctccctgaa aaaa                                                     2054

<210> SEQ ID NO 5
<211> LENGTH: 370
<212> TYPE: DNA
<213> ORGANISM: Hepatitis E virus

<400> SEQUENCE: 5
tgaataacat gtcttttgct gcgcccatgg gttcgcgacc atgcgccctc ggcctatttt     60
gctgttgctc ctcatgtttc tgcctatgct gcccgcgcca ccgcccggtc agccgtctgg    120
ccgccgtcgt gggcggcgca gcggcggttc cggcggtggt ttctggggtg accgggttga    180
ttctcagccc ttcgcaatcc cctatattca tccaaccaac cccttcgccc cgatgtcacc    240
gctgcggccg gggctggacc tcgtgttcgc caacccgccc gaccactcgg ctccgcttgg    300
cgtgaccagg cccagcgccc cgccgttgcc tcacgtcgta gacctaccac agctggggcc    360
gcgccgctaa                                                           370

<210> SEQ ID NO 6
<211> LENGTH: 114
<212> TYPE: DNA
<213> ORGANISM: Hepatitis E virus
<220> FEATURE:
<221> NAME/KEY: CDS
<222> LOCATION: (1)..(114)

<400> SEQUENCE: 6 gac ctc gtg ttc gcc aac ccg ccc gac cac tcg gct ccg ctt ggc gtg      48
Asp Leu Val Phe Ala Asn Pro Pro Asp His Ser Ala Pro Leu Gly Val
1               5                   10                  15 acc agg ccc agc gcc ccg ccg ttg cct cac gtc gta gac cta cca cag      96
Thr Arg Pro Ser Ala Pro Pro Leu Pro His Val Val Asp Leu Pro Gln
            20                  25                  30 ctg ggg ccg cgc cgc taa                                             114
Leu Gly Pro Arg Arg
            35

<210> SEQ ID NO 7
<211> LENGTH: 37
<212> TYPE: PRT
<213> ORGANISM: Hepatitis E virus

<400> SEQUENCE: 7
```

```
Asp Leu Val Phe Ala Asn Pro Pro Asp His Ser Ala Pro Leu Gly Val
1               5                   10                  15

Thr Arg Pro Ser Ala Pro Pro Leu Pro His Val Val Asp Leu Pro Gln
                20                  25                  30

Leu Gly Pro Arg Arg
        35

<210> SEQ ID NO 8
<211> LENGTH: 22
<212> TYPE: DNA
<213> ORGANISM: Artificial
<220> FEATURE:
<223> OTHER INFORMATION: RT Primer E3R

<400> SEQUENCE: 8
cggggagtca acatcaggca ct                                          22

<210> SEQ ID NO 9
<211> LENGTH: 24
<212> TYPE: DNA
<213> ORGANISM: Artificial
<220> FEATURE:
<223> OTHER INFORMATION: RT Primer E5R

<400> SEQUENCE: 9
aagcaaataa actataactc ccga                                        24

<210> SEQ ID NO 10
<211> LENGTH: 34
<212> TYPE: DNA
<213> ORGANISM: Artificial
<220> FEATURE:
<223> OTHER INFORMATION: Cloning Primer ORF2F

<400> SEQUENCE: 10
gctggatccc agctgttcta ctctcgtccc gtcg                             34

<210> SEQ ID NO 11
<211> LENGTH: 30
<212> TYPE: DNA
<213> ORGANISM: Artificial
<220> FEATURE:
<223> OTHER INFORMATION: Cloning Primer ORF2Ra

<400> SEQUENCE: 11
ggcgaattcc aaataaacta taactcccga                                  30

<210> SEQ ID NO 12
<211> LENGTH: 30
<212> TYPE: DNA
<213> ORGANISM: Artificial
<220> FEATURE:
<223> OTHER INFORMATION: Cloning Primer ORF3F

<400> SEQUENCE: 12
ccgggatccg acctcgtgtt cgccaacccg                                  30

<210> SEQ ID NO 13
<211> LENGTH: 31
<212> TYPE: DNA
<213> ORGANISM: Artificial
<220> FEATURE:
<223> OTHER INFORMATION: Cloning Primer ORF3R

<400> SEQUENCE: 13
```

```
caggaattcc ttagcggcgc ggccccagct g                                          31
```

<210> SEQ ID NO 14
<211> LENGTH: 21
<212> TYPE: DNA
<213> ORGANISM: Artificial
<220> FEATURE:
<223> OTHER INFORMATION: PCR Primer A3R

<400> SEQUENCE: 14

```
ggctcaccgg agtgtttctt c                                                     21
```

<210> SEQ ID NO 15
<211> LENGTH: 22
<212> TYPE: DNA
<213> ORGANISM: Artificial
<220> FEATURE:
<223> OTHER INFORMATION: PCR Primer A5F

<400> SEQUENCE: 15

```
ctttgatgac accgtcttct cg                                                    22
```

<210> SEQ ID NO 16
<211> LENGTH: 22
<212> TYPE: DNA
<213> ORGANISM: Artificial
<220> FEATURE:
<223> OTHER INFORMATION: PCR Primer B3R

<400> SEQUENCE: 16

```
gtgtttcttc caaaaccctc gc                                                    22
```

<210> SEQ ID NO 17
<211> LENGTH: 21
<212> TYPE: DNA
<213> ORGANISM: Artificial
<220> FEATURE:
<223> OTHER INFORMATION: PCR Primer B5F

<400> SEQUENCE: 17

```
gccgcagcaa aggcatccat g                                                     21
```

<210> SEQ ID NO 18
<211> LENGTH: 213
<212> TYPE: PRT
<213> ORGANISM: Hepatitis E virus

<400> SEQUENCE: 18

```
Gln Leu Phe Tyr Ser Arg Pro Val Val Ser Ala Asn Gly Glu Pro Thr
1               5                   10                  15
Val Lys Leu Tyr Thr Ser Val Glu Asn Ala Gln Gln Asp Lys Gly Ile
            20                  25                  30
Ala Ile Pro His Asp Ile Asp Leu Gly Glu Ser Arg Val Val Ile Gln
        35                  40                  45
Asp Tyr Asp Asn Gln His Glu Gln Asp Arg Pro Thr Pro Ser Pro Ala
    50                  55                  60
Pro Ser Arg Pro Phe Ser Val Leu Arg Ala Asn Asp Val Leu Trp Leu
65                  70                  75                  80
Ser Leu Thr Ala Ala Glu Tyr Asp Gln Ser Thr Tyr Gly Ser Ser Thr
                85                  90                  95
Gly Pro Val Tyr Val Ser Asp Ser Val Thr Leu Val Asn Val Ala Thr
            100                 105                 110
```

-continued

```
Gly Ala Gln Ala Val Ala Arg Ser Leu Asp Trp Thr Lys Val Thr Leu
        115                 120                 125

Asp Gly Arg Pro Leu Ser Thr Ile Gln Gln Tyr Ser Lys Thr Phe Phe
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Leu
                165                 170                 175

Leu Val Glu Asn Ala Ala Gly His Arg Val Ala Ile Ser Thr Tyr Thr
            180                 185                 190

Thr Ser Leu Gly Ala Gly Pro Val Ser Ile Ser Ala Val Ala Val Leu
        195                 200                 205

Ala Pro Pro Pro Arg
    210

<210> SEQ ID NO 19
<211> LENGTH: 34
<212> TYPE: DNA
<213> ORGANISM: Artificial
<220> FEATURE:
<223> OTHER INFORMATION: Cloning Primer ORF2Rb

<400> SEQUENCE: 19
ggcgaattcg gggggctaaa acagcaaccg cgga                             34

<210> SEQ ID NO 20
<211> LENGTH: 34
<212> TYPE: DNA
<213> ORGANISM: Artificial
<220> FEATURE:
<223> OTHER INFORMATION: pGEX20 Multiple Cloning Site

<400> SEQUENCE: 20
ccgcgtggat ccgaaattcc tcgagatcga ttag                             34
```